US009844656B2

(12) United States Patent
Ferrara et al.

(10) Patent No.: US 9,844,656 B2
(45) Date of Patent: Dec. 19, 2017

(54) LOCALIZATION OF AGENTS AT A TARGET SITE WITH A COMPOSITION AND AN ENERGY SOURCE

(75) Inventors: Katherine W. Ferrara, Davis, CA (US); Azedah Kheirolomoom, Sacramento, CA (US)

(73) Assignee: The Regents of the University of California, Oakland, CA (US)

( * ) Notice: Subject to any disclaimer, the term of this patent is extended or adjusted under 35 U.S.C. 154(b) by 1339 days.

(21) Appl. No.: 13/581,274

(22) PCT Filed: Mar. 1, 2011

(86) PCT No.: PCT/US2011/026592
§ 371 (c)(1),
(2), (4) Date: Sep. 13, 2012

(87) PCT Pub. No.: WO2011/109334
PCT Pub. Date: Sep. 9, 2011

(65) Prior Publication Data
US 2013/0090591 A1 Apr. 11, 2013

Related U.S. Application Data

(60) Provisional application No. 61/309,374, filed on Mar. 1, 2010.

(51) Int. Cl.
| | | |
|---|---|---|
| *A61K 9/127* | (2006.01) | |
| *A61M 37/00* | (2006.01) | |
| *A61K 9/00* | (2006.01) | |
| *A61K 9/107* | (2006.01) | |
| *A61K 31/704* | (2006.01) | |
| *A61K 33/34* | (2006.01) | |

(Continued)

(52) U.S. Cl.
CPC ....... *A61M 37/0092* (2013.01); *A61K 9/0009* (2013.01); *A61K 9/0019* (2013.01); *A61K 9/107* (2013.01); *A61K 9/127* (2013.01); *A61K 9/1271* (2013.01); *A61K 9/1273* (2013.01); *A61K 9/1277* (2013.01); *A61K 31/704* (2013.01); *A61K 33/34* (2013.01); *A61K 41/0028* (2013.01); *A61K 45/06* (2013.01)

(58) Field of Classification Search
CPC ..................................................... A61K 9/127
See application file for complete search history.

(56) References Cited

U.S. PATENT DOCUMENTS

2003/0091621 A1* 5/2003 Tardi et al. ................... 424/450
2008/0107722 A1  5/2008 Tardi et al.
2010/0129430 A1* 5/2010 Sofou .................. A61K 9/1271
424/450

FOREIGN PATENT DOCUMENTS

CA WO 2007076117 A2 * 7/2007 ........... A61K 9/1278

OTHER PUBLICATIONS

Kheirolomoom, A. et al., "Complete Regression of Local Cancer Using Temperature-Sensitive Liposomes Combined with Ultrasound-Mediated Hyperthermia," Journal of Controlled Release, 2013, pp. 266-273, vol. 172.

(Continued)

*Primary Examiner* — Benjamin Packard
(74) *Attorney, Agent, or Firm* — Fenwick & West LLP

(57) ABSTRACT

A method for localizing delivery of an agent to a target site in a subject is provided. The method allows accumulation and/or release of the agent at the target site in the subject through the use of an energy source.

39 Claims, 31 Drawing Sheets

(51) Int. Cl.
    A61K 41/00    (2006.01)
    A61K 45/06    (2006.01)

(56) References Cited

OTHER PUBLICATIONS

Abraham, S. A. et al., "Formation of Transitional Metal-Doxorubicin Complexes Inside Lipsomes," Biochimica Et Biophysica Acta-Biomembranes, 2002, pp. 41-54, vol. 1565, No. 1.
Allen, T. et al., "Pharmacokinetics and Pharmacodynamics of Lipidic Nano-Particles in Cancer," Anti-Cancer Agents Medicinal Chemistry, 2006, pp. 513-523, vol. 6, No. 6.
An, S.Y. et al., "Preparation of Monodisperse and Size-Controlled Poly(Ethylene Glycol) Hydrogel Nanoparticles Using Liposome Templates," Journal of Colloid and Interface Science, 2009, pp. 98-103, vol. 331.
Andresen, T. L. et al. "Advances Strategies in Liposomal Cancer Therapy: Problems and Prospects of Active and Tumor Specific Drug Release," Progress in Lipid Research, 2005, pp. 68-97, vol. 44, No. 1.
Batist, G. et al., "Reduced Cardiotoxicity and Preserved Antitumor Efficacy of Liposome-Encapsulated Doxorubicin and Cyclophosphamide Compared with Conventional Doxorubicin and Cyclophospamide in a Randomized, Multicenter Trial of Metastatic Breast Cancer," Journal of Clinical Oncology, 2001, pp. 1444-1454, vol. 19, No. 5.
Beraldo, H. et al., "Copper(II)-Adriamycin Complexes. A Circular Dichroism and Resonance Raman Study," Inorganic Chemistry, 1983, pp. 4117-4124, vol. 22, No. 26.
Chen, W. et al., "pH-Sensitive Degradable Polymersomes for Triggered Release of Anticancer Drugs: A Comparative Study with Micelles," Journal of Controlled Release, 2010, pp. 40-46, vol. 142.
Chen B. et al., "The Influence of Polymer Topology on Pharmacokinetics: Differences Between Cyclic and Linear PEGylated Poly(Acrylic Acid) Comb Polymers," Journal of Controlled Release, 2009, pp. 203-209, vol. 140.
Cheung, B.C.L et al., "Loading of Doxorubicin Into Liposomes by Forming $Mn^{2+}$-Drug Complexes," Biochimica Et Biophysica Acta, 1998, pp. 205-216, vol. 1414, No. 1-2.
Chiu, G.N.C. et al., "Encapsulation of Doxorubicin Into Thermosensitive Liposomes Via Complexation with the Transition Metal Manganese," Journal of Controlled Release, 2005, pp. 271-288, vol. 104, No. 2.
Clerc, S. et al., "Loading of Amphipathic Weak Acids Into Liposomes in Response to Transmembrane Calcium Acetate Gradients," Biochimica Et Biophysica Acta,1995, pp. 257-265, vol. 1240, No. 2.
Dicko, A. et al., "Role of Copper Gluconate/Triethanolamine in Irinotecan Encapsulation Inside the Liposomes," International Journal of Pharmaceutics, 2007, pp. 219-228, vol. 337, No. 1-2.
Drummond, D. et al., "Pharmacokinetics and In Vivo Drug Release Rates in Liposomal Nanocarrier Development," Journal of Pharmaceutical Sciences, Nov. 2008, pp. 4696-4740, vol. 97, No. 11.
Gabizon, A. A. et al., "Prolongation of the Circulation Time of Doxorubicin Encapsulated in Liposomes Containing a Polyethylene Glycol-Derivatized Phospholipid: Pharmacokinetic Studies in Rodents and Dogs," Pharmaceutical Research, 1993, pp. 703-708, vol. 10, No. 5.
Gianni, L. et al., "Anthracycline Cardiotoxicity: From Bench to Bedside," Journal of Clinical Oncology, Aug. 1, 2008, pp. 3777-3784, vol. 26, No. 22.
Greenaway, F. T. et al., "The Binding of Copper Ions to Daunomycin and Adriamycin," Journal of Inorganic Biochemistry, 1982, pp. 91-107, vol. 16, No. 2.
Haran, G. et al., "Transmembrane Ammonium Sulfate Gradients in Liposomes Produce Efficient and Stable Entrapment of Amphipathic Weak Bases," Biochimica Et Biophysica Acta, 1993, pp. 201-215, vol. 1151, No. 2.

Kheirolomoom, A. et al., "Cholesterol Transport from Liposomal Delivery Vehicles," Biomaterials, Oct. 2007, pp. 4311-4320, vol. 28, No. 29.
Kheirolomoom, A. et al., "Enhanced In Vivo Bioluminescence Imaging Using Liposomal Luciferin Delivery System," Journal of Controlled Release, 2010, pp. 128-136, vol. 141, No. 2.
Kheirolomoom, A. et al., "Acoustically-Active Microbubbles Conjugated to Liposomes: Characterization of a Proposed Drug Delivery Carrier," Journal of Controlled Release, 2007, pp. 275-284, vol. 118, No. 3.
Kheirolomoom, A. et al., "Copper-Doxorubicin as a Nanoparticle Cargo Retains Efficacy with Minimal Toxicity," Molecular Pharmaceutics, 2010, pp. 1948-1958, vol. 7, No. 6.
Kim, K. W. et al., "Combined Bcl-2/mTOR Inhibition Leads to Enhanced Radiosensitization Via Induction of Apoptosis and Autophagy in Non-Small-Cell Lung Tumor Xenograft Model," Clinical Cancer Research, Oct. 2009, pp. 6096-6105, vol. 15, No. 19.
Lasic, D.D. et al., "Transmembrane Gradient Driven Phase Transitions Within Vesicles: Lessons for Drug Delivery," Biochimica et Biophysica Acta-Biomembranes 1995, pp. 145-156, vol. 1239, No. 2.
Lewis, G., Jr. et al., "Therapeutic Ultrasound Enhancement of Drug Delivery to Soft Tissues," AIP Conference Proceedings, $8^{th}$ International Symposium on Therapeutic Ultrasound, 2009, pp. 403-407, vol. 1113.
Li, X. G. et al., "Doxorubicin Physical State in Solution and Inside Liposomes Loaded Via a pH Gradient," Biochimica Et Biophysica Acta-Biomembranes, 1998, pp. 23-40, vol. 1415, No. 1.
Madden, T. D. et al., "The Accumulation of Drugs Within Large Unilamellar Vesicles Exhibiting a Proton Gradient: A Survey," Chemistry and Physics of Lipids, 1990, pp. 37-46, vol. 53, No. 1.
Maeda, H., The Enhanced Permeability and Retention (EPR) Effect in Tumor Vasculature: The Key Role of Tumor-Selective Macromolecular Drug Targeting, Advances in Enzyme Regulation, ed. Weber, G., Pergamon-Elsevier Science Ltd: Oxford, 2001, pp. 189-207, vol. 41.
May, P. M. et al., "Solution Chemistry Studies of Adriamycin-Iron Complexes Present in Vivo," European Journal of Cancer, 1980, pp. 1275-1276, vol. 16, No. 9.
Mayer, L. D. et al., "Uptake of Antineoplastic Agents into Large Unilamellar Vesicles in Response to a Membrane Potential," Biochimica Et Biophysica Acta, 1985, pp. 294-302, vol. 816, No. 2.
Monsky, W. L. et al., "Augmentation of Transvascular Transport of Macromolecules and Nanoparticles in Tumors Using Vascular Endothelial Growth Factor," Cancer Research, Aug. 15, 1999, pp. 4129-4135, vol. 59, No. 16.
Muneeb, A. et al., "Combined Radiofrequency Ablation and Adjuvant Liposomal Chemotherapy: Effect of Chemotherapeutic Agent, Nanoparticle Size, and Circulation Time," Journal of vascular and interventional radiology: JVIR 2005, pp. 1365-1371, vol. 16, No. 10.
Namba, R. et al., "Rapamycin Inhibits Growth of Premalignant and Malignant Mammary Lesions in a Mouse Model of Ductal Carcinoma In Situ," Clinical Cancer Research, 2006,pp. 2613-2621, vol. 12, No. 8.
Palmer, G. M. et al., "Non-Invasive Monitoring of Intra-Tumor Drug Concentration and Therapeutic Response Using Optical Spectroscopy," Journal of Controlled Release, 2010, pp. 457-464, vol. 142, No. 3.
PCT International Search Report and Written Opinion, PCT Application No. PCT/US2011/026592, dated Nov. 28, 2011, 11 pages.
Ramsay, E. et al., "Transition Metal-Mediated Liposomal Encapsulation of Irinotecan (CPT-11) Stabilizes the Drug in the Therapeutically Active Lactone Conformation," Pharmaceutical Research, Dec. 2006, pp. 2799-2808, vol. 23, No. 12.
Ridge, J. A. et al., "Increased Adriamycin Levels in Hepatic Implants of Rabbit Vx-2 Carcinoma from Regional Infusion," Cancer Research, 1988, pp. 4584-4587, vol. 48, No. 16.
Senger, D. R. et al., "Tumor Cells Secrete a Vascular Permeability Factor That Promotes Accumulation of Ascites Fluid," Science, Feb. 25, 1983, pp. 983-985, vol. 219, No. 4587.

(56) References Cited

OTHER PUBLICATIONS

Seo, J.W. et al., "A Novel Method to Label Performed Liposomes with $^{64}$Cu for Positron Emission Tomography (PET) Imaging," Bioconjugate Chemistry, 2008, pp. 2577-2584, vol. 19, No. 12.

Tardi, P.G. et al., "Coencapsulation of Irinotecan and Floxuridine Into Low Cholesterol-Containing Liposomes That Coordinate Drug Release in Vivo," Biochimica Et Biophysica Acta-Biomembranes, 2007, pp. 678-687, vol. 1768, No. 3.

Tritton, T.R. et al., "The Anticancer Agent Adriamycin Can Be Actively Cytotoxic Without Entering Cells," Science, Jul. 16, 1982, pp. 248-250, vol. 217, No. 4556.

Unezaki, S. et al., "Enhanced Tumor Targeting and Improved Antitumor Activity of Doxorubicin by Long-Circulating Liposomes Containing Amphipathic Poly(ethylene Glycol)," International Journal of Pharmaceutics, 1995, pp. 41-48, vol. 126, 1-2.

Van Hoesel, Q. et al., "Reduced Cardiotoxicity and Nephrotoxicity with Preservation of Antitumor Activity of Doxorubicin Entrapped in Stable Liposomes in the LOU/M Wsl Rat," Cancer Research, Sep. 1984, pp. 3698-3705, vol. 44, No. 9.

Wallace, K.B., "Nonenzymatic Oxygen Activation and Stimulation of Lipid Peroxidation by Doxorubicin-Copper," Toxicology and Applied Pharmacology 1986, pp. 67-79, vol. 86, No. 1.

Weinberg, B.D. et al., "Model Simulation and Experimental Validation of Intratumoral Chemotherapy Using Multiple Polymer Implants," Medical & Biological Engineering & Computing, 2008, pp. 1039-1049, vol. 46, No. 10.

Working, P. K. et al., "Pharmacokinetics, Biodistribution and Therapeutic Efficacy of Doxorubicin Encapsulated in Stealth® Liposomes (Doxil®)," Journal of Liposome Research, 1994, pp. 667-687, vol. 4, No. 1.

Yuan, F. et al., "Microvascular Permeability and Interstitial Penetration of Sterically Stabilized (Stealth) Liposomes in a Human Tumor Xenograft," Cancer Research, Jul. 1, 1994, pp. 3352-3356, vol. 54, No. 13.

Kheirolomoom, A. et al., "Intracellular Trafficking of a pH-Responsive Drug Metal Complex," Journal of Controlled Release, 2016, pp. 232-242, vol. 243.

\* cited by examiner

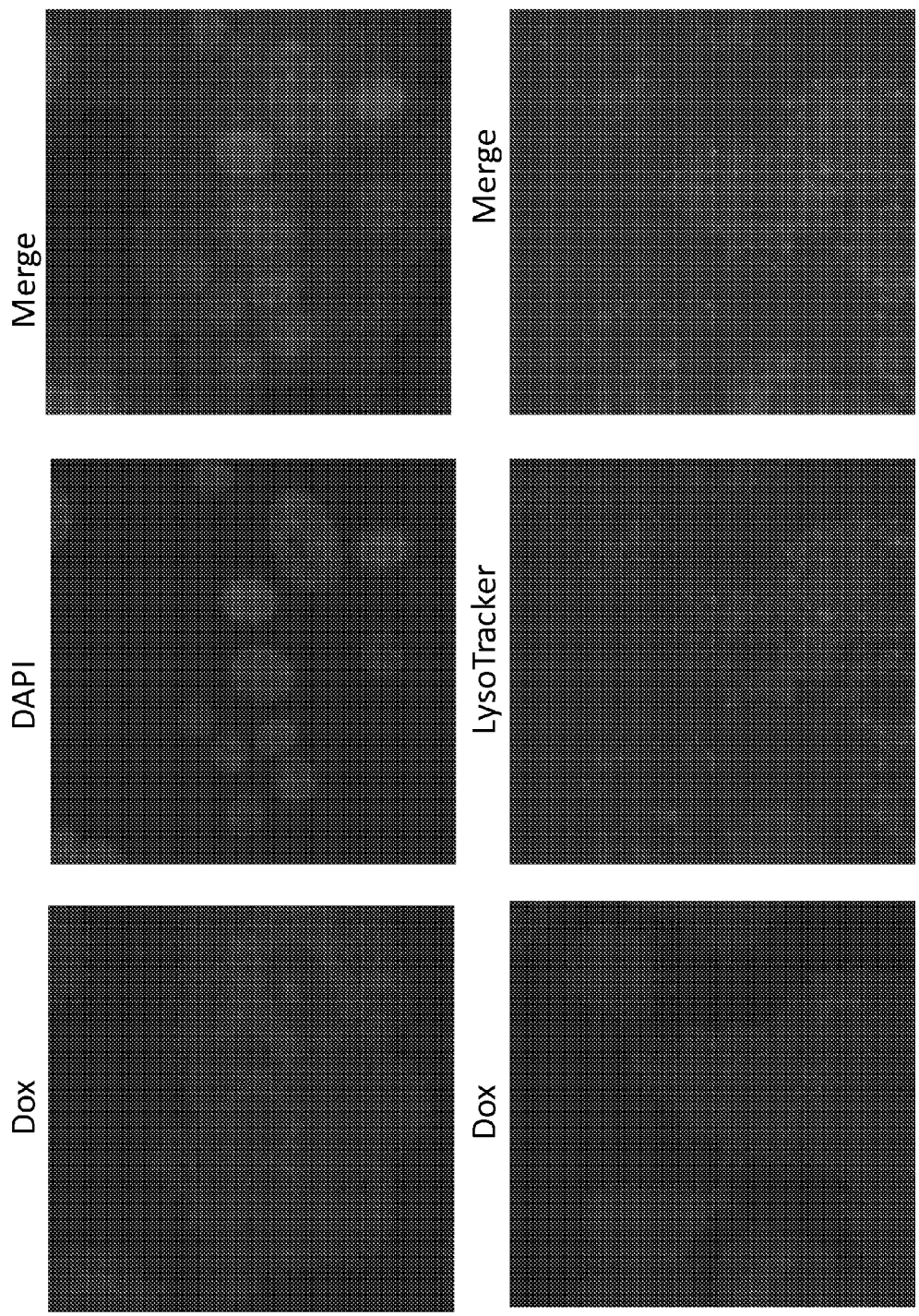
Figure 18-a

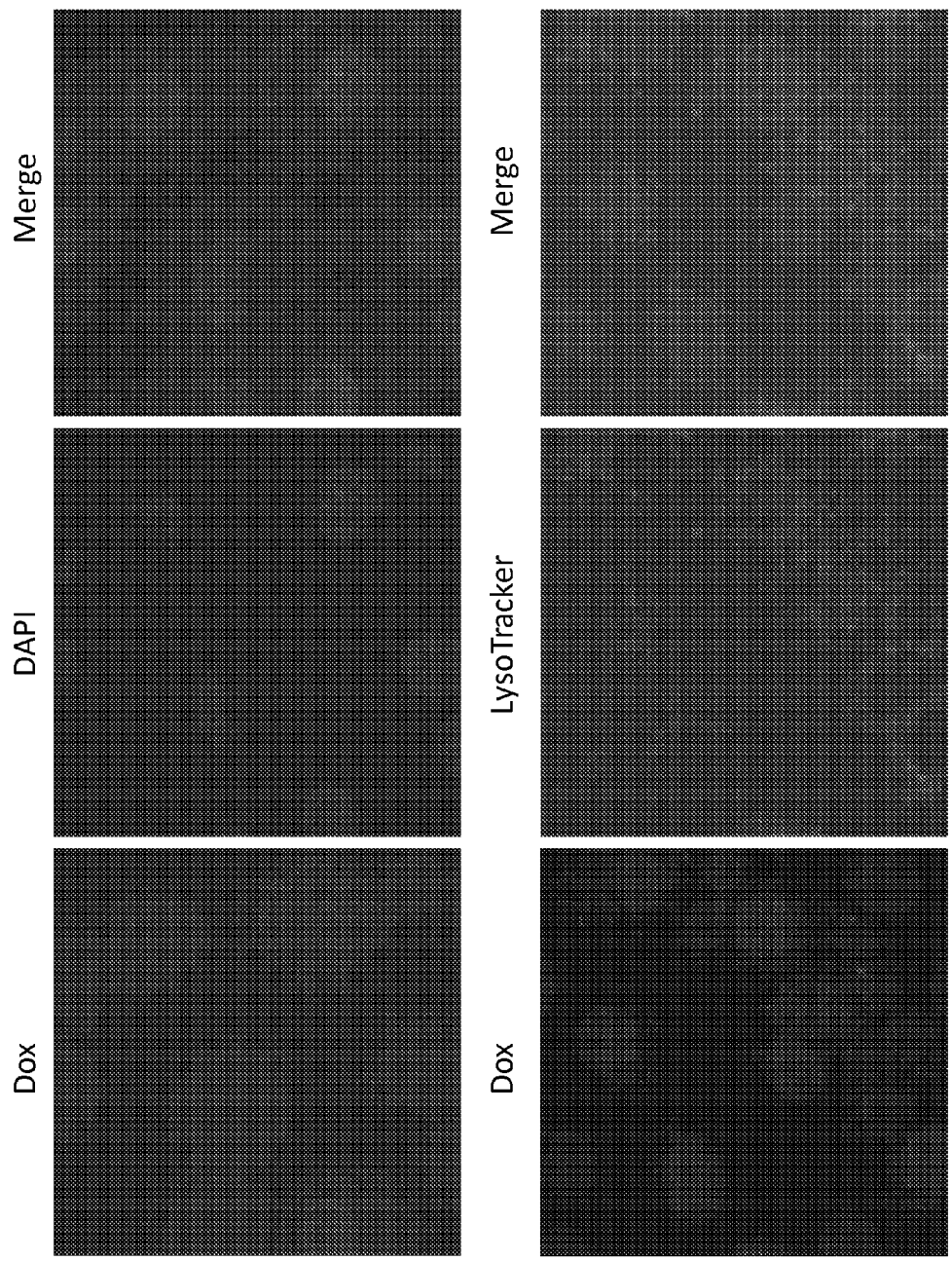
Figure 18-b

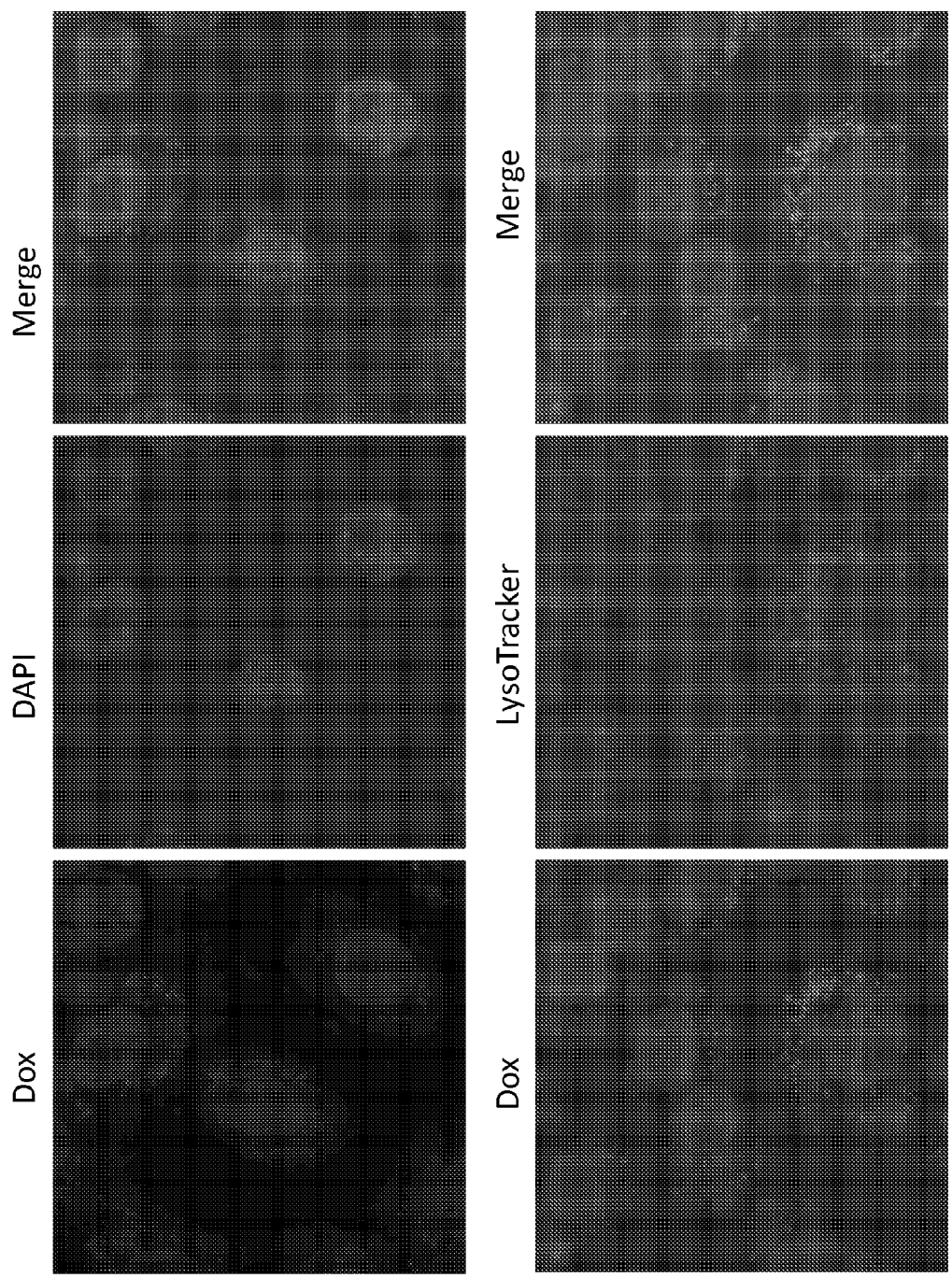
Figure 18-c

LOCALIZATION OF AGENTS AT A TARGET SITE WITH A COMPOSITION AND AN ENERGY SOURCE

CROSS REFERENCE TO RELATED APPLICATIONS

This application claims the benefit of PCT Application No. PCT/US/2011/026592, filed Mar. 1, 2011, which claims the benefit of U.S. Provisional Application No. 61/1309,374, filed Mar. 1, 2010, the entire disclosure of which is hereby incorporated by reference in its entirety for all purposes.

STATEMENT REGARDING FEDERALLY SPONSORED RESEARCH OR DEVELOPMENT

This invention was made with government support under CA103828 awarded by the National Institutes of Health. The government has certain rights in the invention.

BACKGROUND

Effective strategies for low-toxicity, multiply-administered cancer therapies are uncommonly reported[1]. Encapsulating doxorubicin into liposomes has increased the total tolerated dose[2-4], while cardiac toxicity, mucositis and palmar-plantar erythrodysesthesia restrict the maximum lifetime dose and limit the clinical dosing schedule to 10-12 mg/kg/week at intervals of two to six weeks[1,5,6]. Unexpected synergies between the cardiotoxicities of anthracyclines and growth factors such as anti-ErbB2 antibodies have further increased the need to reduce toxicity[7]. Given the impact of the dose limitations on efficacy, particles with reduced toxicity would facilitate treatment, particularly in recurrence.

To enhance stability of doxorubicin within the particle, we create a complex between the drug and a transition metal, as has previously been reported for doxorubicin with manganese (II) and irinotecan with copper (II)[8-10]. Creation of a copper-doxorubicin complex during the loading process is particularly attractive, since the formation of the copper (II)-doxorubicin complex has been associated with oxygen radical-mediated stimulation of DNA strand scission, the stimulation of lipid peroxidation mechanisms and resultant toxicities[11-13]. Formation of a drug-metal complex during loading changes the morphology of the liposomes and subsequently improves circulation lifetime and the accumulation of liposomes in tumors[14,15]. Further, a 1:2 complex of copper and doxorubicin with a stability constant of $10^{16}$ forms when a neutral pH is created within liposomes[16,17]. Yet, at a low pH, such as the pH encountered within a lysosome or tumor, the stable copper:doxorubicin ratio has been reported to change to 1:1 and the stability of the complex decreases[17]. Here, we track the liposome shell using positron emission tomography (PET) and the drug using multi-spectral fluorescence in order to assess the pharmacokinetics.

Further, the protective coating of liposomes reduces drug diffusion within the tumor, and the impact of liposomal therapy on clinical efficacy has been modest[18]. We address the dual issues of toxicity and efficacy by applying our stable particle in an aggressive dosing schedule and incorporating two strategies designed to enhance efficacy: mTOR inhibition to slow proliferation[19] and therapeutic ultrasound to enhance accumulation and local diffusion[20,21]. The aggressive syngeneic Met-1 model is known to be sensitive to rapamycin (which is an mTOR inhibitor); however, rapamycin alone is not curative in this model[22].

Ultrasound, as a source of thermal and mechanical energy can augment drug delivery by releasing the drug or increasing vascular permeability and thus particle accumulation and diffusion[20,21]. Tumor blood vessels present relatively permeable capillaries that allow macromolecules and small liposomes (100 nm) to leak through open gaps and fenestration due to the enhanced permeability and retention (EPR) effect[23,24]. Heating of the tumor rim, when combined with liposomal drugs, can enhance therapeutic efficacy as was previously demonstrated for radiofrequency (RF) ablation combined with liposomal doxorubicin[25]. Thus, by enhancing the pharmacokinetic profile and the extent of the EPR effect, we demonstrate enhanced efficacy and reduced toxicity in a highly aggressive mouse model of breast cancer[26,27].

SUMMARY

Described herein is a method for localized delivery of an agent to a target site, comprising: administering a composition to a subject, wherein the subject comprises the target site and the composition comprises an agent-transition metal complex; and irradiating the target site with an energy source, the irradiating causing accumulation of the agent-transition metal complex at the target site or release of the agent-transition metal complex from the composition at the target site, thereby producing localized delivery of the agent to the target site.

In some embodiments, the administered composition further comprises a liposome comprising a 63:7:25:5 molar ratio of DPPC:DSPC:chol:DSPE-PEG2k, wherein the liposome comprises the complex, wherein the agent is doxorubicin, wherein the transition metal is copper (II), wherein the energy source is ultrasound, wherein the target site comprises a tumor, and wherein the method further comprises administering rapamycin to the subject.

In some embodiments, the agent is an anthracycline. In some embodiments, the anthracycline is selected from the group consisting of: daunorubicin, doxorubicin, epirubicin, idarubicin, mitoxantrone, valrubicin, and irinotecan. In some embodiments, the agent is doxorubicin. In some embodiments, the transition metal is copper. In some embodiments, the molar ratio of doxorubicin to copper in the composition is 2:1. In some embodiments, the molar ratio of doxorubicin to copper in the composition is 1:1. In some embodiments, the doxorubicin concentration in the composition is less than 50 mM, 50 to 100 mM, 100 to 150 mM, 150 to 200 mM, 200 to 250 mM, 250 to 300 mM, 300 to 350 mM, or greater than 350 mM. In some embodiments, the doxorubicin concentration in the composition is 200 mM.

In some embodiments, the composition further comprises a liposome, a micelle, a polymersome, or a nanoparticle. In some embodiments, the composition further comprises a liposome, and wherein the liposome comprises the complex. In some embodiments, the liposome is a long circulating liposome (LCL). In some embodiments, the liposome comprises L-α-phosphatidylcholine, hydrogenated soy (HSPC): cholesterol (chol):1,2 distearoyl-sn-glycero-3-phosphoethanolamine-N-Methoxy polyethyleneglycol-2000 (DSPE-PEG2k). In some embodiments, the molar ratio of HSPC:chol:DSPE-PEG2k is 56:39:5, respectively. In some embodiments, the liposome is a temperature-sensitive liposome (TSL). In some embodiments, the TSL comprises 1,2-dipalmitoyl-sn-glycero-3-phospho-choline (DPPC):1,2-distearoyl-sn-glycero-3-phosphocholine (DSPC):DSPE- PEG2k. In some embodiments, the molar ratio of DPPC:DSPC:DSPE-PEG2k is 85.5:9.5:5, respectively. In some embodiments, the TSL comprises DPPC:DSPC:chol:DSPE-PEG2k. In some embodiments, the molar ratio of DPPC:DSPC:chol:DSPE-PEG2k is 63:7:25:5, respectively. In some embodiments, the TSL comprises DPPC:1-palmitoyl-2-hydroxy-sn-glycero-3-phosphocholine (MPPC):DSPE-PEG2k. In some embodiments, the molar ratio of DPPC:MPPC:DSPE-PEG2k is 86:10:4, respectively.

In some embodiments, the composition further comprises a TSL and a LCL. In some embodiments, the TSL and the LCL are administered simultaneously. In some embodiments, the TSL is administered before the LCL is administered. In some embodiments, the LCL is administered before the TSL is administered. In some embodiments, the TSL comprises DPPC:DSPC:DSPE-PEG2k, DPPC:DSPC:chol:DSPE-PEG2k, or DPPC:MPPC:DSPE-PEG2k. In some embodiments, the LCL comprises HSPC:chol:DSPE-PEG2k.

In some embodiments, the transition metal is manganese or iron. In some embodiments, the transition metal is copper. In some embodiments, the transition metal is copper (II). In some embodiments, the copper (II) is associated with a gluconate counter-ion.

In some embodiments, the energy source is an ultrasound source, a microwave source, a radiofrequency energy source, or an infrared source. In some embodiments, the energy source is an ultrasound source. In some embodiments, the ultrasound source is programmed to deliver at least 100-cycle bursts at 0.5 to 10 MHz center frequency with a variable pulse-repetition frequency (PRF) ranging from 100 Hz to continuous wave ultrasound and a variable peak transmitter voltage ranging from 0 to 24.5 V. In some embodiments, the irradiating with the ultrasound source results in increased blood flow in the target site. In some embodiments, the irradiating with the ultrasound source results in increased blood flow and permeability of liposomes across endothelial cells in the target site, and wherein the irradiating with the ultrasound source triggers the release of encapsulated agent from a temperature-sensitive liposome comprising the complex.

In some embodiments, a method further comprises repeating the step of administering the composition. In some embodiments, a method further comprises repeating the step of irradiating the target site with the energy source. In some embodiments, a method further comprises releasing the complex from the composition at the target site.

In some embodiments, a method further comprises administering a second agent to the subject. In some embodiments, the second agent comprises a mammalian target of rapamycin (mTOR) inhibitor. In some embodiments, the second agent is rapamycin. In some embodiments, the second agent is Temsirolimus, Epigallocatechin gallate (EGCG), caffeine, curcumin, or resveratrol. In some embodiments, a method further comprises repeating the step of administering the second agent. In some embodiments, the second agent is co-administered with the complex. In some embodiments, the second agent is administered via intraperitoneal injection and wherein the complex is administered via intravenous injection. In some embodiments, the second agent and the complex are administered simultaneously.

In some embodiments, the target site comprises a tumor. In some embodiments, the subject is need of disease treatment. In some embodiments, the disease is cancer.

In some embodiments, a method described above is less toxic than a second method for localized delivery of the agent to the target site, the second method comprising: administering a second composition to a control subject, wherein the control subject comprises the target site and the second composition does not comprise a transition metal; and irradiating the target site with the energy source, the irradiating causing accumulation of the agent at the target site, thereby producing localized delivery of the agent to the target site. In some embodiments, the agent of the second method comprises doxorubicin HCl and wherein the second composition comprises a liposome consisting of N-(carbonyl-methoxypolyethylene glycol 2000)-1,2-distearoyl-sn-glycero3-phosphoethanolamine sodium salt (DSPE-PEG2k) at a concentration of 3.19 mg/mL; fully hydrogenated soy phosphatidylcholine (HSPC) at a concentration of 9.58 mg/mL; and cholesterol at a concentration of 3.19 mg/mL, and wherein the liposome comprises the agent. In some embodiments, the toxicity of the second method is about six-fold higher than the toxicity of a method described above.

In some embodiments, the method does not cause substantial hair loss, a substantial skin rash, or substantial irritation in the subject.

Also described herein is a method of treating a tumor, in a subject in need thereof, comprising: administering a composition to the subject, wherein the composition comprises an agent-transition metal complex, and the subject comprises a tumor; applying an energy source to the tumor; and accumulating the composition in the tumor, thereby treating the tumor.

In some embodiments, the administered composition further comprises a liposome comprising a 63:7:25:5 molar ratio of DPPC:DSPC:chol:DSPE-PEG2k, wherein the liposome comprises the complex, wherein the agent is doxorubicin, wherein the transition metal is copper (II), wherein the energy source is ultrasound, and wherein the method further comprises administering rapamycin to the subject.

In some embodiments, the agent is an anthracycline. In some embodiments, the anthracycline is selected from the group consisting of: daunorubicin, doxorubicin, epirubicin, idarubicin, mitoxantrone, valrubicin, and irinotecan. In some embodiments, the agent is doxorubicin. In some embodiments, the transition metal is copper. In some embodiments, the molar ratio of doxorubicin to copper in the composition is 2:1. In some embodiments, the molar ratio of doxorubicin to copper in the composition is 1:1. In some embodiments, the doxorubicin concentration in the composition is less than 50 mM, 50 to 100 mM, 100 to 150 mM, 150 to 200 mM, 200 to 250 mM, 250 to 300 mM, 300 to 350 mM, or greater than 350 mM. In some embodiments, the doxorubicin concentration in the composition is 200 mM.

In some embodiments, the composition further comprises a liposome, a micelle, a polymersome, or a nanoparticle. In some embodiments, the composition further comprises a liposome, and wherein the liposome comprises the complex. In some embodiments, the liposome is a long circulating liposome (LCL). In some embodiments, the liposome comprises L-α-phosphatidylcholine, hydrogenated soy (HSPC):cholesterol (chol):1,2 distearoyl-sn-glycero-3-phosphoethanolamine-N-Methoxy polyethyleneglycol-2000 (DSPE-PEG2k). In some embodiments, the molar ratio of HSPC:chol:DSPE-PEG2k is 56:39:5, respectively. In some embodiments, the liposome is a temperature-sensitive liposome (TSL). In some embodiments, the TSL comprises 1,2-dipalmitoyl-sn-glycero-3-phospho-choline (DPPC):1,2-distearoyl-sn-glycero-3-phosphocholine (DSPC):DSPE-PEG2k. In some embodiments, the molar ratio of DPPC:DSPC:DSPE-PEG2k is 85.5:9.5:5, respectively. In some embodiments, the TSL comprises DPPC:DSPC:chol:DSPE-PEG2k. In some embodiments, the molar ratio of DPPC:DSPC:chol:DSPE-PEG2k is 63:7:25:5, respectively. In some embodiments, the TSL comprises DPPC:1-palmitoyl-2-hydroxy-sn-glycero-3-phosphocholine (MPPC):DSPE-PEG2k. In some embodiments, the molar ratio of DPPC:MPPC:DSPE-PEG2k is 86:10:4, respectively.

In some embodiments, the composition further comprises a TSL and a LCL. In some embodiments, the TSL and the LCL are administered simultaneously. In some embodiments, the TSL is administered before the LCL is administered. In some embodiments, the LCL is administered before the TSL is administered. In some embodiments, the TSL comprises DPPC:DSPC:DSPE-PEG2k, DPPC:DSPC:chol:DSPE-PEG2k, or DPPC:MPPC:DSPE-PEG2k. In some embodiments, the LCL comprises HSPC:chol:DSPE-PEG2k.

In some embodiments, the transition metal is manganese or iron. In some embodiments, the transition metal is copper. In some embodiments, the transition metal is copper (II). In some embodiments, the copper (II) is associated with a gluconate counter-ion.

In some embodiments, the energy source is an ultrasound source, a microwave source, a radiofrequency energy source, or an infrared source. In some embodiments, the energy source is an ultrasound source. In some embodiments, the ultrasound source is programmed to deliver at least 100-cycle bursts at 0.5 to 10 MHz center frequency with a variable pulse-repetition frequency (PRF) ranging from 100 Hz to continuous wave ultrasound and a variable peak transmitter voltage ranging from 0 to 24.5 V. In some embodiments, the irradiating with the ultrasound source results in increased blood flow in the target site. In some embodiments, the irradiating with the ultrasound source results in increased blood flow and permeability of liposomes across endothelial cells in the target site, and wherein the irradiating with the ultrasound source triggers the release of encapsulated agent from a temperature-sensitive liposome comprising the complex.

In some embodiments, a method further comprises repeating the step of administering the composition. In some embodiments, a method further comprises repeating the step of irradiating the target site with the energy source. In some embodiments, a method further comprises releasing the complex from the composition at the target site.

In some embodiments, a method further comprises administering a second agent to the subject. In some embodiments, the second agent comprises a mammalian target of rapamycin (mTOR) inhibitor. In some embodiments, the second agent is rapamycin. In some embodiments, the second agent is Temsirolimus, Epigallocatechin gallate (EGCG), caffeine, curcumin, or resveratrol. In some embodiments, a method further comprises repeating the step of administering the second agent. In some embodiments, the second agent is co-administered with the complex. In some embodiments, the second agent is administered via intraperitoneal injection and wherein the complex is administered via intravenous injection. In some embodiments, the second agent and the complex are administered simultaneously.

In some embodiments, a method described above is less toxic than a second method for localized delivery of the agent to the target site, the second method comprising: administering a second composition to a control subject, wherein the control subject comprises the target site and the second composition does not comprise a transition metal; and irradiating the target site with the energy source, the irradiating causing accumulation of the agent at the target site, thereby producing localized delivery of the agent to the target site. In some embodiments, the agent of the second method comprises doxorubicin HCl and wherein the second composition comprises a liposome consisting of N-(carbonyl-methoxypolyethylene glycol 2000)-1,2-distearoyl-sn-glycero3-phosphoethanolamine sodium salt (DSPE-PEG2k) at a concentration of 3.19 mg/mL; fully hydrogenated soy phosphatidylcholine (HSPC) at a concentration of 9.58 mg/mL; and cholesterol at a concentration of 3.19 mg/mL, and wherein the liposome comprises the agent. In some embodiments, the toxicity of the second method is about six-fold higher than the toxicity of a method described above.

In some embodiments, the method does not cause substantial hair loss, a substantial skin rash, or substantial irritation in the subject.

Also described herein is a method for localized delivery of an agent to a tumor target site, comprising: administering a composition to a subject, wherein the subject comprises the tumor target site and the composition comprises agent-transition metal complex; and irradiating the tumor target site with an energy source, the irradiating causing accumulation of the complex at the tumor target site, thereby producing localized delivery of agent to the tumor target site.

In some embodiments, the administered composition further comprises a liposome comprising a 63:7:25:5 molar ratio of DPPC:DSPC:chol:DSPE-PEG2k, wherein the liposome comprises the complex, wherein the agent is doxorubicin, wherein the transition metal is copper (II), wherein the energy source is ultrasound, and wherein the method further comprises administering rapamycin to the subject.

In some embodiments, the agent is an anthracycline. In some embodiments, the anthracycline is selected from the group consisting of: daunorubicin, doxorubicin, epirubicin, idarubicin, mitoxantrone, valrubicin, and irinotecan. In some embodiments, the agent is doxorubicin. In some embodiments, the transition metal is copper. In some embodiments, the molar ratio of doxorubicin to copper in the composition is 2:1. In some embodiments, the molar ratio of doxorubicin to copper in the composition is 1:1. In some embodiments, the doxorubicin concentration in the composition is less than 50 mM, 50 to 100 mM, 100 to 150 mM, 150 to 200 mM, 200 to 250 mM, 250 to 300 mM, 300 to 350 mM, or greater than 350 mM. In some embodiments, the doxorubicin concentration in the composition is 200 mM.

In some embodiments, the composition further comprises a liposome, a micelle, a polymersome, or a nanoparticle. In some embodiments, the composition further comprises a liposome, and wherein the liposome comprises the complex. In some embodiments, the liposome is a long circulating liposome (LCL). In some embodiments, the liposome comprises L-α-phosphatidylcholine, hydrogenated soy (HSPC):cholesterol (chol):1,2 distearoyl-sn-glycero-3-phosphoethanolamine-N-Methoxy polyethyleneglycol-2000 (DSPE-PEG2k). In some embodiments, the molar ratio of HSPC:chol:DSPE-PEG2k is 56:39:5, respectively. In some embodiments, the liposome is a temperature-sensitive liposome (TSL). In some embodiments, the TSL comprises 1,2-dipalmitoyl-sn-glycero-3-phospho-choline (DPPC):1,2-distearoyl-sn-glycero-3-phosphocholine (DSPC):DSPE-PEG2k. In some embodiments, the molar ratio of DPPC:DSPC:DSPE-PEG2k is 85.5:9.5:5, respectively. In some embodiments, the TSL comprises DPPC:DSPC:chol:DSPE-PEG2k. In some embodiments, the molar ratio of DPPC:DSPC:chol:DSPE-PEG2k is 63:7:25:5, respectively. In some embodiments, the TSL comprises DPPC:1-palmitoyl-2-hydroxy-sn-glycero-3-phosphocholine (MPPC):DSPE-PEG2k. In some embodiments, the molar ratio of DPPC:MPPC:DSPE-PEG2k is 86:10:4, respectively.

In some embodiments, the composition further comprises a TSL and a LCL. In some embodiments, the TSL and the LCL are administered simultaneously. In some embodiments, the TSL is administered before the LCL is administered. In some embodiments, the LCL is administered before the TSL is administered. In some embodiments, the TSL comprises DPPC:DSPC:DSPE-PEG2k, DPPC:DSPC:chol:DSPE-PEG2k, or DPPC:MPPC:DSPE-PEG2k. In some embodiments, the LCL comprises HSPC:chol:DSPE-PEG2k.

In some embodiments, the transition metal is manganese or iron. In some embodiments, the transition metal is copper. In some embodiments, the transition metal is copper (II). In some embodiments, the copper (II) is associated with a gluconate counter-ion.

In some embodiments, the energy source is an ultrasound source, a microwave source, a radiofrequency energy source, or an infrared source. In some embodiments, the energy source is an ultrasound source. In some embodiments, the ultrasound source is programmed to deliver at least 100-cycle bursts at 0.5 to 10 MHz center frequency with a variable pulse-repetition frequency (PRF) ranging from 100 Hz to continuous wave ultrasound and a variable peak transmitter voltage ranging from 0 to 24.5 V. In some embodiments, the irradiating with the ultrasound source results in increased blood flow in the target site. In some embodiments, the irradiating with the ultrasound source results in increased blood flow and permeability of liposomes across endothelial cells in the target site, and wherein the irradiating with the ultrasound source triggers the release of encapsulated agent from a temperature-sensitive liposome comprising the complex.

In some embodiments, a method further comprises repeating the step of administering the composition. In some embodiments, a method further comprises repeating the step of irradiating the target site with the energy source. In some embodiments, a method further comprises releasing the complex from the composition at the target site.

In some embodiments, a method further comprises administering a second agent to the subject. In some embodiments, the second agent comprises a mammalian target of rapamycin (mTOR) inhibitor. In some embodiments, the second agent is rapamycin. In some embodiments, the second agent is Temsirolimus, Epigallocatechin gallate (EGCG), caffeine, curcumin, or resveratrol. In some embodiments, a method further comprises repeating the step of administering the second agent. In some embodiments, the second agent is co-administered with the complex. In some embodiments, the second agent is administered via intraperitoneal injection and wherein the complex is administered via intravenous injection. In some embodiments, the second agent and the complex are administered simultaneously.

In some embodiments, a method described above is less toxic than a second method for localized delivery of the agent to the target site, the second method comprising: administering a second composition to a control subject, wherein the control subject comprises the target site and the second composition does not comprise a transition metal; and irradiating the target site with the energy source, the irradiating causing accumulation of the agent at the target site, thereby producing localized delivery of the agent to the target site. In some embodiments, the agent of the second method comprises doxorubicin HCl and wherein the second composition comprises a liposome consisting of N-(carbonyl-methoxypolyethylene glycol 2000)-1,2-distearoyl-sn-glycero3-phosphoethanolamine sodium salt (DSPE-PEG2k) at a concentration of 3.19 mg/mL; fully hydrogenated soy phosphatidylcholine (HSPC) at a concentration of 9.58 mg/mL; and cholesterol at a concentration of 3.19 mg/mL, and wherein the liposome comprises the agent. In some embodiments, the toxicity of the second method is about six-fold higher than the toxicity of a method described above.

In some embodiments, the method does not cause substantial hair loss, a substantial skin rash, or substantial irritation in the subject.

Also described herein is a composition, comprising: a carrier and a crystal comprising a crystalline agent-transition metal complex. In some embodiments, the agent is an anthracycline. In some embodiments, the anthracycline is selected from the group consisting of: daunorubicin, doxorubicin, epirubicin, idarubicin, mitoxantrone, valrubicin, and irinotecan. In some embodiments, the anthracycline is doxorubicin.

In some embodiments, the transition metal is copper.

In some embodiments, said crystal comprising said crystalline complex has a dimension of from 0.1 nm to 50 nm. In some embodiments, said crystalline complex comprises a 2:1 molar ratio of agent:transition metal. In some embodiments, said crystalline complex comprises a 1:1 molar ratio of agent:transition metal. In some embodiments, said crystal comprising said crystalline complex is insoluble in a buffered salt solution at pH 7.4 and 37° C. In some embodiments, said crystal comprising said crystalline complex is soluble in a buffered salt solution at pH 5.0 and 37° C.

In some embodiments, said carrier is selected from the group consisting of a liposome, a micelle, and a polymersome. In some embodiments, said carrier is a liposome. In some embodiments, said liposome comprises DPPC, DSPC, cholesterol, and DSPE-PEG2k. In some embodiments, said DPPC, DSPC, cholesterol, and DSPE-PEG2k are present in a 63:7:25:5 molar ratio.

Also described herein is a method of producing an agent-transition metal crystalline complex in a liposome, comprising: preparing the liposome in the presence of a transition metal; creating a triethanolamine (TEA) gradient across the membrane of the liposome at neutral pH; incubating the liposome in the presence of an agent; and allowing the agent-transition metal crystalline complex to form in the liposome.

In some embodiments, the agent is an anthracycline. In some embodiments, the anthracycline is selected from the group consisting of: daunorubicin, doxorubicin, epirubicin, idarubicin, mitoxantrone, valrubicin, and irinotecan. In some embodiments, the anthracycline is doxorubicin. In some embodiments, the transition metal is copper. In some embodiments, the agent is doxorubicin, wherein the transition metal is copper, wherein the liposome is prepared in the presence of 100 mM copper, wherein the TEA gradient is 90-270 mM and the pH is 7.4, and wherein the liposome is incubated in the presence of 2 mg/ml doxorubicin.

Also described herein is a method of producing an agent-transition metal crystalline complex in a liposome, comprising: acquiring a liposome comprising a transition metal; creating a TEA gradient across the membrane of the liposome at neutral pH; incubating the liposome in the presence of an agent; and allowing the agent-transition metal crystalline complex to form in the liposome.

In some embodiments, the agent is an anthracycline. In some embodiments, the anthracycline is selected from the group consisting of: daunorubicin, doxorubicin, epirubicin, idarubicin, mitoxantrone, valrubicin, and irinotecan. In some embodiments, the anthracycline is doxorubicin. In some embodiments, the transition metal is copper. In some embodiments, the agent is doxorubicin, wherein the transition metal is copper, wherein the liposome comprises 100 mM copper, wherein the TEA gradient is 90-270 mM and the pH is 7.4, and wherein the liposome is incubated in the presence of 2 mg/ml doxorubicin.

BRIEF DESCRIPTION OF THE SEVERAL VIEWS OF THE DRAWINGS

These and other features, aspects, and advantages will become better understood with regard to the following description, and accompanying drawings, where:

FIG. 18. Subcellular localization of doxorubicin from liposomal copper-doxorubicin in temperature-sensitive liposomes trafficking in NDL cells using nucleus and lysosome staining Liposomal copper-doxorubicin in lyso-temperature-sensitive liposomes (CuDox-LTSLs) was incubated with NDL cells on ice for 30 min. Cells were then rinsed with cold media and incubated at 37° C. After 30 min (a), 5 h (b), and 24 h (c) cells were stained with DAPI to stain nucleus and with LysoTracker-blue to stain lysosomes. Images of subcellular localization of doxorubicin, DAPI or LysoTracker-blue (middle panels) were captured and merged to demonstrate co-localization of Dox with either DAPI or LysoTracker-blue (far right panels). This figure shows that CuDox liposomes traffic through the liposomes and that doxorubicin reaches the nucleus in a manner that is similar to free doxorubicin.

DETAILED DESCRIPTION

Figure 1:
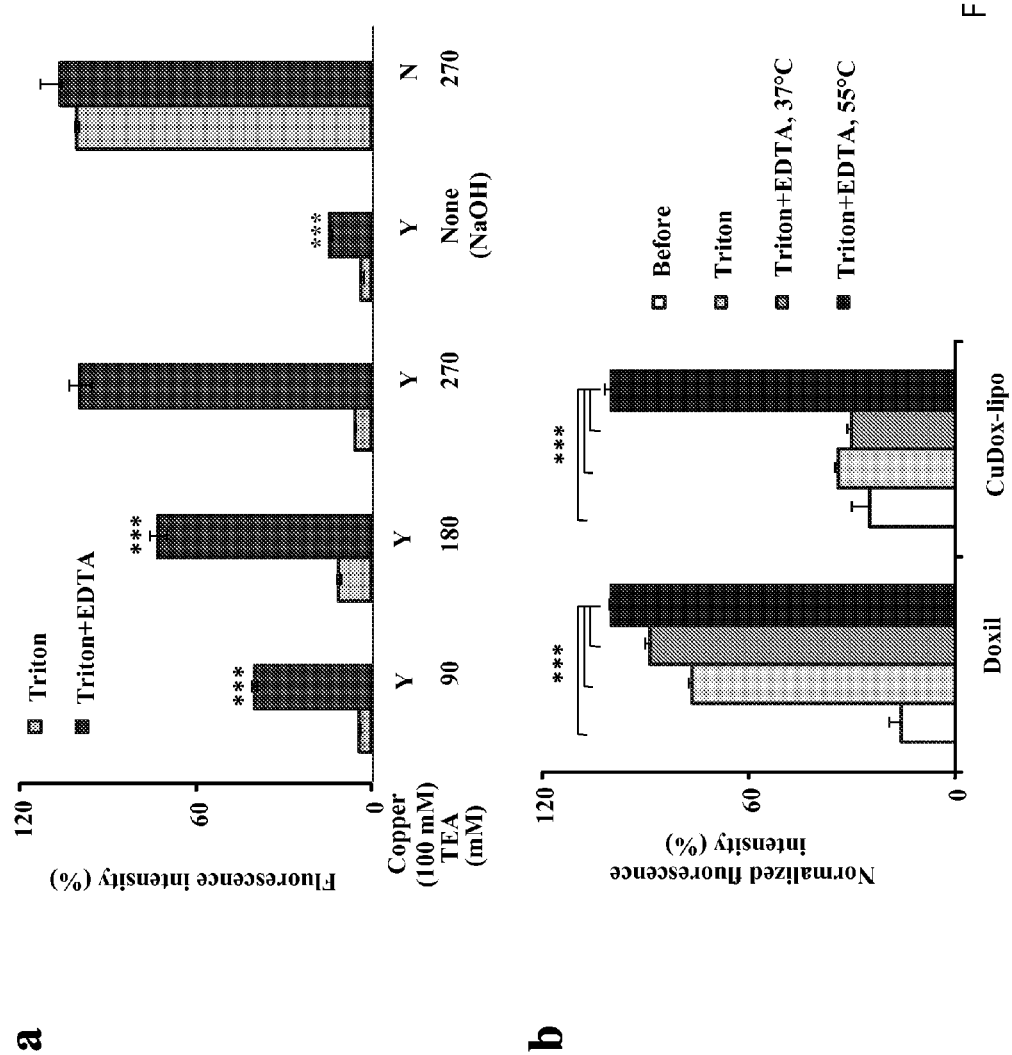
FIG. 1. Loading optimization and in vitro characterization of copper-doxorubicin in long-circulating liposomes (LCLs). a, Fluorescence intensity of doxorubicin encapsulated in LCLs with an increasing TEA gradient, released by Triton X-100 in the presence or absence of 10 mM EDTA. b, Effect of EDTA and heat in trans-chelation of doxorubicin from copper, as assessed by fluorescence. Copper-doxorubicin (CuDox) liposomes and Doxil were incubated in complement-preserved human serum in the presence or absence of 0.25% Triton X-100 for 1 hour. c, Fluorescence images of plasma isolated from mice 24 h post injection of either Doxil or CuDox liposomes, before and after the addition of TritonX-100 at 37° C. or TritonX-100 with 10 mM EDTA at 55° C. for 1 h. d, Dissociation of copper from CuDox complex in 0.5 mM BSA solutions as a function of pH at 37° C. Statistical analyses were performed using one-way ANOVA followed by a Tukey Post Hoc test. ***, †p<0.001.
Figure 1:
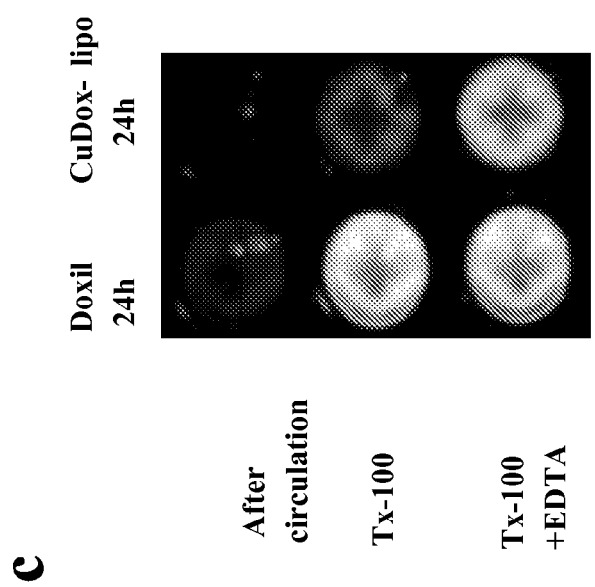

Terms used in the claims and specification are defined as set forth below unless otherwise specified.

The term "ameliorating" refers to any therapeutically beneficial result in the treatment of a disease state, e.g., a cancerous disease state, including prophylaxis, lessening in the severity or progression, remission, or cure thereof.

The term "in situ" refers to processes that occur in a living cell growing separate from a living organism, e.g., growing in tissue culture.

The term "in vivo" refers to processes that occur in a living organism.

The term "mammal" as used herein includes both humans and non-humans and include but is not limited to humans, non-human primates, canines, felines, murines, bovines, equines, and porcines.

The term "sufficient amount" means an amount sufficient to produce a desired effect, e.g., an amount sufficient to modulate protein aggregation in a cell.

The term "therapeutically effective amount" is an amount that is effective to ameliorate a symptom of a disease. A therapeutically effective amount can be a "prophylactically effective amount" as prophylaxis can be considered therapy.

The phrase "administering into a vessel" encompasses direct and remote administration (i.e., directly into the vessel and into a vessel that is in fluidic communication with a vessel into which agent has been directly administered).

The term "vasoporation" refers to either a mechanical increase in vascular permeability secondary to insonation with an ultrasound wave or a chemical increase in vascular permeability achieved locally by using an ultrasound wave.

The term "carrier" refers to a discrete, particulate molecular structure able to associate with, carry, and ultimately deliver an agent to a target.

The term "long circulating liposome" or "LCL" refers to liposomal formulations having high percentages (e.g., >15%, >20%, >25%, or >30%) of cholesterol. Cholesterol generally acts to enhance the plasma stability and the circulation half-life of the LCLs compared to non-cholesterol or low-cholesterol containing liposomal formulations.

The term "temperature-sensitive liposome" or "TSL" refers to liposomal formulations having relatively lower phase-transition temperatures (e.g., 40-45° C.) and cholesterol content (compared to control liposomal formulations) and that release their contents at the phase-transition temperature of the liposomes upon application of an energy source to the liposomes.

It must be noted that, as used in the specification and the appended claims, the singular forms "a," "an" and "the" include plural referents unless the context clearly dictates otherwise.

Compositions and Carriers

In some embodiments, a composition can include carriers associated with agents. Carriers useful in a composition can include, but are not limited to: Apo-E lipoprotein particles, dendrimers, metal core particles, biodegradable polymers; phage; retroviruses; adenoviruses; adeno-associated viruses and other viruses; cells; liposomes; temperature-sensitive liposomes (TSLs); phospholipid-based liposomes; polymeric matrices; lipid formulations; phospholipid-based formulations; micelles; fatty acid formulations; microbubbles; nanoparticles; caveolae; non-polymeric matrices or carriers such as, e.g., gold carriers; microdevices; nanodevices; and nano-scale semiconductor materials.

In one embodiment, the use of lipid formulations of carriers, e.g., liposomes, is contemplated for the introduction of an agent to a subject. Agents of are described in more detail below. In one embodiment, an agent is associated with a carrier. In an embodiment, the agent can be associated with, linked to, inserted into, carried by, or attached to a membrane, outer surface, lipid, or lipid membrane of the carrier. In other embodiments, the agent associated with a lipid of the carrier can be attached to a liposome via a linking molecule that is associated with both the liposome and the carrier.

Lipids are fatty substances which can be obtained from naturally-occurring or synthetic sources. For example, lipids include the fatty droplets that naturally occur in the cytoplasm as well as the class of agents which are well known to those of skill in the art that contain long-chain aliphatic hydrocarbons and their derivatives, such as phospholipids, fatty acids, alcohols, amines, amino alcohols, and aldehydes. Additional examples of suitable lipids include hydrogenated lecithin from plants and animals, such as egg yolk lecithin and soybean lecithin. The lipid can also be phosphatidyl choline produced from partial or complete synthesis containing mixed acyl groups of lauryl, myristoyl, palmitoyl and stearoyl. Lipids can include, e.g., 1,2-Dipalmitoyl-sn-glycero-3phosphocholine (DPPC).

"Liposome" is a generic term encompassing a variety of single and multilamellar lipid carriers formed by the generation of enclosed lipid bilayers or aggregates. Liposomes can be characterized as having vesicular structures with a phospholipid bilayer membrane and an inner aqueous medium. Multilamellar liposomes can have multiple lipid layers separated by aqueous medium. Typically, they form spontaneously when phospholipids are suspended in an excess of aqueous solution. The lipid components typically undergo self-rearrangement before the formation of closed structures and entrap water and dissolved solutes between the lipid layers. However, in one embodiment, the invention can also encompass compositions that have different structures in solution than the normal vesicular structure. For example, the lipids can assume a micellar structure or merely exist as nonuniform aggregates of lipid molecules. Also contemplated are lipofectamine-agent complexes. The liposome is one embodiment of a carrier.

A neutral lipid can comprise a lipid with no charge, a substantially uncharged lipid, or a lipid mixture with equal number of positive and negative charges. Suitable phospholipids include phosphatidyl cholines and others that are well known to those of skill in the art.

In one embodiment, phospholipids can be used for preparing liposomes and can carry a net positive, negative, or neutral charge. For example, diacetyl phosphate can be employed to confer a negative charge on the liposomes, and stearylamine can be used to confer a positive charge on the liposomes. The liposomes can typically be made of one or more phospholipids.

Phospholipids can form a variety of structures other than liposomes when dispersed in water, depending on the molar ratio of lipid to water. The physical characteristics of liposomes depend on pH, ionic strength, and/or the presence of divalent cations. Liposomes can show low permeability to ionic and/or polar substances, but at elevated temperatures undergo a "phase transition" which markedly alters their permeability. The phase transition involves a change from a closely-packed, ordered structure, known as the gel phase, to a loosely-packed, less-ordered structure, known as the fluid phase. This occurs at a characteristic phase-transition temperature, such as e.g., 37-45° C., and/or results in an increase in permeability to ions, sugars, and/or drugs. The gel phase is an ordered arrangement of the phospholipids, where the fatty acid chains are locked in staggered conformations, which result in minimal interactions of distinct phospholipids in a membrane. The fluid phase is characterized by a random arrangement of the phospholipids in a membrane. The different factors that influence a particular lipid's transition temperature can include, e.g., the number of carbons in the fatty acid chains, the number, position, and configuration of double bonds present, type of head-group present, and the overall charge of the molecule.

Phospholipids are known to have different phase transition temperatures and can be used to produce liposomes having release temperatures corresponding to the phase transition temperature of the phospholipids. Suitable phospholipids include, for example, dimyristoylphosphatidyl choline having a phase transition temperature of 23.9° C., palmitoylmyristoylphosphatidyl choline having a phase transition temperature of 27.2° C., myristolypalmitoylphosphatidyl choline having a phase transition temperature of 35.3° C., dipalmitoylphosphatidyl choline having a phase transition temperature of 41.4° C., stearoylpalmitoylphosphatidyl choline having a phase transition temperature of 44.0° C., palmitoylstearolyphosphatidyl choline having a phase transition of 47.4° C., and distearolyphosphatidyl choline having a phase transition temperature of 54.9° C. Another suitable phospholipid is a synthetic $C_{17}$ phosphatidyl choline from Avanti Polar Lipids Inc. having a phase transition temperature of about 48-49° C.

The phase transition temperature of the liposomes can be selected by combining the different phospholipids during the production of the liposomes according to the respective phase transition temperature. The phase transition of the resulting liposome membrane is generally proportional to the ratio by weight of the individual phospholipids. Thus, the composition of the phospholipids is selected based on the respective phase transition temperature so that the phase transition temperature of the liposome membrane will fall within the selected range. By adjusting the phase transition temperature of the liposome membrane to the selected range, the temperature at which the liposomes release the agents can be controlled during heating.

In one embodiment, the phase transition temperature can range from 38° C. to 80° C., depending on the molecular composition of the carrier. The phase transition temperature can range from 38° C. to 50° C. The phase transition temperature can range from 39° C. to 45° C. The phase transition temperature can be 42° C. The phase transition temperature can be 38, 39, 40, 41, 42, 43, 44, or 45° C.

In another embodiment, the composition contains a mixture of liposomes having different phase transition temperatures to release the agents at different temperatures. In one embodiment, the liposome composition contains liposomes coupled to a first agent and having a phase transition temperature of 42° C. to about 45° C. and liposomes coupled to a second agent and having a phase transition temperature of about 50° C. or higher. In one embodiment, the second agent is coupled to a liposome that releases the agent at a temperature range of 50° C. to 60° C. In this embodiment, the liposome composition is delivered to the target and the target site is subjected to hyperthermal (i.e., above normally-occurring) temperatures. As the tissue in the target site is heated to at least 42° C., the first liposomes release the first agent. In other embodiments, the hyperthermal treatment does not exceed a temperature sufficient to cause protein denaturization. In this embodiment, the second liposomes are selected to release the second agent at or slightly below the protein denaturization temperature. This embodiment allows a user to release a combination of drugs at a target site in a subject.

In another embodiment, the composition can contain several liposomes that can transition at different temperatures to release a plurality of agents at incremental temperatures as the temperature of the target site increases. In one embodiment, the liposomes can be selected to release agents at 2° C. intervals between about 42° C. and 50° C. The agents for each liposome can be different.

The compositions are not limited to any particular structure in solution prior to administration to a subject. For example, they can be present in a bilayer structure, such as a liposome; as micelles, or with a collapsed structure. They can also simply be interspersed in a solution, possibly forming aggregates which are not uniform in either size or shape.

It should be appreciated that membrane-forming material of a liposome can be any lipid or fatty acid comprising material. Exemplary materials which may form a membrane include, but are not limited to, natural lipids, synthetic lipids, phospholipids, or microbial lipids.

Liposomes can interact with cells via at least four different mechanisms: Endocytosis by phagocytic cells of the reticuloendothelial system such as macrophages and/or neutrophils; adsorption to the cell surface, either by nonspecific weak hydrophobic and/or electrostatic forces, and/or by specific interactions with cell-surface components; fusion with the plasma cell membrane by insertion of the lipid bilayer of the liposome into the plasma membrane, with simultaneous release of liposomal contents into the cytoplasm; and/or by transfer of liposomal lipids to cellular and/or subcellular membranes, and/or vice versa, without any association of the liposome contents. Varying the liposome formulation can alter which mechanism is operative, although more than one may operate at the same time.

The size of the liposomes varies depending on the method of synthesis. In one aspect, liposomes are from less than or equal to about 1 nm, 10 nm, 50 nm, 100 nm, 120 nm, 130 nm, 140 nm, or 150 nm, up to about 175 nm, 180 nm, 200 nm, 250 nm, 300 nm, 350 nm, 400 nm, 500 nm, 1 μm, 10 μm, 100 μm, 1000 μm or more in diameter. A liposome suspended in an aqueous solution is generally in the shape of a spherical vesicle, having one or more concentric layers of lipid bilayer molecules. Each layer consists of a parallel array of molecules represented by the formula XY, wherein X is a hydrophilic moiety and Y is a hydrophobic moiety. In aqueous suspension, the concentric layers are arranged such that the hydrophilic moieties tend to remain in contact with an aqueous phase and the hydrophobic regions tend to self-associate. For example, when aqueous phases are present both within and outside the liposome, the lipid molecules may form a bilayer, known as a lamella, of the arrangement XY-YX. Aggregates of lipids can form when the hydrophilic and hydrophobic parts of more than one lipid molecule become associated with each other. The size and shape of these aggregates will depend upon many different variables, such as the nature of the solvent and the presence of other agents in the solution.

Liposomes can be made by different methods known to those of ordinary skill in the art. Liposomes can be prepared in accordance with known laboratory techniques. In one embodiment, liposomes are prepared as described in the Examples, below. In another embodiment, liposomes are prepared by mixing liposomal lipids, in a solvent in a container, e.g., a glass, pear-shaped flask. The container can have a volume ten-times greater than the volume of the expected suspension of liposomes. Using a rotary evaporator, the solvent can be removed at approximately 40° C. under negative pressure. The solvent normally is removed within about 5 min. to 2 hours, depending on the desired volume of the liposomes. The composition can be dried further in a desiccator under vacuum. The dried lipids generally are discarded after about 1 week because of a tendency to deteriorate with time.

Dried lipids can be hydrated at, e.g., approximately 25-50 mM phospholipid in sterile, pyrogen-free water by shaking until all the lipid film is resuspended. The aqueous liposomes can be then separated into aliquots, each placed in a vial, lyophilized and sealed under vacuum.

In the alternative, liposomes can be prepared in accordance with other known laboratory procedures: the method of Bangham et al. (1965), the contents of which are incorporated herein by reference; the method of Gregoriadis, as described in Drug Vehicles in Biology and Medicine, G. Gregoriadis ed. (1979) pp. 287-341, the contents of which are incorporated herein by reference; the method of Deamer and Uster, 1983, the contents of which are incorporated by reference; and the reverse-phase evaporation method as described by Szoka and Papahadjopoulos, 1978. The aforementioned methods differ in their respective abilities to entrap aqueous material and their respective aqueous space-to-lipid ratios, and each is incorporated by reference for all purposes.

The dried lipids or lyophilized liposomes prepared as described above can be dehydrated and reconstituted in a solution of inhibitory peptide and diluted to an appropriate concentration with a suitable solvent. The mixture is then vigorously shaken in a vortex mixer. Contaminants are removed by centrifugation at 29,000×g and the liposomal pellets washed. The washed liposomes are resuspended at an appropriate total phospholipid concentration, e.g., about 50-200 mM.

In addition to the above, micelles can be prepared in accordance with known laboratory techniques. For example, micelles can be prepared in accordance with the methods of: J. M. Seddon, R. H. Templer. *Polymorphism of Lipid-Water Systems*, from the Handbook of Biological Physics, Vol. 1, ed. R. Lipowsky, and E. Sackmann. (c) 1995, Elsevier Science B.V. ISBN 0-444-81975-4, the contents of which are incorporated by reference; S. A. Baeurle, J. Kroener, Modeling effective interactions of micellar aggregates of ionic surfactants with the Gauss-Core potential, J. Math. Chem. 36, 409-421 (2004), the contents of which are incorporated by reference; McBain, J. W., Trans. Faraday Soc. 1913, 9, 99, the contents of which are incorporated by reference; Hartley, G. S., Aqueous Solutions of Paraffin Chain Salts, A Study in Micelle Formation, 1936, Hermann et Cie, Paris, the contents of which are incorporated by reference.

In some embodiments, polymersomes can be used. Polymersomes can be made using amphiphilic synthetic block copolymers to form the vesicle membrane, and can have radii ranging from less than 50 nm to 5 μm or more. Polymersomes generally contain an aqueous solution in their core. The polymersome membrane can provide a physical barrier that isolates encapsulated material from external materials, such as those found in biological systems. Synthasomes are polymersomes engineered to contain channels (formed using transmembrane proteins or other pore-forming molecules) that allow certain chemicals to pass through the membrane, into or out of the vesicle. This can allow for the collection or enzymatic modification of these substances.

While having many of the properties of liposomes, polymersomes can exhibit increased stability and reduced permeability. Furthermore, the use of synthetic polymers can enable designers to manipulate the characteristics of the membrane and thus control permeability, release rates, stability, and other properties of a polymersome.

Various polymers can be used for making polymersomes including poly(ethylene glycol) (PEG/PEO), poly(2-methyloxazoline), polydimethulsiloxane (PDMS), poly(caprolactone) (PCL), poly(lactide) (PLA), and poly(methyl methacrylate) (PMMA).

Various embodiments of polymersomes, methods of making polymersomes, and methods of using polymersomes are described in U.S. Pat. Pubs. 20050003016, 20050048110, 20050180922, 20060165810, 20070218123, 20080181939, 20090220614, 20100255112, and 20100305201, each of which is herein incorporated by reference in its entirety, for all purposes. See also Discher B M; Won Y Y; Ege D S; Lee J C; Bates F S; Discher D E; Hammer D A *Science* (1999), 284(5417), 1143-6, herein incorporated by reference.

Other embodiments can be found in co-owned patent applications U.S. Provisional Application No. 60/886,276, filed Jan. 23, 2007, U.S. Ser. No. 12/206,569, filed Sep. 8, 2008, and PCT application PCT/US2008/00915, filed Jan. 23, 2008, the entire disclosures of which are herein incorporated by reference in their entirety for all purposes.

Transition Metals

Transition metals can include the Group 1B, 2B, 3B, 4B, 5B, 6B, 7B and 8B elements (groups 3-12). In one embodiment the transition metal is copper. In one embodiment, metals include Fe, Co, Ni, Cu, Zn, V, Ti, Cr, Rh, Ru, Mo, Mn and/or Pd. In one embodiment, the metal is Fe, Co, Ni, Cu, Mn or Zn. In one embodiment, the metal is Zn, Mn, Co or Cu. In one embodiment, the metal is Zn, Co, or Cu. In one embodiment, the metal is Cu, e.g., Cu(II).

Transition metal ions may be encapsulated in or associated with carriers, e.g. liposomes, according to conventional techniques known in the art. This includes the passive encapsulation techniques known in the art.

Various salts of metals may also be employed. In one embodiment, the salt is pharmaceutically acceptable and soluble in aqueous solvent. In one embodiment salts may be chlorides, sulfates, tartrates, citrates, phosphates, nitrates, carbonates, acetates, glutamates, gluconates, glycinates, histidinates, lysinates and the like.

In one embodiment, a therapeutic agent to be associated with a liposome is one which is capable of coordinating with a metal encapsulated in the liposome. Agents that are capable of coordinating with a transition metal typically include coordination sites such as amines, carbonyl groups, ethers, ketones, acyl groups, acetylenes, olefins, thiols, hydroxyl, halides, groups or other suitable groups capable of donating electrons to the transition metal thereby forming a complex with the metal. Examples of agents which bind transition metals include quinolones such as fluoroquinolones, quionlones such as nalidixic acid, anthracyclines such as doxorubicin, daunorubicin idarubicin and epirubicin, amino glycosides such as kanamycin and other antibiotics such as bleomycin, mitomycin C and tetracycline and nitrogen mustards such as cyclophosphamide, thiosemicarbazones, indomethacin and nitroprusside, camptothecins such as topotecan, irinotecan, lurtotecan, 9-aminocamptothecin, 9-nitrocamptothecin and 10-hydroxycamptothecin and podophyllotoxins such as etoposide. Agents can be capable of donating electrons from different atoms in the agent and to different sites in the geometric structure of the complex. Such agents capable of donating more than one non-bonding pair of electrons are also known as multidentate. In one embodiment a therapeutic agent is an antineoplastic agent.

Methods of determining whether coordination occurs between an agent and a transition metal include conventional techniques well know to those of skill in the art. In one embodiment techniques involve measuring the absorption spectra or using NMR as described by Greenaway and Dabrowiak (J. Inorg. Biochem. (1982) 16(2): 91). If desired, an active agent may be tested before encapsulation in order to determine whether coordination occurs and the optimal pH for complexation.

In some embodiments an agent-transition metal complex can form an agent-transition metal crystal. In some embodiments, the crystal is a Dox-Cu crystal. In some embodiments, the crystal is fine in size. In some embodiments, the crystal is less than 0.1 nm to greater than 50 nm in size. In some embodiments, the crystal is less than 0.1, 0.2, 0.3, 0.4, 0.5, 0.6, 0.7, 0.8, 0.9, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, or greater than 50 nm in size. In some embodiments, the crystal is stable at neutral pH and unstable at a pH lower than neutral.

In one embodiment a technique for preparing liposomes with an associated metal involves first combining lipids in chloroform to give a desired mole ratio. A lipid marker may optionally be added to the lipid preparation. The resulting mixture is dried under a stream of nitrogen gas and placed in a vacuum pump until the solvent is removed. Subsequently, the samples are hydrated in a solution comprising a transition metal (which may comprise more than one metal, for example Cu and Mn, or one metal, but different salts of the metal). The mixture is then passed through an extrusion apparatus to obtain a preparation of liposomes of a defined size. Average liposome size can be determined by quasi-elastic light scattering using a NICOMP 370 submicron particle sizer at a wavelength of 632.8 nm. Subsequent to extrusion, the external solution may be treated or replaced so as to remove metal ions from the external solution and the liposome surface.

In one embodiment, use of liposomes with an encapsulated or "internal" medium comprising a transition metal in a "metal compatible solution" is contemplated. Use of a metal compatible solution prevents precipitation of the metal or minimizes precipitation to an extent sufficient to allow for pharmaceutical use of the liposomes.

A metal compatible solution is defined as a metal in solution that does not cause unacceptable precipitation to occur for at least the time required to formulate liposomes. In one embodiment, the metal solution should be clear and soluble, free of aggregation, precipitation or flocculation for at least about 4 hours. By way of example, a 300 mM solution of $MnSO_4$ in pH 7.4 HEPES buffer as described in Cheung, et al. is not a metal compatible solution as it produces an obvious brown precipitate of $Mn(OH)_2$ comprising approximately 6-7 molar % of the manganese added to the solution.

Various methods are known in the art and may be used to determine if the metal solution is forming a precipitate such as centrifugation of the solution and an evaluation of whether a pellet is formed or observation of cloudiness in the solution. The absorbance of the solution can also be monitored by spectroscopy (e.g., increase in absorbance at 690 nm), where a substantial increase in absorbance is indicative of solution instability and precipitation. The simplest method is to filter the solution and look for the presence of a precipitate on the filter. For example, a 50 ml sample may be passed through Whatman No. 2 filter paper and the filter observed for visible sediment.

In one embodiment a method to determine whether a solution is metal compatible is to monitor absorbance at 690 nm.

An alternative preferred method of determining whether a metal solution is metal compatible is by centrifugation (e.g., 100 ml sample at 1000 rpm for 10 minutes) to collect any precipitate, measuring the amount of precipitate collected and determining the proportion of the metal added to the original solution present in the precipitate.

In one embodiment metal compatible solutions are those that are also pharmaceutically acceptable such as ones comprising triethanolamine (TEA), sodium chloride, sodium acetate/acetic acid, sodium citrate/citric acid or sugars such as sucrose, dextrose and lactose. Phosphate and carbonate based solutions (although pharmaceutically acceptable) will have limited use except at pH's outside of normal physiological ranges, due to the likelihood of metal precipitation. In one embodiment, the metal compatible solution is buffered and has pH in a mammalian physiological range.

In one embodiment, it may be advantageous for the external solution of the liposome preparation to be replaced or be treated in order that the resulting external solution contain substantially no uncomplexed metal ions prior to loading of an agent. For purposes of this specification, "uncomplexed metal ions" includes metal ions free in the external solution and metal ions bound to (or otherwise associated with) the external surface of the liposomes. Conversely, a complexed metal ion is one which is no longer free to interact with the therapeutic agent or the liposome surface because it is present in the external solution in a complex with a moiety such as a chelating agent. Thus, the surface of the liposomes and the external solution can be substantially free of the metal ions or if metal ions are present, that they be complexed with a chelating agent. Examples of cationic chelating agents that may be employed include: EDTA and derivatives; EGTA and derivatives; histidine; Chelex; TPEN and derivatives; BAPTA and derivatives; bishosphonate; o-phenanthrolene (phenanthroline); citrate; InsP6; Diazo-2; and DTPA (diethylene-triaminopenta acetic acid) isothiocyanate.

Replacement of the external solution to remove metal ions can be accomplished by various techniques, such as by chromatography of the liposome preparation through an extensive gel filtration column equilibrated with a second aqueous buffered solution, by centrifugation, extensive or repeated dialysis, exchange of the external medium, treating the external solution with chelating agents or by related techniques. A single solution exchange or round of dialysis without the use of a chelating agent is typically insufficient to remove metal ions from the surface of negatively charged liposomes.

The external solution can be a buffered solution. However, it is appreciated that any suitable solvent may be utilized. In one embodiment an external solution has a pH at about mammalian physiological pH and comprises a buffer which has a buffering range to include physiological pH. Non-limiting examples of suitable buffers for the external solution are HBS, pH 7.4 (150 mM NaCl, 20 mM HEPES) and SHE, pH 7.4 (300 mM sucrose, 20 mM HEPES, 30 mM EDTA).

Uptake of an agent may be established by incubation of the mixture at a suitable temperature after addition of the agent to the external medium. Depending on the composition of the carrier, temperature and pH of the internal medium and chemical nature of the agent, uptake of the agent may occur over a time period of minutes or hours. Loading may be carried out at temperatures of, for example, 20 C to about 75 C, or from about 30 C. to about 60 C.

Removal of unencapsulated agent may be carried out by passing a liposome preparation through a gel filtration column equilibrated with a second aqueous buffered solution, or by centrifugation, dialysis, or related techniques. In one embodiment, the second solution is one that is physiologically compatible but need not be "metal compatible." After removal of unencapsulated active agent, the extent of agent loading may be determined by measurement of drug and lipid levels according to conventional techniques. Lipid and drug concentrations may be determined by employing techniques such as scintillation counting, spectrophotometric assays, fluorescent assays and high performance liquid chromatography. The choice of analysis depends on the nature of the drug and whether the liposomes contain a radiolabeled lipid marker.

Prior to loading of an agent into a liposome using an encapsulated transition metal, the liposome may be passively co-encapsulated with an agent and a metal. Using this approach, two or more agents may be incorporated into the liposome by combining passive and active methods of loading.

Subsequent to loading of an agent into a liposome, an ionophore may be incubated with the mixture such that insertion of the ionophore into the bilayer occurs. The term "ionophore" refers to a compound which forms a complex with a metal ion and assists the ion in crossing a lipid bilayer while further assisting the transport of H+ in the counter direction. Examples of suitable ionophores include nigericin, monensin, dianemycin, A23187, 4-BrA23187, ionomycin and X-537A. The ionophores may be specific for monovalent or divalent metal ions. Examples of ionophores specific for monovalent metal ions include nigericin, monensin and dianemycin. Uptake of the ionophore is established by addition of the ionophore to the mixture and incubation at a temperature suitable for incorporation of the ionophore into the liposomal bilayer. The amount of ionophore used will typically depend on the nature and type of liposome formulation. Addition of the ionophore to the liposome after loading of the agent may be carried out in order to subsequently impose a pH gradient across the liposomal bilayer to alter the retention properties of the agent in the liposome or to protect agents that are affected by neutral or alkaline environments such as, topotecan and irinotecan.

In one embodiment metal compatible solutions may include components such as buffers that can be utilized between pH 6.0 and 8.5. In one embodiment, the buffer does not substantially precipitate over a two-day time period at 4 C. with an encapsulated metal ion at pH 6.0 to 8.0 and more preferably pH 6.5 to 7.5. A buffer may be tested for its ability to prevent precipitation by visually inspecting the solution for the appearance of cloudiness, which is indicative of formation of a precipitate. After encapsulation of a transition metal in a metal compatible solution, an agent may be added to the external medium such that the agent is encapsulated into the liposome. Liposomes encapsulating a transition metal and a metal compatible solution may be prepared according to conventional techniques known in the art including the techniques described above. It is appreciated, however, that any suitable metal may be utilized. In one embodiment, the liposome with the encapsulated agent or agents has an extraliposomal pH that is substantially similar to the intraliposomal pH. In one embodiment, the extraliposomal and intraliposomal pH is about pH 6.0 to pH 8.0, or it is between about pH 6.5 and pH 7.5.

In one embodiment a method of designing liposomes, the method comprising selecting a metal ion for encapsulation in a liposome to achieve a desired retention of an encapsulated agent is described. It will be appreciated that any suitable liposome and agent may be utilized. Other preferred features and conditions of this aspect are as generally described above.

In order to determine the rate of release of an agent from a liposome, the liposome may be administered intravenously and plasma levels of agent and lipid measured after administration. For example, the lipid component may be radioactively labeled and the plasma subjected to liquid scintillation counting. The amount of drug may be determined by a spectrophotometric, HPLC or other assays. Similarly, testing for the retention of the agent in the liposome may be carried out in vitro in plasma or a suitable buffer. By way of example, a liposome comprising an encapsulated agent and transition metal may be tested in vitro or in vivo for retention of agent. If a desired retention of the agent is not achieved, a different metal may be selected and tested for its ability to retain the agent of interest.

See also U.S. Pub. No. 20060193904, herein incorporated by reference for all purposes.

Agents

An agent can include small molecules, therapeutic agents and pharmacologically-active agents, nutritional molecules, cosmetic agents, diagnostic agents, labels, and imaging agents. In one embodiment, an agent can be doxorubicin. In another embodiment, an agent can be rapamycin. In some embodiments, the agent is an anthracycline. In some embodiments, the anthracycline is selected from the group consisting of: daunorubicin, doxorubicin, epirubicin, idarubicin, mitoxantrone, valrubicin, and irinotecan. In some embodiments, the anthracycline is doxorubicin.

In one embodiment, an agent to be associated with a liposome is one which is capable of coordinating with a metal encapsulated in the liposome. Agents that are capable of coordinating with a transition metal typically include coordination sites such as amines, carbonyl groups, ethers, ketones, acyl groups, acetylenes, olefins, thiols, hydroxyl, halides, groups or other suitable groups capable of donating electrons to the transition metal thereby forming a complex with the metal. Examples of agents which bind transition metals include quinolones such as fluoroquinolones, quionlones such as nalidixic acid, anthracyclines such as doxorubicin, daunorubicin idarubicin and epirubicin, amino glycosides such as kanamycin and other antibiotics such as bleomycin, mitomycin C and tetracycline and nitrogen mustards such as cyclophosphamide, thiosemicarbazones, indomethacin and nitroprusside, camptothecins such as topotecan, irinotecan, lurtotecan, 9-aminocamptothecin, 9-nitrocamptothecin and 10-hydroxycamptothecin and podophyllotoxins such as etoposide. Agents can be capable of donating electrons from different atoms in the agent and to different sites in the geometric structure of the complex. Such agents capable of donating more than one non-bonding pair of electrons are also known as multidentate. In one embodiment an agent is an antineoplastic agent.

Methods of determining whether coordination occurs between an agent and a transition metal include conventional techniques well know to those of skill in the art. In one embodiment techniques involve measuring the absorption spectra or using NMR as described by Greenaway and Dabrowiak (J. Inorg. Biochem. (1982) 16(2): 91). If desired, an active agent may be tested before encapsulation in order to determine whether coordination occurs and the optimal pH for complexation.

Agents can include an mTOR inhibitor, an anti-inflammatory agent, or an anti-angiogenic agent. Agents can also include nucleic acids, e.g., genes, siRNA, microRNA, viruses, vectors, or gene fragments.

Typically a composition includes at least one agent. In general, the amount of the particular agent associated with a carrier is selected according to the desired therapeutic dose and/or the unit dose. Suitable therapeutic agents can include, for example, antineoplastics, monomethylauristatin E, monomethylauristatin F, antitumor agents, antibiotics, antifungals, anti-inflammatory agents, immunosuppressive agents, anti-infective agents, antivirals, anthelminthic, antiparasitics, angiogenic agents, anti-thrombotic agents, anti-inflammatory agents, immunosuppressive agents, anti-arrhythmic agents, tumor necrosis factor inhibitors, endothelin inhibitors, angiotensin-converting enzyme (ACE) inhibitors, calcium antagonists, statins, beta blockers, blood thinners, antibiotic agents, antiviral agents, and viral vectors.

As used herein, agent includes pharmacologically-acceptable salts of agents. Suitable therapeutic agents can also include, for example, antineoplastics, monomethylauristatin E (MMAE), monomethylauristatin F (MMAF), antitumor agents, antibiotics, antifungals, anti-inflammatory agents, immunosuppressive agents, anti-infective agents, antivirals, anthelminthic, and antiparasitic compounds. Suitable antitumor agents include agents such as cisplatin, carboplatin, tetraplatin, and iproplatin. Suitable antitumor agents also include adriamycin, mitomycin C, actinomycin, ansamitocin and its derivatives, bleomycin, Ara-C, doxorubicin, daunomycin, metabolic antagonists such as 5-FU, methotrexate, isobutyl 5-fluoro-6-E-furfurylideneamino-xy-1,2,3,4,5,6 hexahydro-2,4-dioxopyrimidine-5-carboxylate. Other antitumor agents include melpharan, mitoxantrone and lymphokines. The amount of the particular antitumor agent associated with a carrier is selected according to the desired therapeutic dose and/or the unit dose.

In view of the above, it is understood that a variety of therapeutic agents can be useful for treating a disease. Useful therapeutic agents for treating diseases can also include angiogenic agents, anti-thrombotic agents, anti-inflammatory agents, immunosuppressive agents, anti-arrhythmic agents, tumor necrosis factor inhibitors, endothelin inhibitors, angiotensin-converting enzyme inhibitors, calcium antagonists, antibiotic agents, antiviral agents and viral vectors. One skilled in the art understands that these as well as additional known or other therapeutic agents can be selectively directed to a tumor when incorporated into an embodiment of a composition or method of the invention. Furthermore, one skilled in the art understands that these and other therapeutic agents can be used separately or together with the embodiments of compositions and methods of the invention.

In another embodiment, the carrier can carry an imaging agent detectable by means such as e.g., color, fluorescence, radiation, or electromagnetic signals. Imaging agents will typically include, but are not limited to, fluorescent moieties, chemiluminescent moieties, carriers, enzymes, dyes, radiolabels, quantum dots, light emitting moieties, light absorbing moieties, and intercalating dyes including propidium iodide and ethidium bromide and the cyanine dyes. Imaging agents are agents that are generally capable of producing, either directly or indirectly, a detectable signal. Some examples of the types of imaging agents that can be used include, e.g., fluorescent or colored dyes, isotopic labels, enzymes, immune labels (e.g., antibodies or antigens), gold carriers, fluorophores, magnetic carriers, and quantum dots. The imaging agents can be incorporated into a carrier or associated with a carrier. The imaging agents can be attached to a carrier. The imaging agents can be carried by a carrier. The imaging agent can directly or indirectly provide a detectable signal. Any method known in the art for conjugating and/or binding an imaging agent to a carrier can be used.

In one embodiment, fluorescent labels are used as imaging agents. Fluorescent or chemiluminescent imaging agents that can be used are, e.g., fluorescein isothiocyanate, rhodamine, and luciferin. In another embodiment, the imaging agents are radiolabels, e.g., $^3$H, $^{125}$I, $^{35}$S, $^{14}$C, $^{18}$F, [$^{18}$F]FDP, $^{64}$Cu, or $^{32}$P. One of skill in the art will appreciate that the imaging agent can be an enzyme (e.g., horse radish peroxidase, alkaline phosphatase, beta-galactosidase and others commonly used in, e.g., an ELISA); biotin for staining with labeled streptavidin conjugate; magnetic beads, and labels such as colloidal gold or colored glass or plastic (e.g., polystyrene, polypropylene, latex, etc.) beads.

In another embodiment, the carrier can be associated with a plurality of distinct agents. The plurality can include 2, 3, 4, 5, 6, 7, 8, 9, 10 or more agents, as is deemed necessary by one of ordinary skill.

In some embodiments, an agent can be coupled to a carrier through a chemically-reactive group. In other aspects, an agent can be attached to a carrier during synthesis of the carrier or incorporated on the carrier after carrier synthesis.

Energy Sources

Energy sources can include an ultrasound source, a microwave source, a radio-frequency source, a laser source, and/or an excitation of heat-sensitive particles using other energy sources known in the art. Energy sources can produce various forms of irradiation. Energy sources can produce heat such as mild hyperthermia. As used herein, the term "hyperthermia" refers to the elevation of the temperature of a subject's body, or a part of a subject's body, compared to the normal temperature of the subject. Conditions for mild hyperthermia typically range from 37 to 42° C. (Murata, R. and M. R. Horsman (2004). "Tumour-specific enhancement of thermoradiotherapy at mild temperatures by the vascular targeting agent 5,6-dimethylxanthenone-4-acetic acid." Int J Hyperthermia 20(4): 393-404; Horsman, M. R. (2006). "Tissue physiology and the response to heat." Int J Hyperthermia 22(3): 197-203; Li, G. C., F. He, et al. (2006). "Hyperthermia and gene therapy: potential use of microPET imaging." Int J Hyperthermia 22(3): 215-21; Myerson, R. J., A. K. Singh, et al. (2006). "Monitoring the effect of mild hyperthermia on tumour hypoxia by Cu-ATSM PET scanning" Int J Hyperthermia 22(2): 93-115). Mild hyperthermia causes several physiological effects including, but not limited to increased blood flow, increased oxygenation, increased microvascular permeability, increased pH, increased heat shock protein production, and decreased healing time for musculo-skeletal injuries. It has been demonstrated that mild hyperthermia increases the effectiveness of radiochemotherapy in human tumors. It has also been demonstrated that mild hyperthermia increases vascular permeability to allow extravasation of nanoparticles and molecules including but not limited to albumin, dextran, liposomes, micelles, quantum dots, and polymers. Including the above noted energy sources; heat for hyperthermia can be produced by, e.g., irradiation with acoustic waves, electromagnetic waves, ionizing radiation, laser irradiation, and/or microwaves.

Heat for use with the carriers can be applied using any heating device known in the art or later discovered. For example, the heating device includes a suitable energy source that is able to focus the energy on the target and is able to control heat and temperature of the tissue. The energy source can be an electrical resistance heating element, or an indirectly heated element. The heating device can also have an energy source for producing heat at the target site, such as a radio frequency ("RF") device, ultrasonic generators, laser, or infrared device. One example of an RF generator heating device for hyperthermally treating tissue in a selected target site is disclosed in U.S. Pat. No. 6,197,022, which is hereby incorporated by reference in its entirety. Examples of suitable ultrasound heating devices for delivering ultrasonic hyperthermia are disclosed in U.S. Pat. Nos. 4,620,546, 4,658,828 and 4,586,512, the disclosures of which are hereby incorporated by reference in their entirety. In one embodiment, heat is applied using an ultrasound device.

The energy source can be applied to a variety of the areas in a body where hyperthermal treatment is desired, such as e.g., a target site. The target site is a localized site or region of the body and can be or include e.g. tumors, organs, muscles, and/or one or more soft tissues.

To deliver an agent to a region of interest, a therapeutic sequence that creates "vasoporation" can be transmitted while carriers fill the vasculature. In this sequence, therapeutic pulses with a center frequency between about 0.1 MHz-5.0 MHz, or from about 0.75 MHz-1.5 MHz are applied to each region within the therapeutic volume at an intensity from about 0.1 MPa-10.0 MPa, or from about 0.75 MPa-2 MPa. Other parameters are described in the Examples below. These therapeutic pulses can be interleaved with the imaging pulses. Subsequent to or concurrently with or prior to the application of these vasoporation pulses, a drug that extravasates through this altered vasculature is administered, alone, or in association with a carrier. Further modifications to parameters such as, e.g., the duty cycle, pulse length, acoustic pressure, and center frequency may be altered by the practitioner or system depending on the flow rate of blood vessels at the desired site, the depth of the region of interest, and the specific properties of the carrier.

Ultrasound systems include the phased system array (HDI c000cv, Advanced Technologies Laboratories) for delivering ultrasound and imaging, the system described in U.S. Pat. No. 5,558,092, to Unger et al., and may include external application, for skin and other superficial tissues, but for deep structures, application of sonic energy via interstitial probes or intravascular ultrasound catheters may be used.

Methods for Localizing Compositions and Treatment

Methods can be used for targeting cells or tissues in a subject using the compositions. In general these methods can be used for therapeutic applications and/or imaging applications, e.g., PET imaging, in a subject by injection and/or administration to the subject. In one embodiment, a method includes a method for localized delivery of an agent to a target site in a subject. In one aspect of the methods for therapeutic and imaging applications, a variety of routes of administration are useful. Such routes encompass systemic and local administration and include, without limitation, oral administration, intravenous injection, intraperitoneal injection, intramuscular injection, subcutaneous injection, transdermal diffusion or electrophoresis, local injection, and extended release delivery devices including locally implanted extended release devices such as bioerodible or reservoir-based implants. Typically, following administration and/or injection, the compositions will target the cell or tissue of interest in the subject after application of an energy source to a target site in the subject.

In one embodiment, methods of administering compositions to a mammal, and methods of treating a mammal affected by or susceptible to or suspected of being affected by a disorder (e.g., cancer) are provided. Methods of treatment or of administration will generally be understood to comprise administering the pharmaceutical composition at a dosage sufficient to ameliorate the disorder or symptoms thereof.

For treatment of human ailments, a qualified physician may be expected to determine how the compositions should be utilized with respect to dose, schedule and route of administration using established protocols. Such applications may also utilize dose escalation should active agents encapsulated in delivery carrier compositions exhibit reduced toxicity to healthy tissues of the subject.

Diseases and Conditions

The methods can be useful for treating a variety disease types in a given subject, e.g., a human or other mammal. Diseases can include cancer, diabetes, infection, inflammation, or cardiovascular disease. Cancers to be treated can include, but are not limited to, skin cancer, liver cancer, brain cancer, head-and-neck cancer, lung cancer, and/or abdominal cancers. Other types of cancers are generally known in the art. In this example, a composition will typically concentrate in the tumor. Thus, the compositions and methods are useful for treating these and other disorders associated with cancer. In one embodiment, cardiovascular disease can include ischemic conditions, cardiopathies, cardiovascular diseases, and brain diseases including cancer. For example, cardiopathies and cardiovascular diseases include, but are not limited to, coronary artery disease (CAD); atherosclerosis; thrombosis; restenosis; vasculitis including autoimmune and viral vasculitis such as polyarteritis nodosa, Churg-Strass syndrome, Takayasu's arteritis, Kawasaki Disease and Rickettsial vasculitis; atherosclerotic aneurisms; myocardial hypertrophy; congenital heart diseases (CHD); ischemic heart disease and anginas; acquired valvular/endocardial diseases; primary myocardial diseases including myocarditis; arrhythmias; and transplant rejection. Cardiopathies and cardiovascular diseases to be treated can further include, but are not limited to, metabolic myocardial diseases and myocardiomyopathies such as congestive, hypertrophic and restrictive cardiomyopathies, and heart transplants. In this example, a composition will typically concentrate in the heart blood vessels and can further accumulate in the myocardium. Thus, the various embodiments of compositions and methods of the invention can be useful for treating these and other disorders of heart blood vessels or myocardium, among other things.

Pharmaceutical Compositions

Methods for treatment of diseases also are also described. The methods include administering a therapeutically-effective amount of a composition. The composition can be formulated in pharmaceutical compositions. These compositions can comprise, in addition to one or more of the carriers, a pharmaceutically acceptable excipient, vehicle, buffer, stabilizer, or other materials well known to those skilled in the art. Such materials should be non-toxic and should not interfere with the efficacy of the active ingredient. The precise nature of the carrier or other material can depend on the route of administration, e.g., oral, intravenous, cutaneous or subcutaneous, nasal, intramuscular, or intraperitoneal routes.

Pharmaceutical compositions for oral administration can be in tablet, capsule, powder or liquid form. A tablet can include a solid carrier such as gelatin or an adjuvant. Liquid pharmaceutical compositions generally include a liquid carrier such as water, petroleum, animal or vegetable oils, mineral oil or synthetic oil. Physiological saline solution, dextrose or other saccharide solution or glycols such as ethylene glycol, propylene glycol, or polyethylene glycol can be included.

For intravenous, cutaneous or subcutaneous injection, or injection at the site of affliction, the active ingredient will be in the form of a parenterally acceptable aqueous solution which is pyrogen-free and has suitable pH, isotonicity and stability. Those of relevant skill in the art are well able to prepare suitable solutions using, for example, isotonic carriers such as Sodium Chloride Injection, Ringer's Injection, Lactated Ringer's Injection. Preservatives, stabilizers, buffers, antioxidants and/or other additives can be included, as required.

Administration of the composition is preferably in a "therapeutically-effective amount" or "prophylactically-effective amount," (as the case can be, although prophylaxis can be considered therapy), this being sufficient to show benefit to the individual. The actual amount administered, and rate and time-course of administration, will depend on the nature and severity of the disease being treated. Prescription of treatment, e.g., decisions on dosage, is within the responsibility of general practitioners and other medical doctors, and typically takes account of the disorder to be treated, the condition of the individual patient, the site of delivery, the method of administration and other factors known to practitioners. Examples of the techniques and protocols mentioned above can be found in Remington's Pharmaceutical Sciences, 16th edition, Osol, A. (ed.), 1980.

A composition can be administered alone or in combination with other treatments, either simultaneously or sequentially dependent upon the condition to be treated.

EXAMPLES

Below are examples of specific embodiments for carrying out the present invention. The examples are offered for illustrative purposes only, and are not intended to limit the scope of the present invention in any way. Efforts have been made to ensure accuracy with respect to numbers used (e.g., amounts, temperatures, etc.), but some experimental error and deviation should, of course, be allowed for.

The practice of the various embodiments of the present invention can employ, unless otherwise indicated, conventional methods of protein chemistry, biochemistry, recombinant DNA techniques and pharmacology, within the skill of the art. Such techniques are explained fully in the literature. See, e.g., T. E. Creighton, *Proteins: Structures and Molecular Properties* (W.H. Freeman and Company, 1993); A. L. Lehninger, *Biochemistry* (Worth Publishers, Inc., current addition); Sambrook et al., *Molecular Cloning: A Laboratory Manual* (2nd Edition, 1989); *Methods In Enzymology* (S. Colowick and N. Kaplan eds., Academic Press, Inc.); *Remington's Pharmaceutical Sciences*, 18th Edition (Easton, Pa.: Mack Publishing Company, 1990); Carey and Sundberg *Advanced Organic Chemistry* $3^{rd}$ Ed. (Plenum Press) Vols A and B (1992).

Materials and Methods

Liposomes and Drug Preparation

Doxil® (Ortho Biotech Products, LP Raritan, N.J.), a commercial ammonium sulfate-loaded doxorubicin liposome, is used for comparison to experimental preparations. Long-circulating liposomes (LCLs) prepared from HSPC: chol:DSPE-PEG2k (56:39:5), the lipid composition of Doxil, were used in this study[28].

Copper Liposome Preparation

Liposomes were prepared as described in[29]. L-α-phosphatidylcholine, hydrogenated soy (HSPC), 1,2 distearoylsn-glycero-3-phosphoethanolamine-N-Methoxy polyethyleneglycol-2000 (DSPE-PEG2k), 1,2-dipalmitoyl-sn-glycero-3-phospho-choline (DPPC), and 1,2-distearoyl-sn-glycero-3-phosphocholine (DSPC) were purchased from Avanti Polar Lipids Inc. (Alabaster, Ala.). The dried lipid was hydrated in 0.3 ml of 100 mM copper (II) gluconate (PURAC, Lincolnshire, Ill.) including 270 mM triethanolamine (TEA, Sigma, St. Louis, Mo.), pH 7.4 unless otherwise stated. The multi-lamellar lipid solution at a final concentration of 50 mg/mL was extruded above the phase transition temperature of the lipid mixture through a polycarbonate membrane with a pore diameter of 100 nm. Copper/TEA-loaded liposomes were then separated from non-encapsulated copper/TEA by passing the extruded liposomal solution through a spin column of Sephadex G-75 (5×1 cm, GE Healthcare, Biosciences, Piscataway, N.J.) equilibrated with saline (0.9% sodium chloride). The liposomal diameters were ~100 nm (103 nm±13 nm), as measured using a NICOMP™ 380 ZLS submicron particle analyzer (Particle Sizing System Inc., Santa Barbara, Calif.). Lipid concentration was measured using the Phospholipids C assay kit (Wako Chemicals USA, Richmond, Va.). Doxorubicin hydrochloride supplied by Sigma (St. Louis, Mo.) was then loaded and the resulting liposomes purified and characterized.

Protocol

All animal handling was performed in accordance with University of California, Davis (UCD), Animal Use and Care Committee guidelines. Efficacy studies involved 80 animals, randomized between 10 groups (ultrasound only, copper-doxorubicin (Cu-Dox) liposomes, rapamycin, Doxil, Cu-Dox-liposomes+ultrasound, Cu-Dox-liposomes+rapamycin, Cu-Dox-liposomes+rapamycin+ultrasound, Doxil+rapamycin, doxorubicin, diluent only). Toxicity studies involved 32 animals randomized between 4 groups (doxorubicin, Cu-Dox-liposomes, Doxil, and control). Mice bearing bilateral Met-1 tumors of 4-6 mm in longitudinal diameter ($\geq 100$ mm$^3$) were injected intravenously with either free or liposomal doxorubicin (~6 mg doxorubicin/kg body weight and ~32 mg lipid/kg body weight) twice a week with a total doxorubicin injected dose of 267 mg/m$^2$ over 4 weeks and compared to control animals which received saline. For rapamycin, animals were treated by intraperitoneal (ip) injection of (~0.9 mg rapamycin/kg body weight) three times per week over the entire period of treatment. For combined treatments with ultrasound, one tumor per animal was insonified for 2 min at 42° C. post-injection. The ultrasound pulses consisted of 100-cycle bursts at 1.5 MHz center frequency and 1.2 MPa peak negative pressure, with variable pulse-repetition frequency (PRF) ranging from 100 Hz up to 5 kHz.

In Vivo Imaging

Images of circulating doxorubicin were acquired using the Maestro™ hyperspectral imaging system (Cambridge Research & Instrumentation, Inc., Woburn, Mass.). Animals were then euthanized and perfused with saline at 24 or 48 hours post systemic administration of the drug and the accumulation of doxorubicin or copper in tissues and organs were imaged and quantified ex vivo.

To study the systemic circulation and tumor accumulation of liposomal carriers, mice were systemically injected with liposomes labeled with $^{64}$Cu-BAT lipid to track the liposomal lipid shell and imaged using PET[30]. A near-infrared fluorophore in the drug core validated accumulation of intact particles.

Loading Optimization of Doxorubicin

To characterize and optimize doxorubicin loading, liposomes were prepared in the presence or absence of copper using 100 mM copper gluconate or 100 mOsM saline, respectively, and at varied concentrations of TEA with final pH adjusted to 7.4 by either HCl or NaOH. Using 100 mM copper and a constant copper/TEA ratio of 100 mM/270 mM, the effect of increasing the doxorubicin/lipid ratio from 0.05 to 0.5 mg/mg was investigated, achieving 100% loading efficiency with a doxorubicin/lipid ratio within the 0.05 to 0.2 mg/mg range (FIG. 7a). Doxorubicin loading remained unchanged at doxorubicin/lipid ratios higher than 0.2 mg/mg which translates into an intra-liposomal concentration of 200 mM doxorubicin in 100 mM copper liposomes (and a 2/1 doxorubicin/copper molar ratio). At a constant copper/TEA ratio of 100 mM/270 mM and a 2/1 molar doxorubicin/copper ratio, loading efficiency was maintained as copper increased. In the absence of copper, loading efficiency did not exceed 30% (FIG. 7b). With a copper concentration of 300 mM (and 810 mM TEA), doxorubicin loading increased linearly with intra-liposomal copper concentration up to 0.6 mg doxorubicin per mg lipid (FIG. 7c). The replacement of copper gluconate with copper sulfate did not affect loading (data not shown), thus either copper salt can be applied.

Rapamycin Preparation

Rapamycin obtained from LC Laboratories (Woburn, Mass.) was dissolved in anhydrous ethanol at 50 mg/ml and aliquots were stored at −20° C. The rapamycin solution was prepared freshly by diluting the rapamycin stock solution in a solution of 10% PEG-400, 8% ethanol, and 10% Tween 80 to create a concentration of 0.176 mg/ml.

Cell Culture and In Vitro Viability Assay

MET-1$^{fvb2}$ mammary carcinoma cells were obtained from the Alexander Borowsky Laboratory (UC Davis). MET-1 cells were plated at 2000 cells in 50 µl media per well in 96-well tissue culture plates in high glucose Dulbecco's Modified Eagle's Medium (DMEM, Invitrogen, Carlsbad, Calif.) supplemented with 1% PenStrep and 10% FBS. Cells were given six hours to attach to the plate surface. Treatments were added to each well in 100 µl media and experiments were performed in triplicate. Doxil®, a commercial product of ALZA corporation and manufactured by Centocor Ortho Biotech, was purchased from Cardinal Health Care (Dublin, Ohio) and the in vitro viability was compared with the liposomal copper-doxorubicin.

Plates were incubated for 72 hours at 37° C. in 5% $CO_2$. 3-(4,5-dimethylthiazol-2-yl)-2,5-diphenyltetrazolium bromide (MTT, Invitrogen, Carlsbad, Calif.) reagent was added to media at a concentration of 0.5 mg/ml, and cells were incubated 2 hours at 37° C. in 5% $CO_2$. Media was removed, and formazan crystals were dissolved in 100 µl/well of DMSO (Sigma Aldrich, St. Louis, Mo.). Absorbance was measured using Tecan Infinite® M1000 Microplate Reader (San Jose, Calif.) at wavelength 570 nm (reference of 670 nm). Best-fit curves and IC50 values were calculated for concentration-response curves using GraphPad Prism software (GraphPad Inc., La Jolla, Calif.). Average IC50 values calculated from a minimum of three replicate experiments for each preparation.

Cryo-electron Microscopy (Cryo-EM)

Cryo-electron micrographs were collected on a JEOL JEM-2100F microscope operating at 200 kV. Cryo-EM sample preparation was described in detail previously (Xing, L.; Tjarnlund, K.; Lindqvist, B.; Kaplan, G. G.; Feigelstock, D.; Cheng, R. H.; Casasnovas, J. M., Distinct cellular receptor interactions in poliovirus and rhinoviruses. *Embo*

Journal 2000, 19, (6), 1207-1216). Briefly, a 3 µl solution containing liposomes loaded with or without doxorubicin/copper was applied on a R2/2 quantifoil holey carbon grid (Quantifoil Micro Tools GmbH) and then quickly plunged into liquid ethane after the removal of excess solution. Liposomes were embedded into a thin layer of vitrified ice and transferred into the EM using a Gatan 626 cryo-transferring system. The specimen was observed at 50,000× and the area of interest was recorded on a TVIPS CCD camera (TemCam-F415) under minimum dose conditions.

In Vitro Stability of Doxorubicin Liposomes

In vitro stability assay of liposomal copper-doxorubicin was performed in either complement-preserved human serum (Innovative Research Inc., Southfield, Mich.) or in 0.9% sodium chloride, and compared with Doxil in the presence of 10 mM EDTA at 37° C. over a period of one month. A mixture of 42 µl of doxorubicin liposomes (1 mg/ml) and 10 mM EDTA in total volume of 2.5 ml was incubated at 37° C. in sterile condition. Fluorescence intensity of doxorubicin was measured at t=0 ($R_0$), as a function of time ($R_t$), and after incubation in the presence of 0.25% Tx-100 at 55° C. for 1 h ($R_{TX}$) using the Tecan Infinite® M1000 Microplate Reader at excitation and emission wavelengths of 485 nm and 590 nm, respectively. The percent doxorubicin released was calculated as:

$$\text{Doxorubicin release \%} = \text{Doxorubicin release} (\%) = 100(R_t - R_0)/(R_{TX} - R_0) \quad (1)$$

Copper Transchelation and Stability of Copper-Doxorubicin Complex In Vitro

The copper-doxorubicin complex was formed by addition of 15 µl of 100 mM copper gluconate to 75 µl of 2 mg/ml doxorubicin solution in saline, and incubated at 37° C. To this complex was then added 1.5 ml of aqueous solutions of 0.5 mM bovine serum albumin (BSA, Sigma, St. Louis, Mo.) at pH values of 3-8, and incubated at 37° C. to create the final concentrations of 0.172 mM Dox and 1 mM copper. Fluorescence intensity of freed doxorubicin was monitored using Ex: 485 nm and Em: 590 nm at 37° C. over time and compared to that of free doxorubicin solution in saline. The measured fluorescence intensities were corrected for variations of doxorubicin fluorescence intensity with pH.

In Vivo Studies

All animal handling was performed in accordance with University of California, Davis (UCD), Animal Use and Care Committee guidelines. For in vivo Met-1 tumor studies, tumor fragments of approximately 1 mm³ were transplanted into both inguinal fat pads of 3-5 week old FVB females (Charles River Breeding Laboratories). Tumors were grown for 2 weeks after transplantation to 4-6 mm in longitudinal diameter prior to treatment.

In Vivo Antitumor Efficacy

The mice bearing bilateral Met-1 tumors were randomized into several groups of 3-4 mice/group and treated with either single or combination therapy. The animals were anesthetized by 3.5% isoflurane and maintained at 2.0-2.5% during the injection and imaging. Each mouse was injected intravenously with either free or liposomal doxorubicin (~6 mg doxorubicin/kg body weight and ~32 mg lipid/kg body weight) twice a week with a total doxorubicin injected dose of 267 mg/m² over 4 weeks and compared to control animals that received saline. For rapamycin, animals were treated by intraperitoneal (ip) injection of (~0.9 mg rapamycin/kg body weight) three times a week over the entire period of treatment. For combined treatments with ultrasound, one tumor per animal was insonified for 2 min at 42° C. post-injection.

The tumor progression/regression was monitored using a 2D Acuson Sequoia® 512 ultrasound imaging system (Siemens Medical Solution USA, Inc., Issaquah, Wash.) equipped with a 15L8-S, 14 kHz high frequency linear array transducer. After the region surrounding the tumor was shaved, the tumor was viewed in both the transverse and sagittal planes and the tumor boundary was fitted with an ellipse in each view measuring $D_1$ or $D_3$ and the depth $D_2$. Tumor volume was then calculated using the following equation:

$$V = \frac{\pi}{6}(D_1 \times D_2 \times D_3)$$

where $D_2$ is the average of depth measured in each transverse and sagittal view. (2)

Pharmacokinetics and Diodistribution of Copper-Doxorubicin Liposomes

Met-1 tumor mice were injected with 130 µL of either copper-doxorubicin liposomes or copper liposomes via a 30-gauge catheter inserted to the mouse tail vein. For animals randomized to receive ultrasound, one tumor was insonified for 2 min at 42° C. post-injection. At the 5 min, 6 h, 18 h, and 24 h time points, a cohort of mice was euthanized by cervical dislocation. Blood was drawn from the heart using a heparin-treated syringe, collected into PST™ Gel tubes coated with lithium heparin (Becton Dickinson, Franklin Lakes, N.J.) and tumors were dissected. Plasma was isolated at 1200×g at 10 min at room temperature and diluted with an equal volume of water. Fluorescence intensity of doxorubicin was measured before and after incubation in the presence of 0.25% Tx-100 and 10 mM EDTA at 55° C. for 1 h using Tecan Infinite® M1000 Microplate Reader at excitation and emission wavelengths of 485 nm and 590 nm, respectively. Tumor samples were collected in 5 mL cryovials (Phenix Research, Candler N.C.) and stored at −80° C. For tumor digestion, samples were frozen in liquid nitrogen and lyophilized overnight. One milliliter of concentrated nitric acid (trace-metal-grade, 70%; Fisher Scientific, St. Louis, Mo.) was then added to the dried tumor samples and the mixture incubated for 4 hours at 60° C. and then overnight at room temperature. One milliliter of 30% hydrogen peroxide (Optima trace-metal-grade; Fisher Scientific, St. Louis, Mo.) was then added and the mixture incubated for 2 hours at 55° C. The volume was completed to three milliliters with purified DI water. Isolated plasma and digested tumor samples were analyzed for copper content using Inductively Coupled Plasma (quadrupole) Mass Spectrometry (ICP-MS, Agilent Technologies, Santa Clara, Calif.) performed at University of California, Davis/Interdisciplinary Center for Plasma Mass Spectrometry.

In Vivo Multi-spectral Fluorescence Imaging

The Maestro™ in vivo Imaging System (Cambridge Research & Instrumentation, Inc., Woburn, Mass.) was utilized. The system is consisted of a light-tight and temperature-controlled imaging chamber, a tunable multi-spectral camera system, and a computer with pre-installed software which allows accurate spectral unmixing for increased spectral contrast and improved data quantification. Each mouse was placed in the imaging chamber at 37° C., systemically injected with either free or liposomal doxorubicin, and imaged using the blue Maestro filter set (500:10:720) with the exposure time of 1000 ms. The fluorescence signals were then unmixed from the auto-fluorescence in the image cube. A region of interest (ROI) was manually selected over the signal intensity. The area of the ROI was kept constant and the intensity was recorded as average signal (photons/s/cm$^2$) within a ROI. At 24 h or 48 h post drug administration, mouse was placed under 3.5% isoflurane until asleep and then euthanized by ip injection of Euthasol (Western Medical Supply, Arcadia, Calif.) at 150-200 mg/kg body weight. Once respiration ceased, the chest cavity was opened by cutting through the ribs exposing the heart and lungs. A 29-gauge insulin syringe was then placed into the heart and a volume of blood was withdrawn. Next, a 19-gauge butterfly catheter attached to an in vivo perfusion apparatus filled with saline was inserted into the left ventricle while the right atrium was cut. The animal was perfused with 50 ml of saline until all blood was cleared from the body as noted by clear fluid running from the heart. Organs and tissues were dissected and imaged for drug accumulation. Doxorubicin concentration in blood was measured as described in the previous section in "Pharmacokinetics and biodistribution of copper-doxorubicin liposomes".

Contrast Ultrasound Imaging

Definity® microbubbles for contrast imaging were provided by Lantheus Medical Imaging (N. Billerica, Mass.). To evaluate and quantify the extent of angiogenesis in Met-1 tumors during treatment as a response to therapy, we employed a real-time parametric ultrasound imaging of vascular volume/density and flow rate implemented in the Acuson Sequoia® 512 system (Siemens Medical Solution USA, Inc., Issaquah, Wash.). After the region surrounding the tumor was shaved, each Met-1 tumor mouse was injected intravenously with Definity microbubbles (~1-3×10$^8$ microbubble/mL saline) via a 27-gauge catheter at 1.8 mL/h to obtain a clinically relevant blood pool concentration of 10$^6$ microbubbles/mL. Each tumor was positioned in the sagittal plane, to match the orientation with histology images, and viewed with a 15L8-S linear array transducer working in 7 MHz. Parametric maps of replenishment were acquired in real-time using Siemens Cadence Contrast Pulse Sequencing (CPS) system with a motion sensing probe (MSP) at CPS Gain –15, 028 MI (Mechanical Index) (Pollard, R. E.; Dayton, P. A.; Watson, K. D.; Hu, X. W.; Guracar, I. M.; Ferrara, K. W., Motion Corrected Cadence CPS Ultrasound for Quantifying Response to Vasoactive Drugs in a Rat Kidney Model. *Urology* 2009, 74, (3), 675-681). The system induced high-MI destructive pulses (7 MHz, 1.9 MI) to fragment microbubbles in the tumor region, then estimated the inflow of microbubbles over 10-second duration and generated the corresponding parametric image. In the parametric image, yellow represented fast replenishment, pink very slow replenishment. The CPS images and the corresponding quantitative image were stored in Sequoia 512, and then were processed off-line in MATLAB® (Mathworks, Natick, Mass.) to calculate the mean flow replenishment time and its distribution. In the post-processing algorithm, a ROI was manually selected to include the tumor.

Therapeutic Ultrasound

The tumor temperature feedback was accomplished using a 30-gauge needle thermocouple (HYP-1, Omega Engineering, Inc., Stanford, Conn.), which was inserted into the center of the tumor and interfaced to a data acquisition system controlled using LabVIEW™ (National Instruments Corp. Austin, Tex.) running on a PC. A proportional-integral differential control (PID) system was used to maintain the tumor temperature at 42° C. for 2 min by controlling the transmitted output power on the ultrasound scanner. The therapeutic beam was swept in the azimuth dimension to fit the tumor dimensions. The animal's core temperature was monitored using a rectal thermocouple and was maintained at ~37° C. during the experiment (Kheirolomoom, A.; Dayton, P. A.; Lum, A. F. H.; Little, E.; Paoli, E. E.; Zheng, H. R.; Ferrara, K. W., Acoustically-active microbubbles conjugated to liposomes: Characterization of a proposed drug delivery carrier. *Journal of Controlled Release* 2007, 118, (3), 275-284).

Positron Emission Tomography (PET) and Optical Imaging

Dual labeled liposomes were prepared as previously described (QinSP, An image-driven model for liposomal stability and circulation. *Mol Pharamceutics* 2010, 7, (1), 12-21). Briefly, benzyl-TETA(6-{p-(bromoacetamido)benzyl}-1,4,8,11-tetraazacyclotetradecane-N,N',N''',N''''-tetraacetic acid) (BAT) conjugated to a distearoyl lipid with PEG-1200 as a spacer was used as the $^{64}$Cu chelator. A hydrophilic near-infrared fluorophore Bis-1,1'-(4-sulfobutyl)indotricarbocyanine-5,5'-dicarboxylic acid (SIDA) was loaded into aqueous core of the liposomes to label the liposomal core. Long-circulating liposomes containing 0.5 mole % BAT-lipid were prepared in the presence of 1 mM SIDA. PET and optical images (IVIS Caliper System, Caliper Life Sciences Corp. Alameda, Calif.) were acquired separately at 0, 6, 18, 28, 48 h following systemic injection of 1 mg of liposomes containing ~400 µCi.

Immunohistochemistry

Tumors and selected organs were fixed with 10% Formaldehyde and processed for H&E and immunohistochemistry by the University of California, Davis, Pathology Laboratory. Paraffin sections of 4 µm thickness were stained with Mayer's H&E or immunostained with anti-Ki-67, anti-cleaved caspase 3, and anti-CD31. Total nuclei, CD31-positive area and number of caspase 3-positive cells were quantified using the Aperio's image-analysis algorithms (Aperio Technologies, Vista, Calif.).

Statistical Analysis

Data points represent the average of triplicate measurements and the error bars are the standard deviations of the triplicate measurements. Statistical analyses between group pairs and among multiple groups were performed using the two-tailed t-Test assuming unequal variances, and one-way ANOVA followed by a Tukey Post Hoc test, respectively. For comparison among groups over the treatment period, we fitted mixed models to the tumor growth curve data (FIGS. 5a and 5b), estimating trajectories using a log transformation of tumor volume at each time point to reflect the exponential growth rates observed. We compared treatments by an overall likelihood test for differences in slopes across treatments, at level 0.05, to preserve the Type I error rate. When a pattern of significant differences between groups was indicated by this test, we used an orthogonal decomposition to compare the growth rates and test for specific effects of each component of the treatment combinations (doxorubicin, liposome preparation, ultrasound, and rapamycin).

Statistical significance was set at $p<0.05$. The statistical differences are represented as *$p<0.05$, $p<0.01$, and *$p<0.001$.

Example 1

Figure 7:
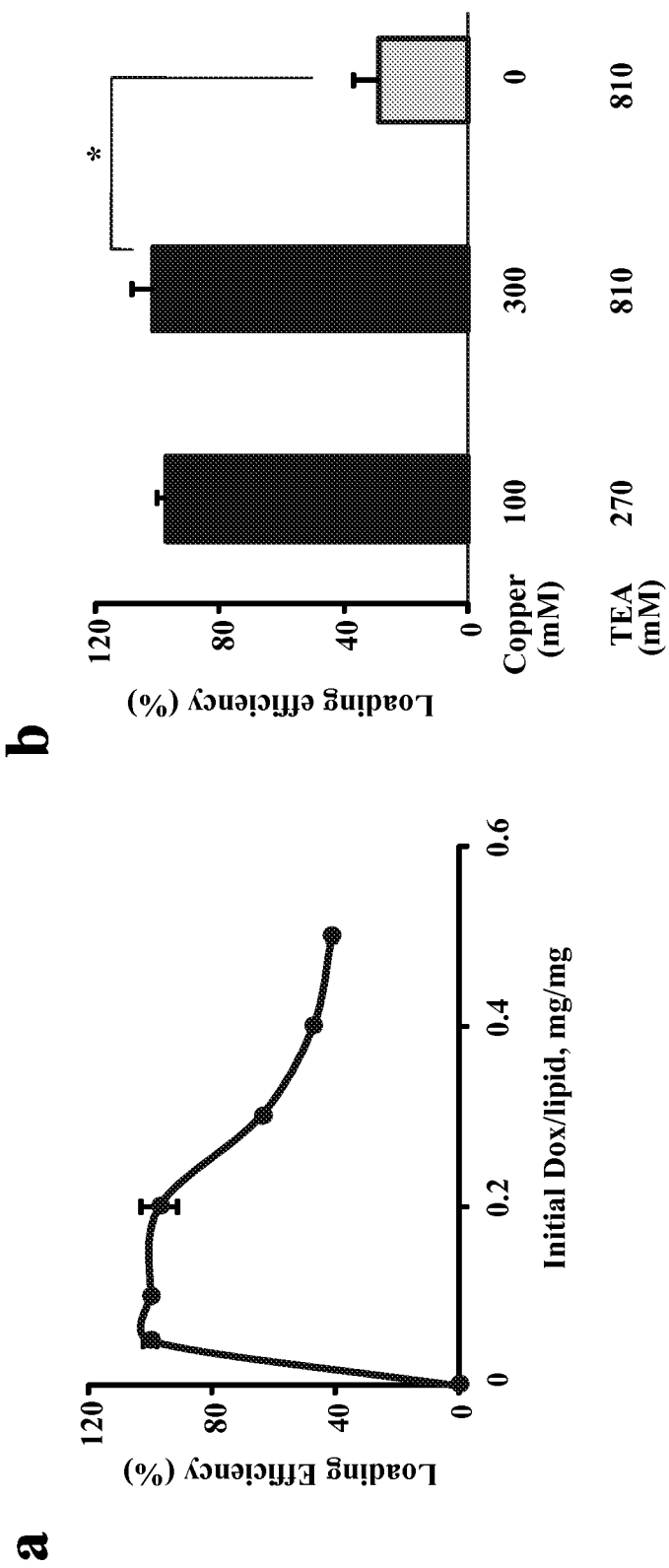
FIG. 7. a, Loading efficiency of doxorubicin loaded into 100 mM Cu/270 mM TEA liposomes as a function of initial Dox/lipid ratios at the optimized copper/TEA ratio of 100 mM/270 mM. b, Effect of copper versus TEA on loading efficiency of Dox. Statistical analysis was done by Student's t-test. c, Final Dox/lipid ratios as a function of intraliposomal copper concentration. d, Cell viability as a function of serial dilutions of doxorubicin. *p<0.05.
Figure 7:
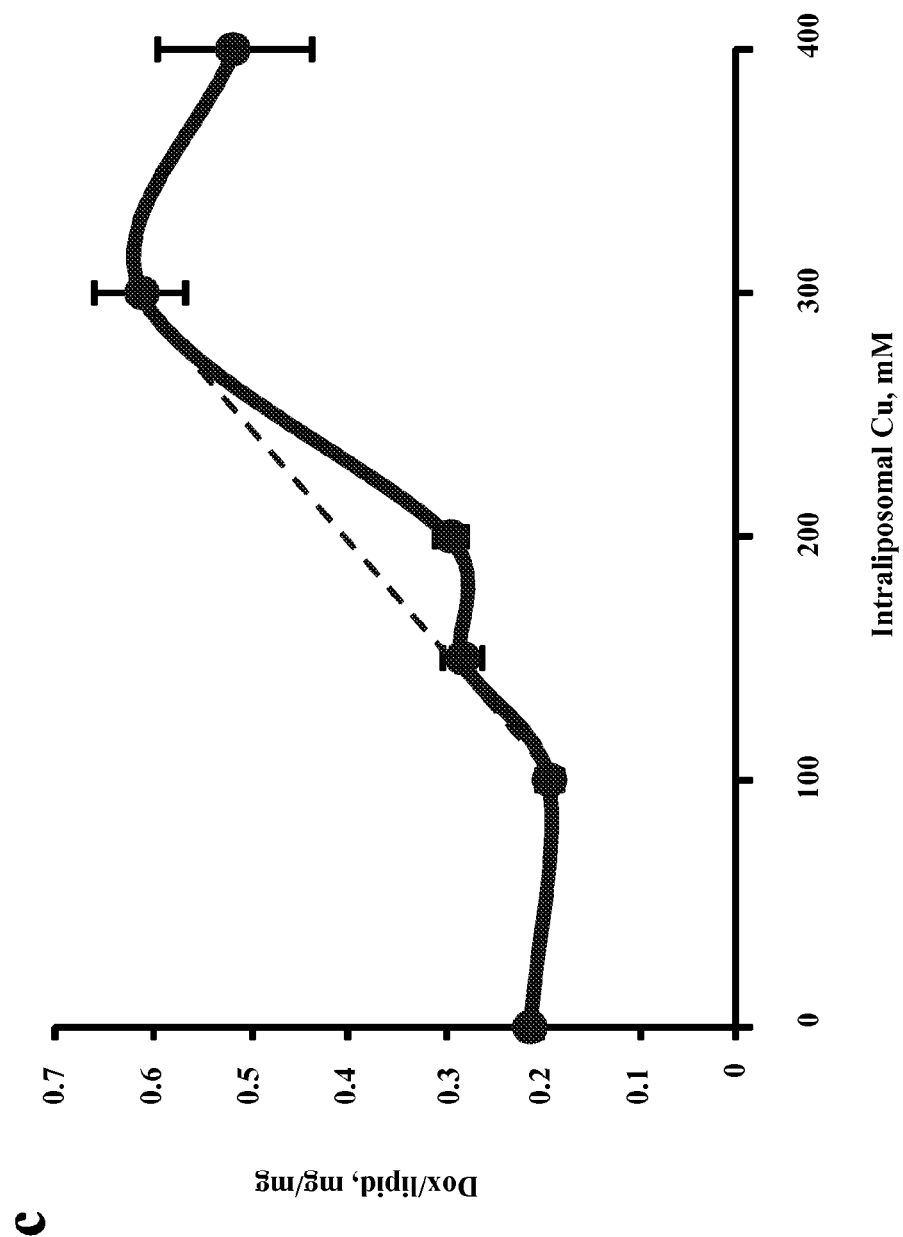
Figure 7:
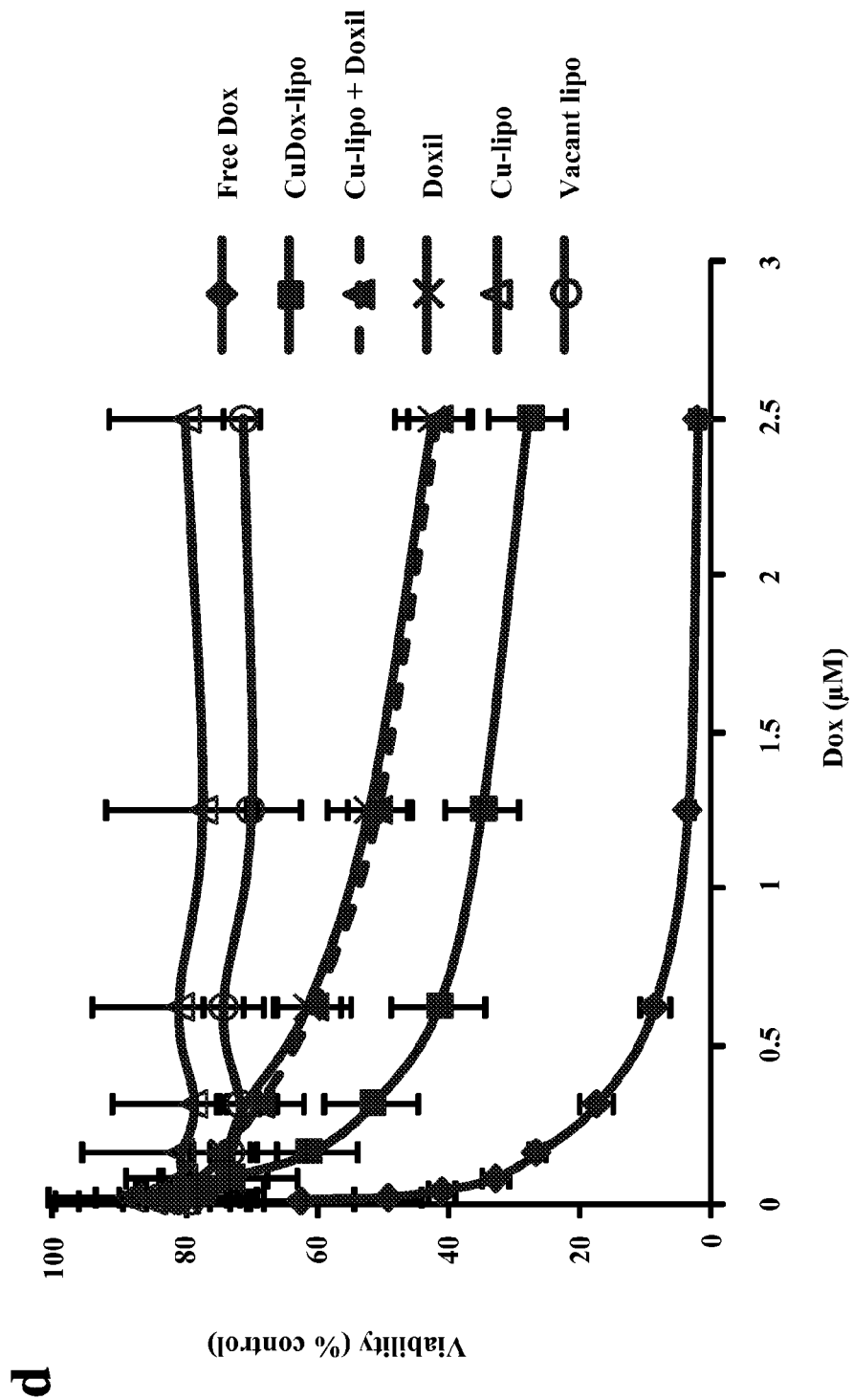

Copper-doxorubicin Complex Quenches Fluorescence and Demonstrates Enhanced Stability at Neutral pH Doxorubicin loading increased with the ratio of copper to doxorubicin, reaching a maximum at a 1:2 molar ratio with 100% loading efficiency (Methods and FIG. 7). Loading also increased linearly with the intra-liposomal copper concentration, up to 0.6 mg doxorubicin per mg lipid (FIG. 7c). In all following studies, particles were loaded using 100 mM copper-gluconate and 270 mM TEA, achieving a final ratio of 0.2 mg-doxorubicin per mg-lipid in order to facilitate a comparison with Doxil.

Although doxorubicin loading increased in proportion to the TEA gradient, intra-liposomal doxorubicin fluorescence was quenched (FIG. 1a). For copper-doxorubicin liposomes, full restoration of doxorubicin fluorescence was observed only with the combination of Triton X-100, trans-chelation with EDTA and incubation at 55° C. for 1 hour, indicating that doxorubicin was associated with copper (FIG. 1a-b). Even in the presence of serum albumin, EDTA and elevated temperature were required to achieve trans-chelation and restore fluorescence (FIG. 1b). Alternatively, for liposomes that did not contain copper, the fluorescence intensity of released doxorubicin was not affected by the addition of EDTA (FIG. 1a-b). Long term in vitro stability of doxorubicin encapsulation was also assessed; free doxorubicin was not detected during a 30-day in vitro incubation of either copper-doxorubicin liposomes or Doxil at 37° C.

Fluorescence of both Doxil and copper-doxorubicin liposomes in plasma remained quenched after 24 hours of circulation (FIG. 1c). Upon addition of Triton X-100, fluorescence of doxorubicin was fully restored for Doxil, whereas, a combination of Triton X-100 and EDTA at elevated temperatures was required to restore the fluorescence of doxorubicin for copper-doxorubicin liposomes as shown previously in the in vitro stability assay (FIG. 1b). Thus, the copper-doxorubicin complex circulates stably within liposomes and remains associated in plasma after release from liposomes. Trans-chelation kinetic of copper from copper-doxorubicin complex in the presence of albumin, one of the major trans-chelating component of blood, was strongly dependent on pH and exhibited a significantly lower dissociation rate (≤20%) at pH values of 7 and higher over a period of 48 h, $p<0.001$ (FIG. 1d). In contrast, copper trans-chelation increased as the pH decreased below 7 with a rapid dissociation of copper (≥75%) observed at pH≤5 (FIG. 1d).

Figure 2:
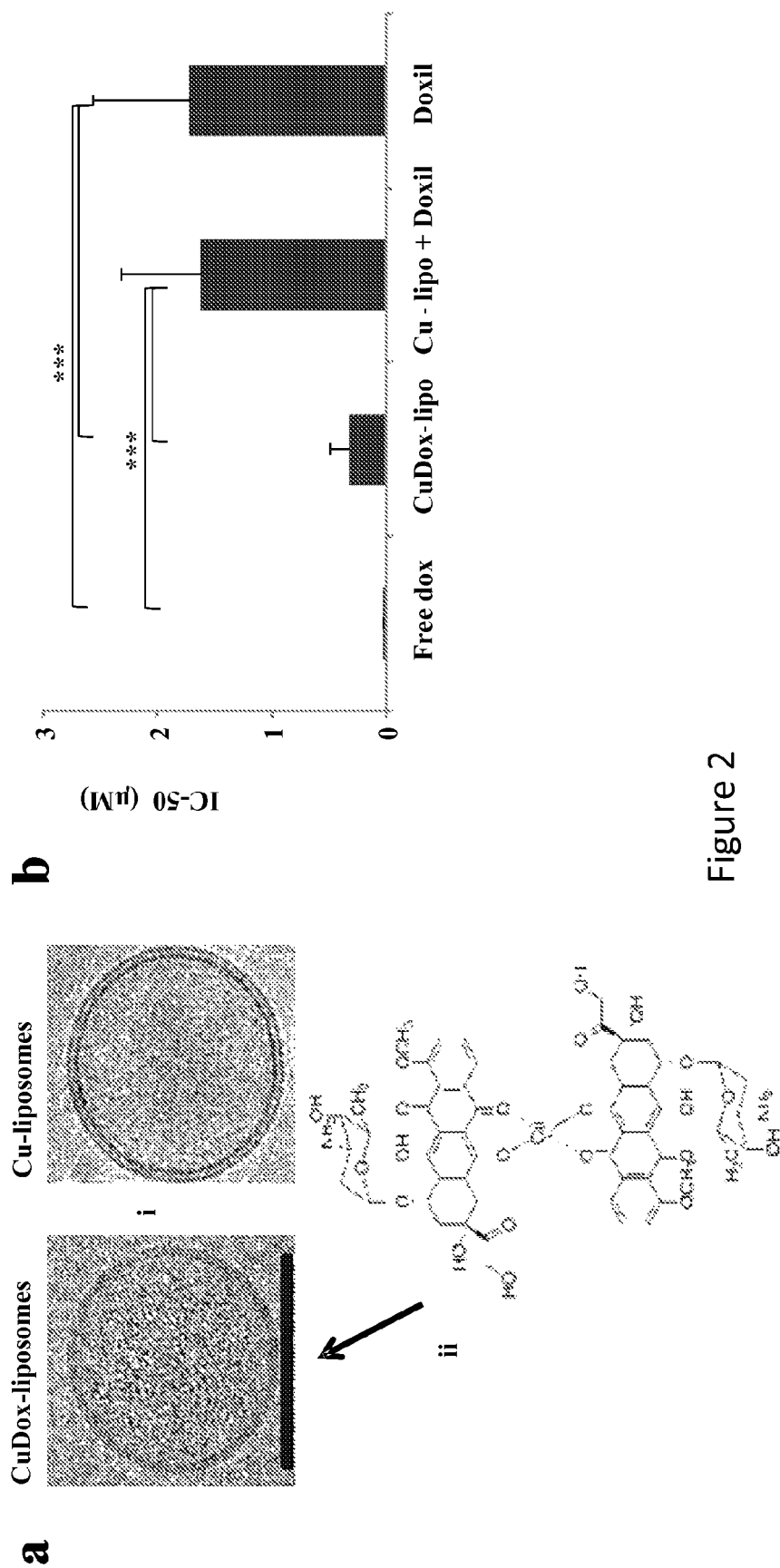
FIG. 2. Pharmacokinetics of copper-doxorubicin liposomes and comparison with control carriers. a, i, Cryo-EM images of LCLs encapsulating copper-doxorubicin (left panel) and copper only (right panel) under 100 mM copper/270 mM TEA intraliposomal condition. Scale bar represents 100 nm. ii, Schematic presentation of the hypothesized molecular interaction between copper and doxorubicin upon loading into liposomes. b, IC50 values of free and liposomal doxorubicin were calculated using GraphPad. c, Ex vivo hyper-spectral fluorescence intensity of the organs of mice 24 h after injection of copper-doxorubicin (CuDox) liposomes or Doxil. Mice were perfused with saline immediately prior to organ harvesting and imaging. Inset view of heart fluorescence at 48 h after injection (white indicates higher fluorescent intensity). d, In vivo hyper-spectral fluorescence intensity of the skin of mice after injection of CuDox liposomes or Doxil. Statistical significance is compared to the highest value in each time point. Inset images acquired at 24 h after injection. Statistical analyses were performed using one-way ANOVA followed by a Tukey Post Hoc test (b, d) and Student's t-test (c). *p<0.05, p<0.01, *p<0.001.
Figure 2:
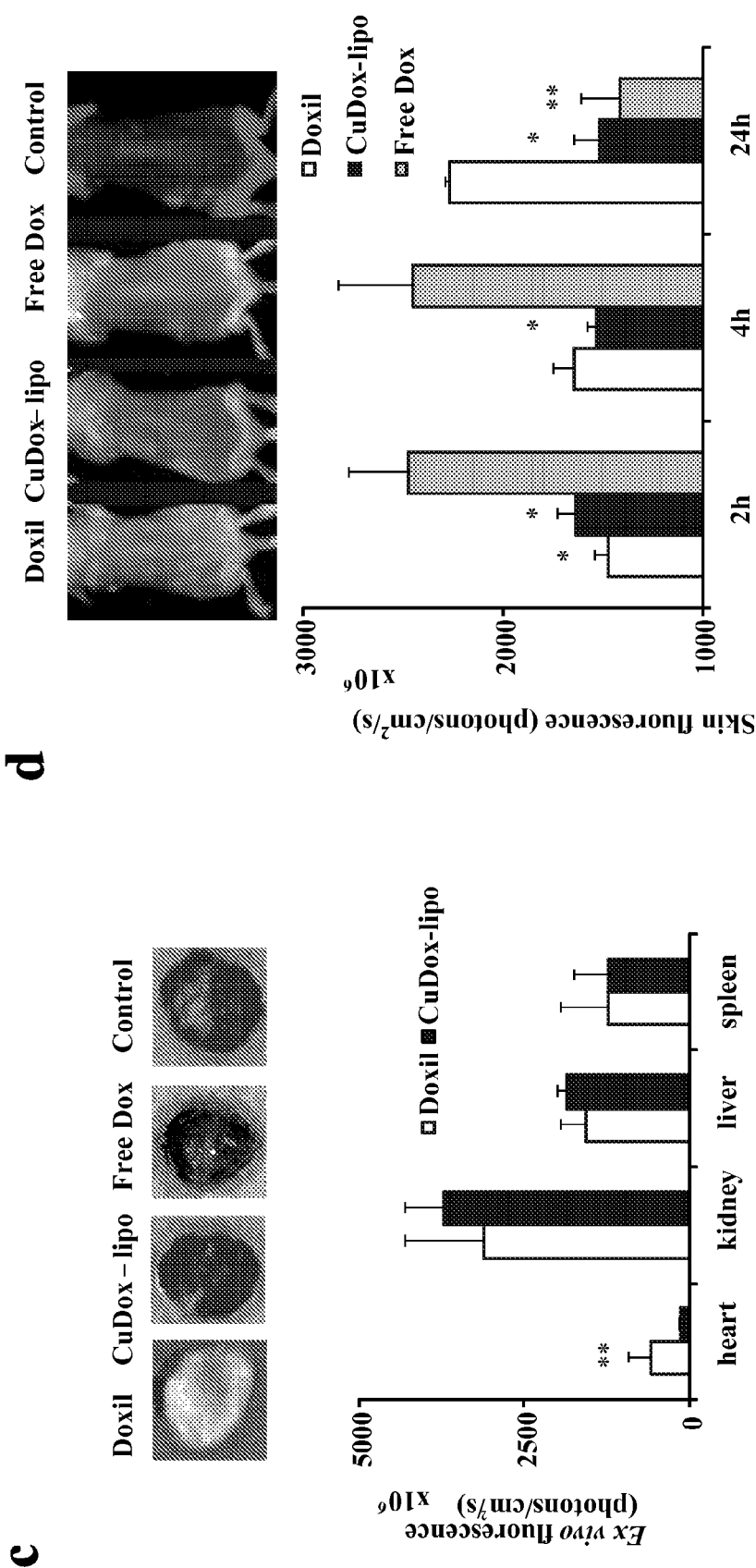

Cryo-electron microscopy verified the presence of precipitation as a dotted and diffuse structure of the copper-doxorubicin complex uniformly distributed inside the liposomes (FIG. 2a-i left), which was substantially different than the needle-like precipitate formed by ammonium sulfate loading of doxorubicin[31, 32] or the subtle precipitate of copper alone (FIG. 2a-i right). Given the molar ratio of 1:2, the hypothesized structure for the liposomal copper:doxorubicin complex is schematically depicted (FIG. 2a-ii).

Example 2

In Vitro Cytotoxicity of Copper-doxorubicin Liposomes is Enhanced

When evaluated with the Met-1 cell line, the cytotoxicity of the copper-doxorubicin liposomes (IC50 of 0.33±0.16 µM, n=12) was greater than that of Doxil (IC50 of 1.72±0.85 µM, n=6), $p<0.001$, whereas free doxorubicin exhibited the lowest IC50 value (0.02±0.01 µM, n=15) (FIG. 2b; FIG. 7d). Empty liposomes and copper liposomes (each tested with an equal lipid concentration) had no effect on cell viability. Delivery of copper and doxorubicin in two separate liposomal formulations (copper liposomes and Doxil) did not change the IC50 value of Doxil.

Example 3

Copper-doxorubicin Liposome Stability is Associated with Reduced Systemic Toxicity In vivo stability was assessed by serial imaging of fluorescent doxorubicin, PET labeling of the liposomal shell, and ICP-MS measurements of copper accumulation. At 24 hours after the injection of copper-doxorubicin liposomes, the concentration of doxorubicin and copper in plasma were 43.3±3.8% ID/cc (n=6) and 39.1±6% ID/cc (n=6) of the initial dose, indicating a stable association of doxorubicin with copper in circulation. The concentration of doxorubicin in Doxil in the blood pool was higher 24 hours after injection with ~50% of the initial dose continuing to circulate ($p<0.01$).

Following organ perfusion with saline and excision at 24 hours after injection, fluorescence was similar for Doxil and copper-doxorubicin liposomes in organs associated with drug clearance (spleen, liver, kidney). However, in the heart, fluorescence resulting from copper-doxorubicin liposomes was one-fifth that resulting from Doxil administration, $p<0.01$ (FIG. 2c). Skin fluorescence increased to a greater extent following Doxil administration than with Cu-doxorubicin liposomes or free doxorubicin, increasing with time for Doxil and decreasing with time for free drug and Cu-doxorubicin liposomes, $p<0.05$ (FIG. 2d). A unique spectrum, associated with intact Doxil liposomes, was detected within the skin by multi-spectral optical imaging (FIG. 8a-b), indicating that the increased fluorescence resulted at least partially from intact liposomes.

Figure 3:
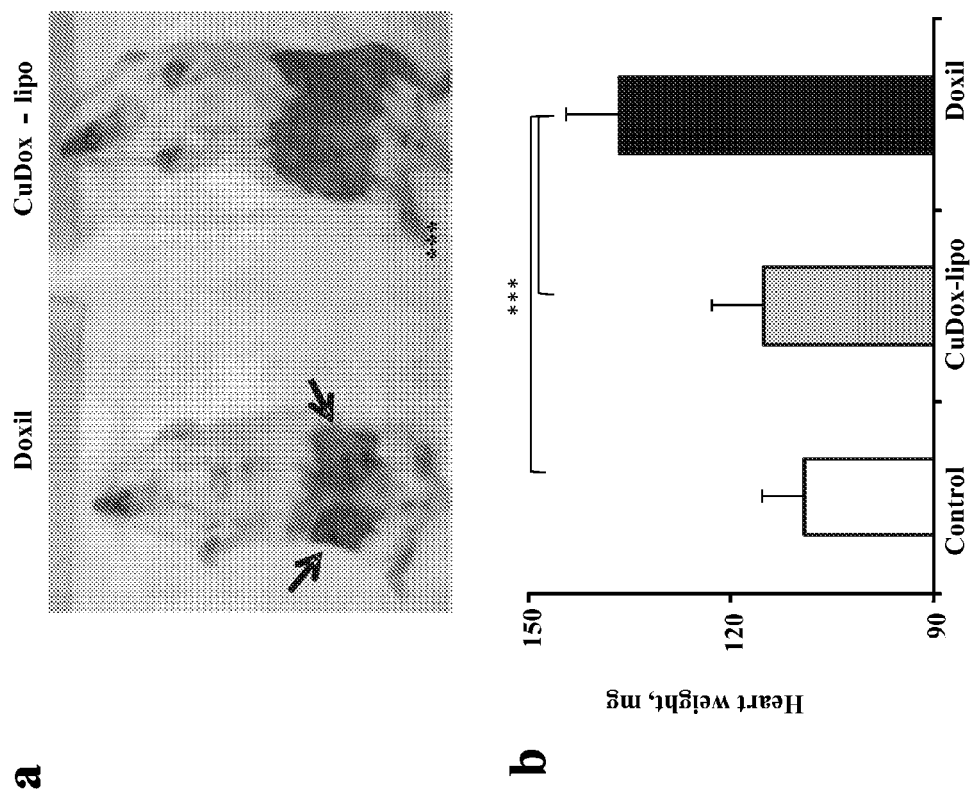
FIG. 3. Toxicity of copper-doxorubicin (CuDox) liposomes and Doxil assessed over 28 day administration of 6 mg/kg (33.4 mg/m$^2$) twice per week (total of 266.7 mg/m$^2$). a, Images of Doxil-treated and CuDox liposome-treated mice. Arrows show areas of redness over the tumor region of Doxil-treated animal. Areas of redness were generally absent or substantially reduced in the CuDox-lipo group when compared to controls. Heart weight (b) and protein (albumin and total protein) measurement (c) for mice injected with either CuDox liposomes or Doxil. d, Weight change of mice treated with either CuDox liposomes, Doxil or saline control, over 28 days of treatment. Statistical analyses were performed using one-way ANOVA at the end of the treatment period followed by a Tukey Post Hoc test. *p<0.05, p<0.01, *p<0.001.
Figure 3:
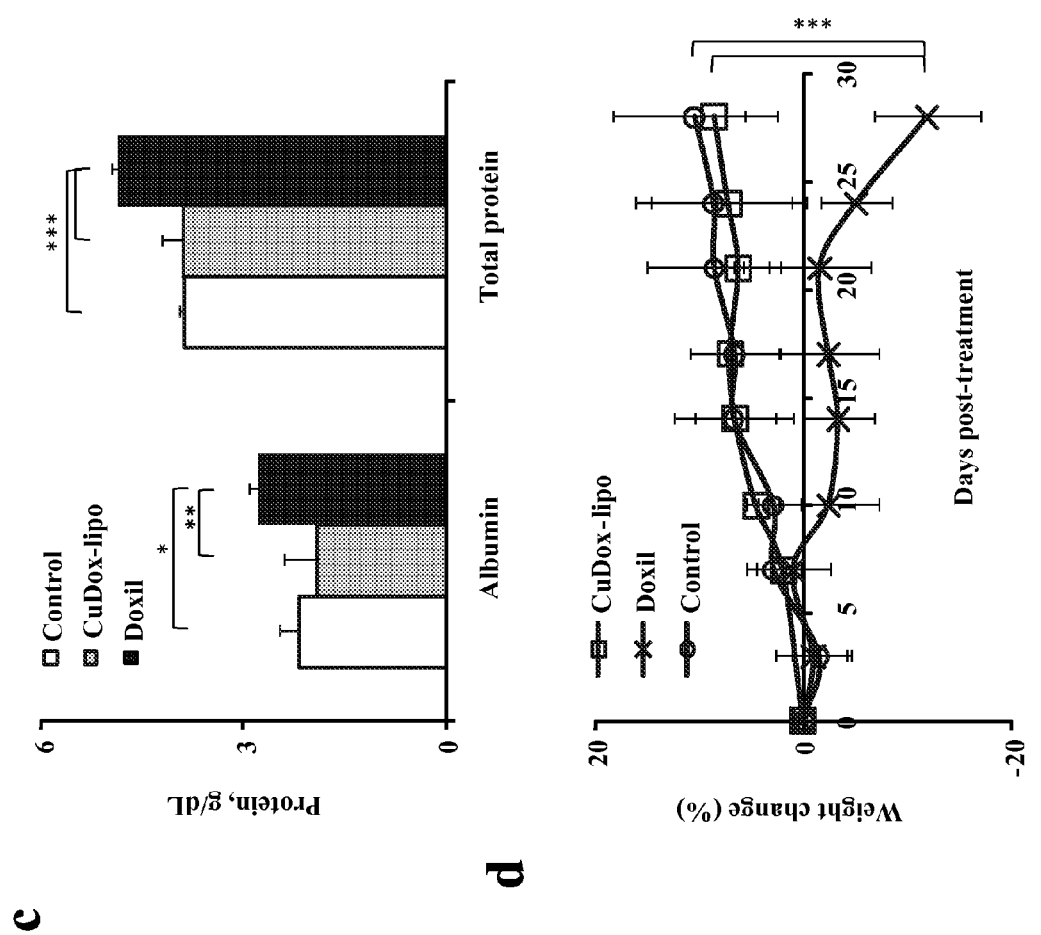

Doxorubicin-associated toxicity was then assessed with an aggressive four-week dose schedule of 6 mg/kg of doxorubicin liposomes twice per week, which is equivalent to 66.7 mg/m$^2$ per week. Animals receiving Doxil at this relatively high dose demonstrated fur loss and a skin rash as early as 7-10 days post-treatment; such effects were not observed with the equivalent dose copper-doxorubicin liposomal therapy throughout a 28-day course of treatment (FIG. 3a). Doxil-treated animals showed a significant increase in heart weight ($p<0.001$), circulating albumin ($p<0.05$) and total protein ($p<0.001$) and a significant weight loss ($p<0.001$), as compared to control mice and mice treated with copper-doxorubicin liposomes (FIGS. 3b, 3c, 3d). Leucopenia was observed with each liposomal doxorubicin group; however, the effect was greater with Doxil. Red and white blood cell counts following the administration of a control diluent, copper-doxorubicin liposomes or Doxil were 7.6±0.7 (n=5), 4.5±0.3 (n=7), 3.1±0.1 M/µL (n=5) for red blood cells and 5.7±2.1, 3.6±1.1, 1.9±0.6 K/µL for white blood cells, respectively.

Example 4

Efficacy of Copper-doxorubicin Liposomes Demonstrated in Multi-component Regime

Figure 4:
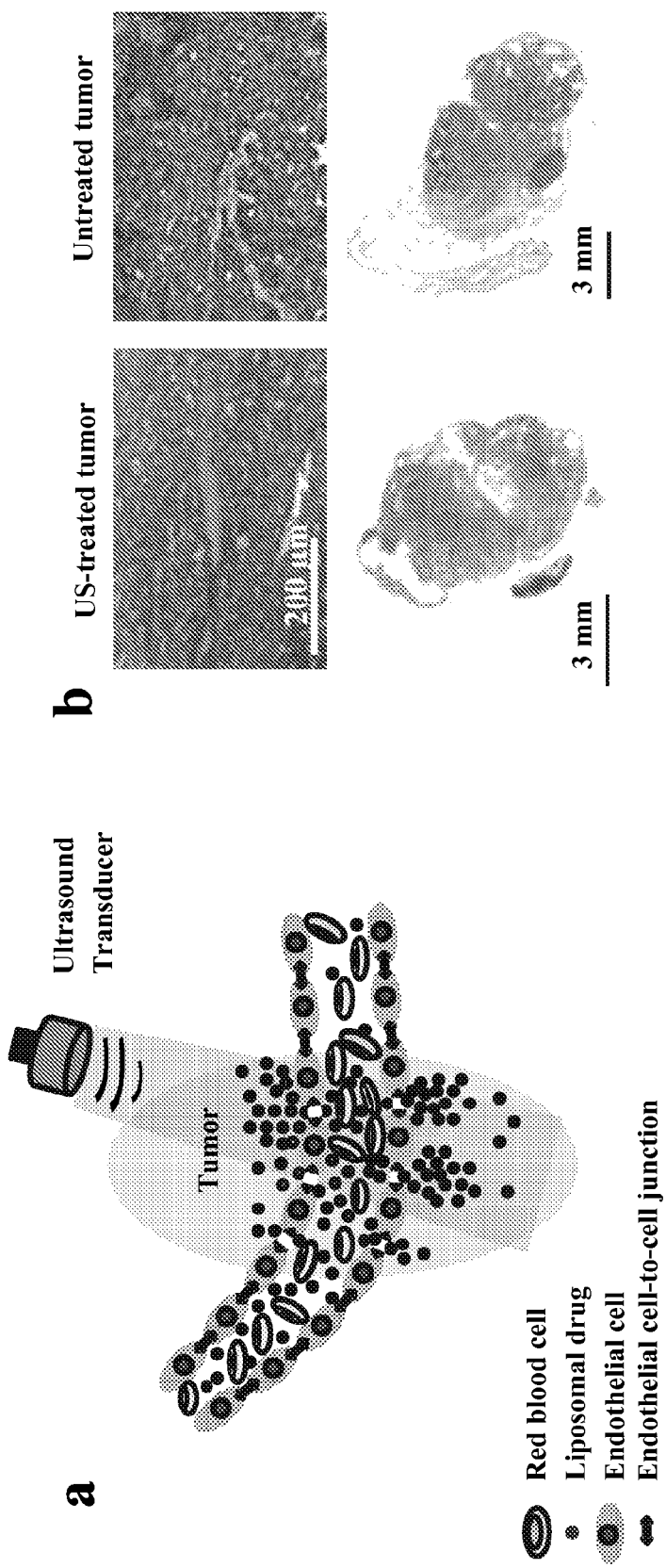
FIG. 4. Enhanced accumulation of copper-doxorubicin liposomes using therapeutic ultrasound (US). a, Concept image of locally-enhanced extravasation and accumulation of liposomal chemotherapeutic in solid tumors by ultrasound. b, H&E histological images of insonified tumor (upper left panel) compared to untreated tumor (upper right panel) demonstrating vascular dilation and engorgement produced by ultrasound, tumor insonified for 2 min at 42° C. over a 10 day period of treatment with insonation repeated at day 1, 4, and 8 (lower left panel) compared to untreated tumor with the same period of treatment (lower right panel). c, Blood stability and tumor accumulation of the lipid shell of LCLs quantified by Positron Emission Tomography (PET) and compared with stability of copper-doxorubicin in blood as quantified by copper (ICP-MS) and indicated by % injected dose.
Figure 4:
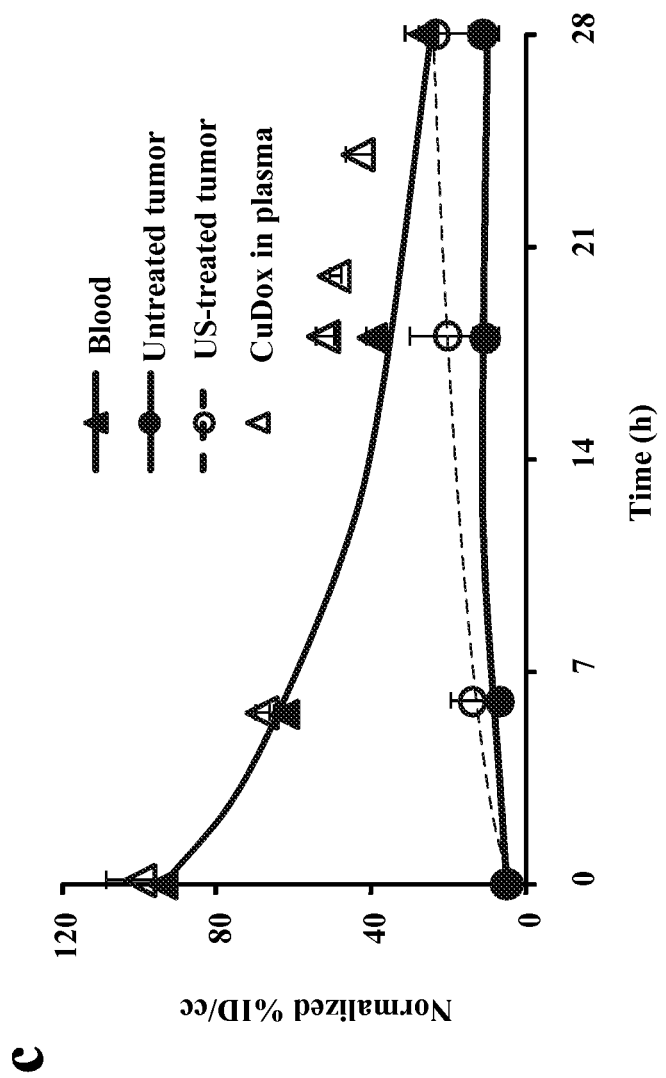

In initial studies with copper doxorubicin liposomes or Doxil with 3 mg/kg (~17 mg/m$^2$) biweekly dosing, growth of the Met-1 tumor continued with only a small extension of survival (data not shown). Thus, the dose was increased to 6 mg/kg (~33 mg/m$^2$) and the treatments were incorporated into a multi-treatment regime with rapamycin, which is also known to be efficacious in the Met-1 line. Also, we recognize that the penetration of liposomal particles within solid tumors is problematic and, thus we added ultrasound to improve the accumulation and diffusion of the particles and drug within the tumor. In our study, ultrasound was applied immediately after injection, with a goal of increasing tumor accumulation (FIG. 4a). With the mechanical index (MI) of 0.9 applied here, changes in vascular permeability are not produced when short (1-2 cycle) imaging pulses are applied; however, in this study, long pulses were employed and controlled such that an increase in tumor temperature to 42° C. was achieved and maintained for two minutes. Immediately after insonation, the tumor blood vessel diameter increased to 25.5±25.3 µm (n=4, FIG. 4b, upper left panel) as compared to 11.6±6.9 µm for untreated tumors (n=4, FIG. 4b, upper right panel), $p<0.001$. In the absence of drug, insonifying one of two bilateral tumors did not change the tumor growth rate (FIG. 4b, lower panels).

Figure 8:
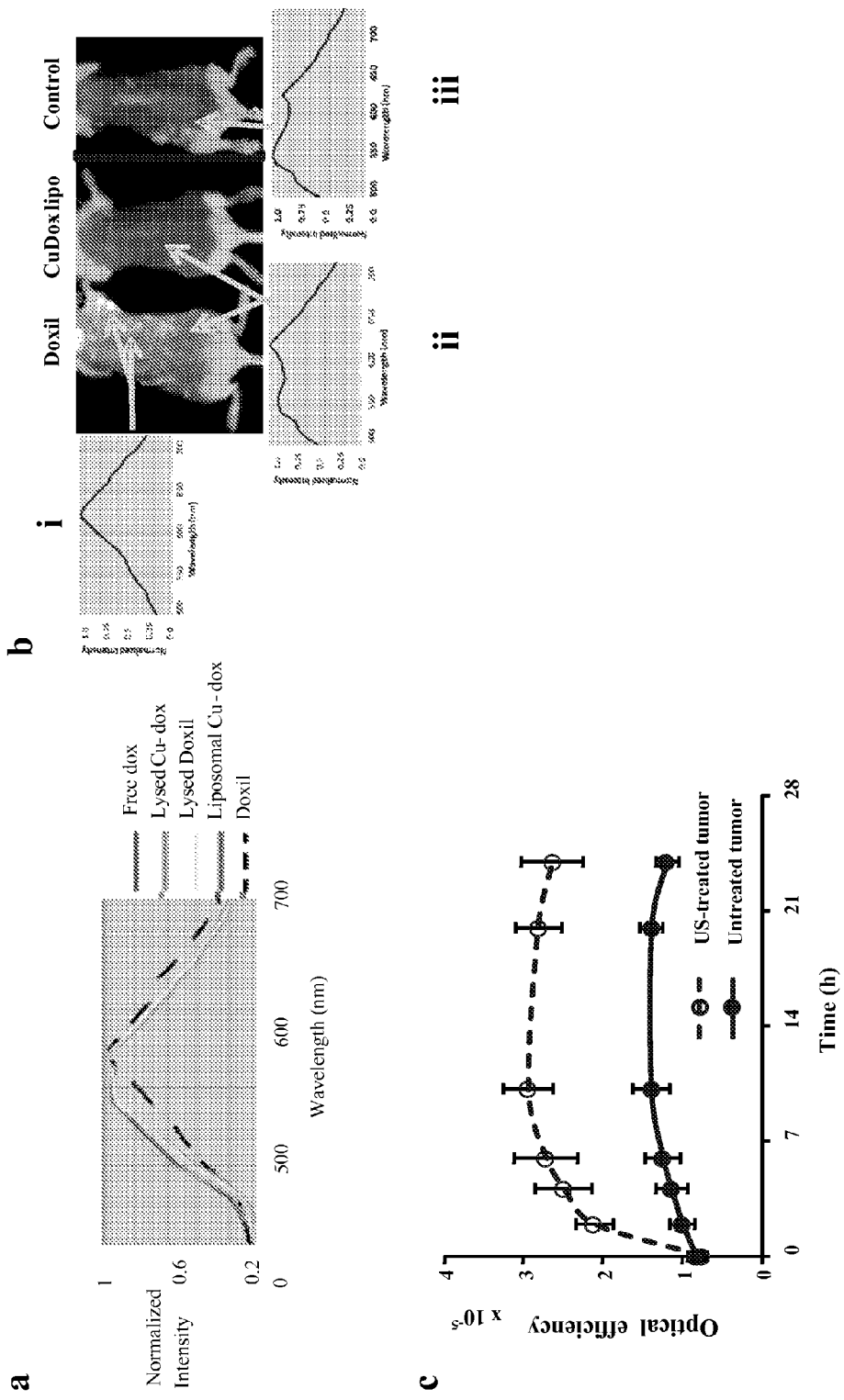
FIG. 8. a, Spectra recorded in vitro for Doxil (intact and lysed), copper-doxorubicin liposomes (intact and lysed) and free doxorubicin, b, Skin fluorescence of segmented fluorophores with distinct spectra for i) intact Doxil, ii) free doxorubicin or CuDox liposomes, and iii) auto-fluorescence of organs. c, Plasma stability and tumor accumulation of an encapsulated fluorophore monitored by optical imaging. Ultrasound increases the accumulation of the fluorophore in the drug core and the PET label on the shell.

As assessed with PET and optical imaging, the concentration of liposomes within the tumors peaks between 18 and 20 hours after injection (FIG. 4c FIG. 8c). Copper (assessed by ICP-MS) accumulated in tumors similarly over time, reaching a maximum of 10% ID/g at 18-20 h post-injection. The concentration of liposomes within the insonified tumor increased by approximately 2-fold compared with the contralateral tumor, as quantified using PET (FIG. 4c) and optical imaging (FIG. 8c). Further, the concentration of copper also increased by approximately two-fold in the insonified tumor, reaching a maximum of 15% ID/g which translates to 20 µg-doxorubicin/g-tumor, $p<0.05$. Doxorubicin fluorescence was also evident within tumors, increasing as a function of time following the injection of both Doxil and copper-doxorubicin formulations.

Figure 5:
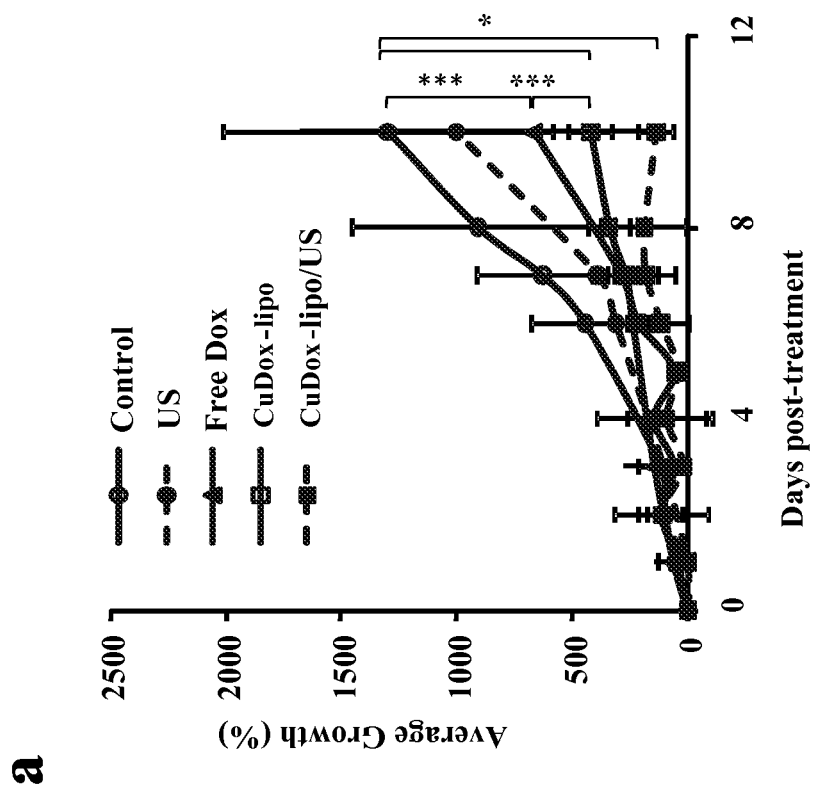
FIG. 5. In vivo treatment efficiency including ultrasound (US), free doxorubicin (free Dox), rapamycin and copper-doxorubicin liposomes (CuDox-lipo) in Met-1 tumor mice. a, b) Percent tumor growth as a function of days post-treatment, over 11-day treatment cycle (a), over 28-day treatment cycle (b). Initial tumor diameter was 4-6 mm. Each mouse was injected intravenously with either free or liposomal doxorubicin (~6 mg doxorubicin/kg body weight equivalent to ~33 mg/m$^2$) and compared to control animals that received either iv injection of saline (a) or intraperitoneal (ip) injection of diluent (b). A subset of animals was treated by ip injection of ~0.9 mg rapamycin/kg body weight three times per week over the entire period of treatment. For treatment with therapeutic ultrasound, one tumor per animal was insonified for 2 min at 42° C. post-injection. Statistical analyses were performed using mixed models as described in the Statistical analysis section. *p<0.05, p<0.01, and *p<0.001 are the significance between growth curves. H&E (c) and immunohistochemical quantification of total nuclei (d) of tumors treated with therapies post 28 days of treatment compared to control at 18 days post ip injection of diluent. Statistical analyses were performed using one-way ANOVA followed by a Tukey Post Hoc test (d). p<0.01, *p<0.001. Grey arrows indicate lymph nodes within fat pad, black arrows indicate remaining tumor.
Figure 5:
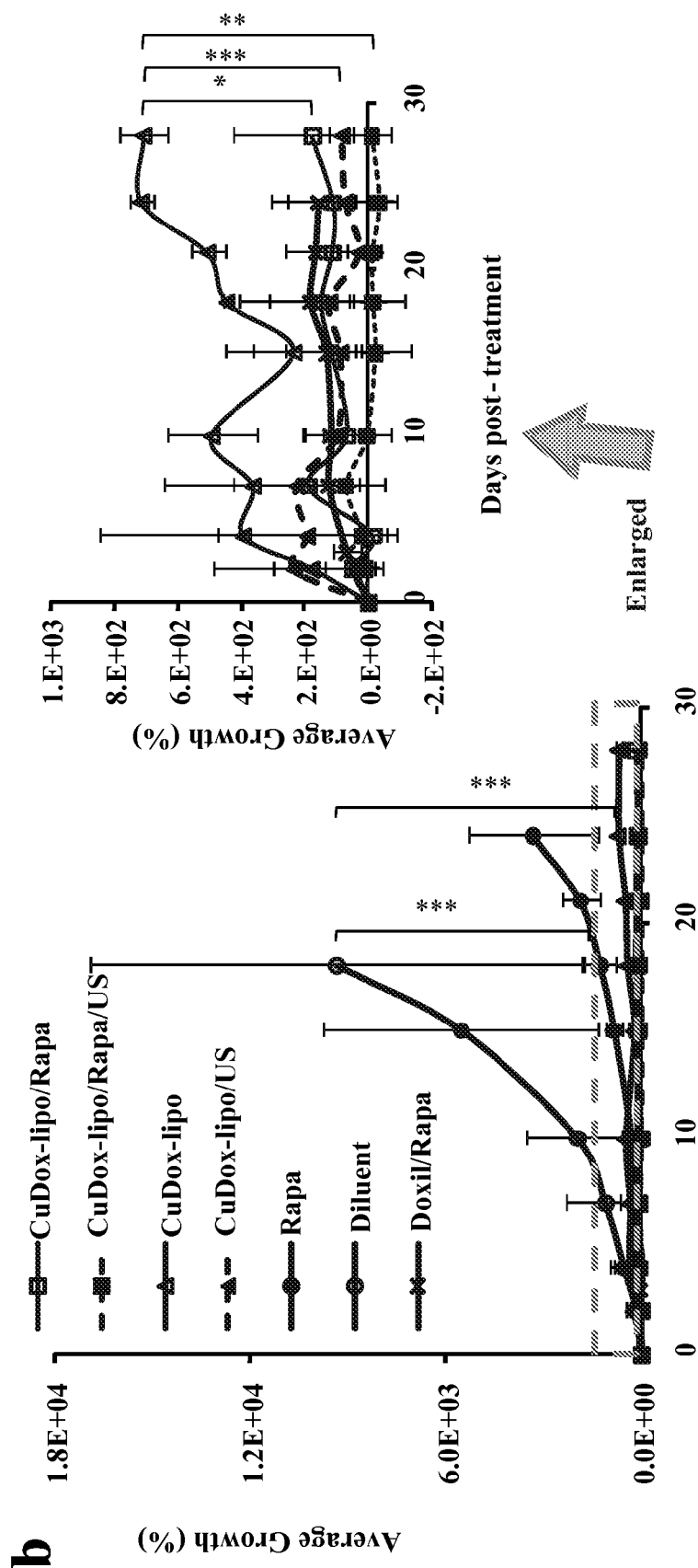
Figure 5:
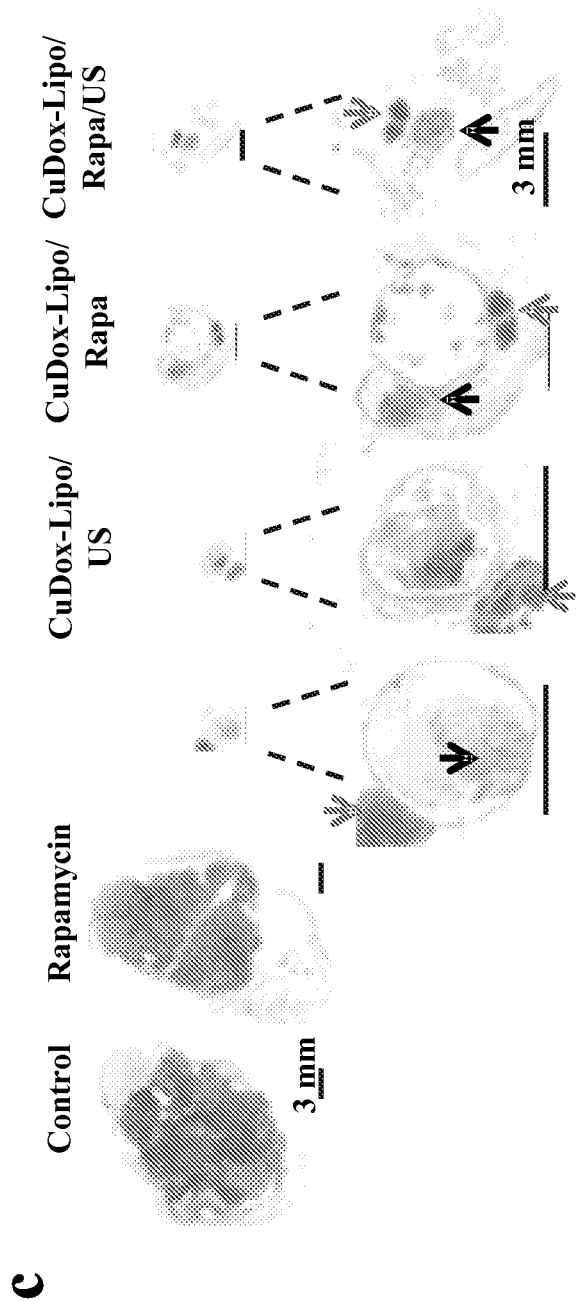
Figure 5:
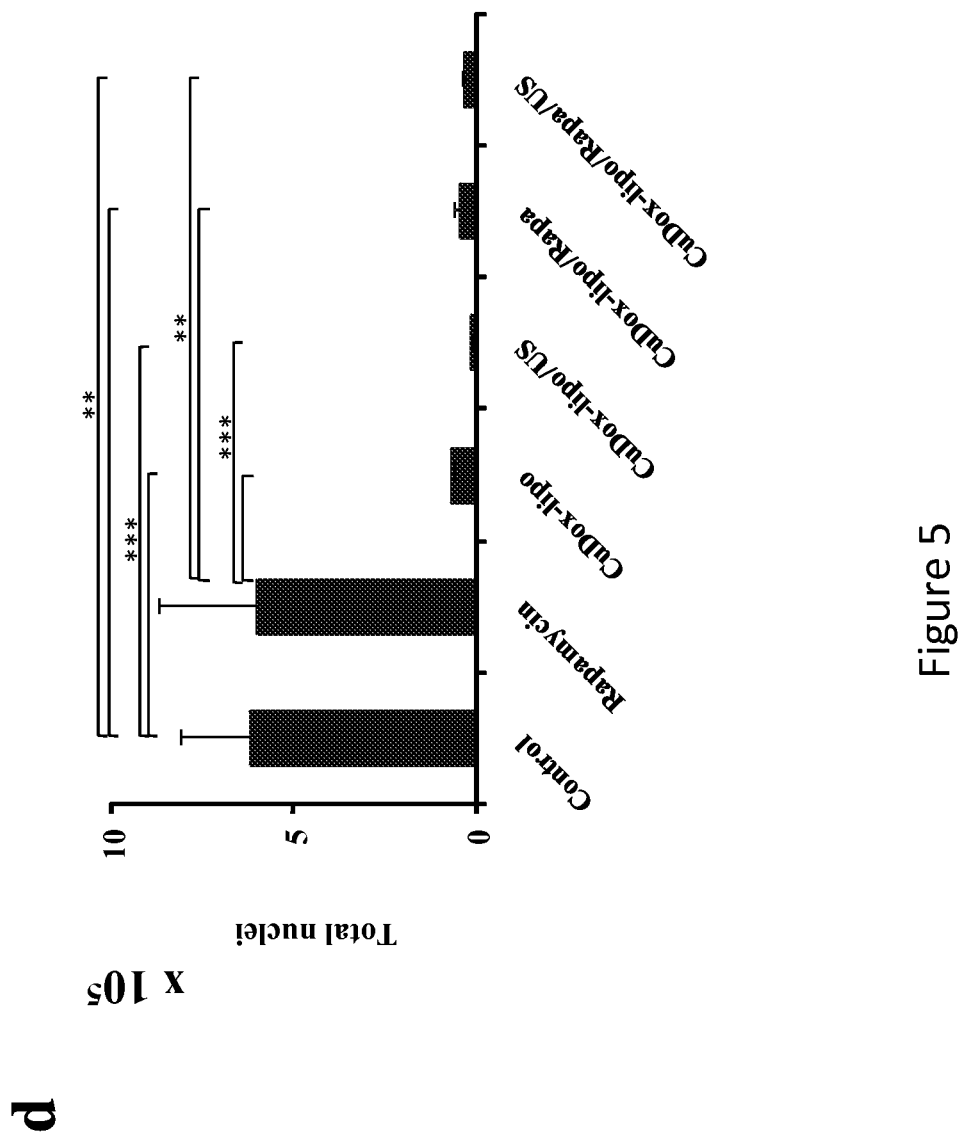

A ten day course of therapy was next applied to compare the efficacy of free doxorubicin, copper-doxorubicin liposomes (with and without ultrasound), ultrasound only, and systemic injection of a saline control therapy (FIG. 5a). The treatment with free doxorubicin showed a therapeutic effect when compared with the saline control ($p<0.001$). Tumor growth suppression was greater for copper-doxorubicin liposomes than free doxorubicin ($p<0.001$).

The therapeutic effect of copper-doxorubicin liposomes was then tested in an aggressive multi-dose 28-day treatment, in combination with rapamycin and ultrasound and appropriate single therapy control groups. Tumor longitudinal diameter ranged from 4-6 mm prior to treatment and was similar in all groups. Animals treated with diluent (control group) or rapamycin survived only 18 and 24 days post-treatment, respectively, whereas all animals receiving sole or combination therapy with liposomal doxorubicin or Doxil survived the entire 28-day course of treatment (FIG. 5b). All therapies suppressed the tumor growth as compared to control after 18 days of treatment ($p<0.001$). The in vivo efficacy of Doxil was similar to the efficacy of copper-doxorubicin liposomes in the two sub-groups that were evaluated, which were liposomal doxorubicin alone (not shown) and combined therapy with liposomal doxorubicin and rapamycin (FIG. 5b). Suppression of tumor growth was observed in all copper-doxorubicin liposome-treated animals (FIG. 5b, $p<0.001$); however, average tumor growth was ~700% with copper-doxorubicin liposomes and was reduced to <200%, 85% or –11% with the addition of rapamycin ($p<0.05$), ultrasound ($p<0.001$) or rapamycin plus ultrasound ($p<0.01$), respectively (FIG. 5b, c).

Example 5

Figure 6:
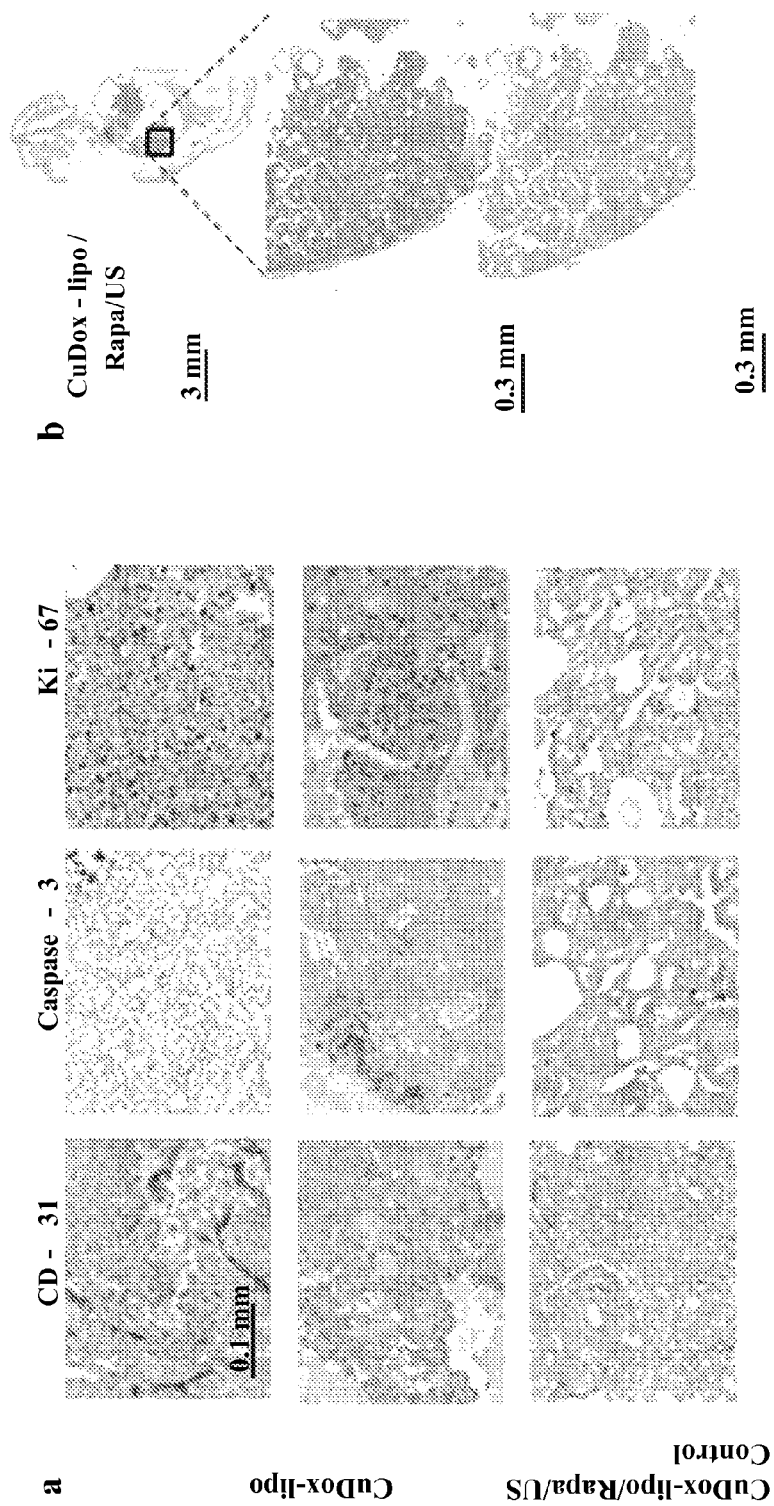
FIG. 6. Histology and immunohistochemistry of tumors treated with sole or combined therapies using copper-doxorubicin liposomes. a, Immunohistochemistry of selected tumors treated with copper-doxorubicin liposomes (CuDox-lipo) or combined therapy with rapapmycin and ultrasound (each at 28 days post onset of treatment) compared to control tumor at 18 days after ip injection of diluent. b, Histological images of a tumor treated with copper-doxorubicin liposomes combined with rapamycin and ultrasound (CuDox/Rapa/US) H&E (upper), magnified H&E of tumor indicating areas with change in tumor phenotype (middle), anti Ki-67 image (lower). c, Immunohistochemical quantification of number of vessels per unit area (i) and percent apoptotic cells (ii) across different therapies post 28 days of treatment compared to control at 18 days post ip injection of diluent. d, H&E (left), corresponding ultrasound (US) contrast agent images (middle) and parametric US images (right) from a diluent-treated control (upper panels) and CuDox/Rapa/US-treated tumor at 28-days (lower panels) with tumor is circled. In US contrast agent images, density of contrast agent (yellow; examples shown with white arrows) was proportional to vascular density. Statistical analyses were performed using one-way ANOVA followed by a Tukey Post Hoc test. *p<0.05, **p<0.01.
Figure 6:
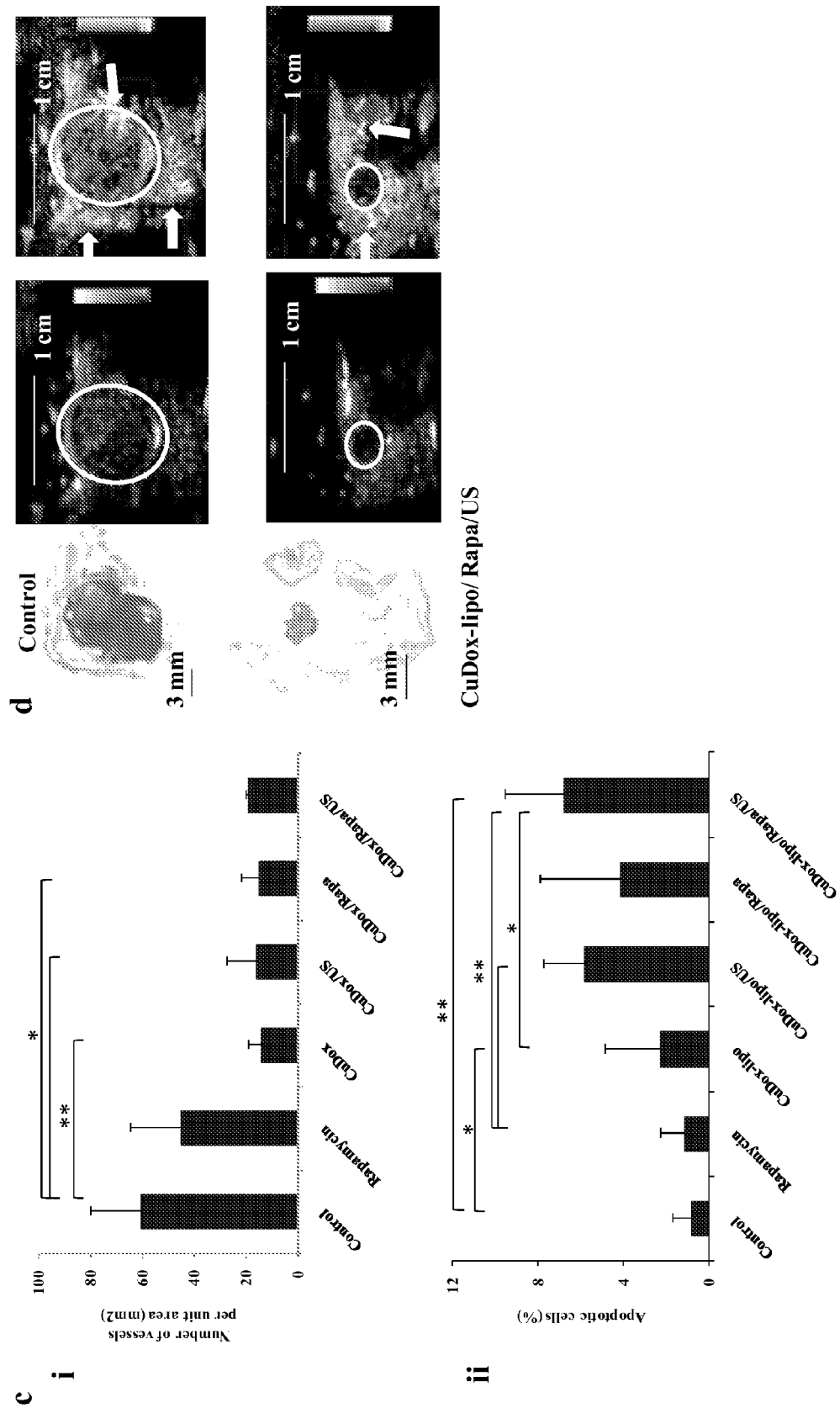

Histological Measurements Confirm Efficacy with Liposomal Doxorubicin and Enhancement with Rapamycin and Ultrasound Histological sections obtained from tumors confirmed the efficacy of therapy; however viable tumor assessed by histology was smaller than the diameter measured by ultrasound at the end of the treatment due to the presence of cysts (FIG. 5c). As a result of copper-doxorubicin liposomes and rapamycin or ultrasound therapy, a cystic, epithelial phenotype with reduced proliferation (as compared with control tumors) was observed (FIGS. 5c and 6). Mammary lymph nodes within the sections provided a control for proliferation. With the combination of copper-doxorubicin liposomes and therapeutic ultrasound, viable tumor was not detected in a subset of tumors (FIG. 5c). Total tumor nuclei were reduced in all treatments with copper-doxorubicin liposomes as compared to diluent injection, $p<0.01$ (FIG. 5d). As compared to control tumors, CD31 and Ki67 were reduced and apoptosis increased with copper-doxorubicin liposomes alone or in combination with rapamycin and therapeutic ultrasound, $p<0.05$ (FIG. 6a-c). Contrast ultrasound imaging confirmed the reduced vascularity observed in treated as compared with control tumors (FIG. 6c-i, FIG. 6d), where functional vasculature was not detected in the copper-doxorubicin liposomes plus rapamycin plus therapeutic ultrasound-treated tumors. Gold indicates the presence of contrast agent within the control tumor in the middle panels and yellow indicates fast flow within the control tumors in the right upper panel (FIG. 6d).

Discussion: Long-circulating copper-doxorubicin particles were repeatedly injected at intervals of 3-4 days without evident toxicity to skin or cardiac tissue. To simulate clinical scenarios, long-term studies of anthracycline cardiotoxicity in animals are required; we used such a study to confirm the combined efficacy and safety of our particle[7]. The treatment of highly aggressive tumors with initial volumes above 100 mm$^3$ and doubling times of a few days is challenging. Doxorubicin must be efficiently and uniformly delivered and sufficient time must be available for doxorubicin-initiated inhibition of DNA biosynthesis. Here, rapamycin reduced tumor proliferation and therapeutic ultrasound enhanced delivery; each significantly improved the efficacy of liposomal doxorubicin.

We loaded a stable drug-metal complex, rather than the free drug, and demonstrated an improved therapeutic profile. The presence of copper-doxorubicin precipitates inside the liposomes was confirmed by cryo-electron microscopy, and was distinct from the fine precipitate in copper liposomes[9] and needle-like doxorubicin crystals within Doxil[31, 32]. Doxorubicin fluorescence was quenched by the interaction of doxorubicin with copper and was restored only by the combination of liposome disruption and trans-chelation, thus confirming both the complex formation and its extended stability in circulation. In the presence of albumin, copper trans-chelation from the copper-doxorubicin complex was pH dependent; dissociation was low at physiological pH but rapid in an acidic environment. Thus, stability was optimized for minimal toxicity in circulation and maximal efficacy in tumors. The stability of the copper-drug complex was further indicated by the concentration of copper assessed by ICP-MS, which corresponded well with the doxorubicin fluorescence and liposomal shell concentration, as quantified by PET.

Toxicities associated with frequent, multiple injections of Doxil have been mitigated clinically by changes in the schedule of administration[1]. With copper-doxorubicin liposomes, the toxicity to skin, heart and other organs from multiple injections was lower than with Doxil. As in[33], no evidence of copper toxicity was detected.

We demonstrated that direct optical imaging and spectroscopy of doxorubicin is a viable tool, as also discussed in[38]. At 24-48 hours following the administration of Doxil, doxorubicin fluorescence in the skin was several times higher than with copper-doxorubicin or free doxorubicin and trends of accumulation or clearance were assessed. With the administration of Doxil, the spectrum indicated encapsulated drug within the skin and enhanced accumulation in the heart.

Insonation of one tumor with a 2-minute increase in temperature to 42° C. resulted in engorgement of blood vessels with red blood cells and enhanced the accumulation of liposomes and of copper within the insonified tumor. The resulting accumulation of ~20 µg doxorubicin/g-tumor exceeds the reported therapeutic concentration of doxorubicin[39, 40]. While ultrasound alone did not reduce tumor growth or enhance survival, the combination of copper-doxorubicin liposomes with ultrasound was efficacious (p<0.001), greatly reducing or eliminating viable tumor cells after 28 days of treatment.

The opportunity to deliver relatively large quantities of doxorubicin with reduced toxicity was exploited here to achieve a regression of our highly aggressive tumor model. The anti-tumor activity of copper-doxorubicin liposomes alone was similar to that of the ammonium sulfate-loaded doxorubicin liposomes, although with reduced toxicity. With this single therapy, tumor growth was decreased as compared with the saline control (p<0.001). Efficacy was further enhanced by the combination of copper-doxorubicin liposomes with rapamycin (p<0.05) or ultrasound (p<0.001). Altogether the results show that the copper-doxorubicin complex preserved the anticancer activity of doxorubicin, reduced toxicity, and facilitated a multi-dose strategy producing regression or tumor elimination.

Example 6

Temperature Sensitive Liposomes (TSLs)

Materials and Methods

Formation of pH Sensitive Copper-Doxorubicin Crystal Precipitate within Particles A membrane-permeable buffer, triethanolamine (TEA, pKa: 9.5, membrane permeability coefficient: 0.12 cm/s), was used to load doxorubicin within nanoparticles. A triethanolamine (TEA) gradient created across the liposomal membrane was found to be capable of loading doxorubicin efficiently in the absence of a pH gradient or a transition metal ion at neutral pH. Concentration of triethanolamine was then optimized to encapsulate 200 mM of doxorubicin inside the intra-liposomal medium. To do this, dried lipids with lipid formulations of long-circulating liposomes or temperature-sensitive liposomes were hydrated in the presence of various concentrations of TEA (90-270 mM) and 100 mOsM of saline adjusted at pH 7.4 and temperatures higher than the phase-transition temperatures of lipids used. The formed multi-lamellar liposomes were extruded using a 100 nm filter membrane to produce uni-lamellar liposomes of a 100 nm average diameter. A TEA gradient was then created across the liposomal membrane by separating free TEA from liposomes encapsulated TEA using a Sephadex G-75 column. TEA encapsulating liposomes were collected in saline and incubated with doxorubicin solution at 2 mg/ml in saline at initial Dox/lipid mass ratio of 0.2 mg/mg at 37° C. for 1.5 h for non-cholesterol-containing liposomes and overnight for cholesterol-containing liposomes. A loading efficiency of 100% was obtained for doxorubicin when TEA concentration increased to 270 mM.

To form a copper-doxorubicin complex of molar ratio of 1:2 at neutral pH, liposomes were prepared in the presence of 100 mM copper (membrane permeability coefficient: ~$10^{-11}$ cm/s), in the form of copper sulfate or copper gluconate, and 270 mM TEA with pH adjusted to 7.4. Copper/TEA liposomes were separated from free copper and a TEA gradient was generated across the membrane; liposomes were incubated in the presence of doxorubicin at 2 mg/ml in saline as explained above. Crystal formation between copper and doxorubicin (100 mM: 200 mM) was confirmed by quenched fluorescence of doxorubicin after digestion of liposomes with Triton X-100, spectrum change of doxorubicin, Dox color change from red to purple, and electron microscopy indicating the presence of dotted structures uniformly distributed within the liposomes.

At neutral pH, the quenched fluorescence of copper-doxorubicin crystals required EDTA and elevated temperature to fully restore the Dox fluorescence. Decreasing the pH of the environment allowed immediate dissolution of the copper-doxorubicin crystals, restoring the fluorescence and toxicity.

Increasing intra-liposomal copper concentration from 100 mM to 200 and 300 mM increased linearly doxorubicin intra-liposomal concentration to 400 and 600 mM, respectively, confirming formation of a 1:2 molar ratio complex within liposomes.

Liposomes and Drug Preparation

Doxil® (Ortho Biotech Products, LP Raritan, N.J.), a commercial ammonium sulfate-loaded doxorubicin liposome, was used for comparison to experimental preparations. Temperature-sensitive liposomes (TSLs) used in this study were of the following compositions:

1) Lyso-containing temperature-sensitive liposomes (LT-SLs) composed of DPPC:MPPC:DSPE-PEG2k with molar ratios of 86:10:4.

2) Temperature-sensitive liposomes (TSLs) composed of DPPC:DSPC:chol:DSPE-PEG2k were prepared in the absence or presence of 25% cholesterol with molar ratios of 85.5:9.5:0:5 (TSLs+0% chol) and 63:7:25:5 (TSLs+25% chol).

Copper-Doxorubicin Liposome Preparation

Liposomes were prepared as described above. 1,2-dipalmitoyl-sn-glycero-3-phosphocholine (DPPC), 1-palmitoyl-2-hydroxy-sn-glycero-3-phosphocholine (MPPC), 1,2 distearoyl-sn-glycero-3-phosphoethanolamine-N-Methoxy polyethyleneglycol-2000 (DSPE-PEG2k), 1,2-distearoyl-sn-glycero-3-phosphocholine (DSPC), and cholesterol (chol) were purchased from Avanti Polar Lipids Inc. (Alabaster, Ala.). The dried lipid was hydrated in 0.3 ml of 100 mM copper (II) gluconate (PURAC, Lincolnshire, Ill.) including 270 mM triethanolamine (TEA, Sigma, St. Louis, Mo.), pH 7.4 unless otherwise stated. The multi-lamellar lipid solution at a final concentration of 50 mg/mL was extruded above the phase transition temperature of the lipid mixture through a polycarbonate membrane with a pore diameter of 100 nm. Copper/TEA-loaded liposomes were then separated from non-encapsulated copper/TEA by passing the extruded liposomal solution through a spin column of Sephadex G-75 (5×1 cm, GE Healthcare, Biosciences, Piscataway, N.J.) equilibrated with 0.9% saline. The liposomal diameters were ~100 nm (103 nm±13 nm), as measured using a NICOMP™ 380 ZLS submicron particle analyzer (Particle Sizing System Inc., Santa Barbara, Calif.). Lipid concentration was measured using the Phospholipids C assay kit (Wako Chemicals USA, Richmond, Va.). Doxorubicin hydrochloride supplied by Sigma (St. Louis, Mo.) was then loaded and the resulting liposomes purified and characterized.

In Vivo Studies

All animal handling was performed in accordance with University of California, Davis (UCD), Animal Use and Care Committee guidelines. For in vivo NDL tumor studies, tumor fragments of approximately 1 mm$^3$ were transplanted into both inguinal fat pads of 3-5 week old FVB females (Charles River Breeding Laboratories). Tumors were grown for 2 weeks after transplantation to 4-6 mm in longitudinal diameter prior to treatment.

NDL tumor mice were injected with 120-150 µL of either free or liposomal doxorubicin via a 30-gauge catheter inserted to the mouse tail vein. To trigger the release of drug from temperature-sensitive liposomes ultrasound, one tumor was insonified for 20 min at 42° C. post-injection. At desired time points, a cohort of mice was euthanized by cervical dislocation. Blood was drawn from the heart using a heparin-treated syringe, collected into PST™ Gel tubes coated with lithium heparin (Becton Dickinson, Franklin Lakes, N.J.) and tumors were dissected. Plasma was isolated at 1200×g at 10 min at room temperature and diluted with an equal volume of water. Fluorescence intensity of doxorubicin was measured before and after incubation in the presence of 0.25% Tx-100 and 10 mM EDTA at 55° C. for 1 h using Tecan Infinite® M1000 Microplate Reader at excitation and emission wavelengths of 485 nm and 590 nm, respectively.

In Vivo Multi-spectral Fluorescence Imaging

The Maestro™ in vivo Imaging System (Cambridge Research & Instrumentation, Inc., Woburn, Mass.) was utilized. The system is consisted of a light-tight and temperature-controlled imaging chamber, a tunable multi-spectral camera system, and a computer with pre-installed software which allows accurate spectral unmixing for increased spectral contrast and improved data quantification. Each mouse was placed in the imaging chamber at 37° C., systemically injected with either free or liposomal doxorubicin, and imaged using the blue Maestro filter set (500:10: 720) with the exposure time of 1000 ms. The fluorescence signals were then unmixed from the auto-fluorescence in the image cube. A region of interest (ROI) was manually selected over the signal intensity. The area of the ROI was kept constant and the intensity was recorded as average signal (photons/s/cm$^2$) within a ROI. At desired time points post drug administration, mouse was placed under 3.5% isoflurane until asleep and then euthanized by ip injection of Euthasol (Western Medical Supply, Arcadia, Calif.) at 150-200 mg/kg body weight. After blood was drawn, the chest cavity was opened and the animal was perfused with 50 ml of saline. Organs and tissues were dissected and imaged for drug accumulation. Doxorubicin concentration in blood was measured as described previously.

Therapeutic Ultrasound

Temperature feedback was accomplished using a 30-gauge needle thermocouple (HYP-1, Omega Engineering, Inc., Stanford, Conn.), which was inserted between the tumor and the body wall, and interfaced to a data acquisition system controlled using LabVIEW™ (National Instruments Corp. Austin, Tex.) running on a PC. The therapeutic beam was swept in the azimuth dimension to fit the tumor dimensions. The animal's core temperature was monitored using a rectal thermocouple and was maintained at ~37° C. during the experiment.

Ultrasound-mediated Release of Doxorubicin from Temperature-sensitive Liposomal Doxorubicin in NDL Tumors of Tumor-bearing Mouse All animal handling was performed in accordance with University of California, Davis (UCD), Animal Use and Care Committee guidelines. Mice bearing bilateral NDL tumors of 4-6 mm in diameter (≥100 mm$^3$) were injected intravenously with either free or liposomal doxorubicin (~6 mg doxorubicin/kg body weight and ~32 mg lipid/kg body weight). Immediately after drug administration, one tumor per animal was insonified for 20 min at 42° C. The ultrasound pulses consisted of 100-cycle bursts at 1.5 MHz center frequency and 1.2 MPa peak negative pressure, with variable pulse-repetition frequency (PRF) ranging from 100 Hz up to 5 kHz.

In Vivo Imaging

Animal imaging was acquired before drug administration and right after tumor insonation using the Maestro™ hyperspectral imaging system (Cambridge Research & Instrumentation, Inc., Woburn, Mass.). Animals were then euthanized and perfused with saline and the accumulation of doxorubicin or copper in tissues and organs were imaged and quantified ex vivo.

Intracellular Trafficking and Subcellular Localization of Doxorubicin

We used the neu deletion (NDL) cell line which is a metastatic mammary carcinoma, originating from the overexpression of the ErbB-2/neu proto-oncogene (see Siegel P M; Ryan E D; Cardiff R D; Muller W J, The EMBO Journal (1999), 18(8), 2149-2164; and Miller J K; Shattuck D L; Ingalla, E Q; Yen L; Browosky A D; Young, L J T; Cardiff R D; Garraway III K L; Sweeney C, Cancer Research (2008), 68(20), 8286-8294). The Neu protein, a type I subclass of receptor tyrosine kinases, has been linked to initiation and progression of breast cancer. Cells were cultured in DMEM complete medium (Dulbecco modified Eagle medium, high glucose, supplemented with 10% fetal bovine serum, 1% penicillin-streptomycin, 0.584 g/L L-glutamine and 0.110 g/L sodium pyruvate) at 37° C. in an humidified 5% CO2 incubator. A monolayer of NDL cells plated in a 3.5 cm petri dish at 10$^6$ cells was incubated in the presence of 20 µg of either free doxorubicin or liposomal doxorubicin in temperature-sensitive liposomes in media containing 10% FSA on ice for 30 min. The cells were then rinsed with cold media and incubated at 37° C. At desired time points, the plate was transferred to a microscope (Mikron IV 600L, San Diego, Calif.) for optical observation. Images were recorded with a Cascade 512b (Photometrics, Tucson, Ariz.) digital camera in both bright field and fluorescence (mercury arc light source). Samples were analyzed optically with 63× water-immersed objective magnification. Doxorubicin trafficking was tracked using its fluorescence at Ex: 485 nm and Em: 590 nm. Subcellular localization of doxorubicin was determined using DAPI (Ex: 358 nm, EM: 461 nm) at final concentration of 600 nM to stain nucleus and LysoTracker-blue (Ex: 373 nm, Em: 422 nm) at final concentration of 5 µM to stain lysosomes. Cells were fixed with 3% paraformaldehyde prior to microscopy.

Results

We exploited the stability of the copper-doxorubicin crystals described above to further enhance efficacy and reduce toxicity, and demonstrate the potential for pH-sensitive and temperature-sensitive carriers, in which ultrasound-mediated hyperthermia is used to release the drug.

Figure 9:
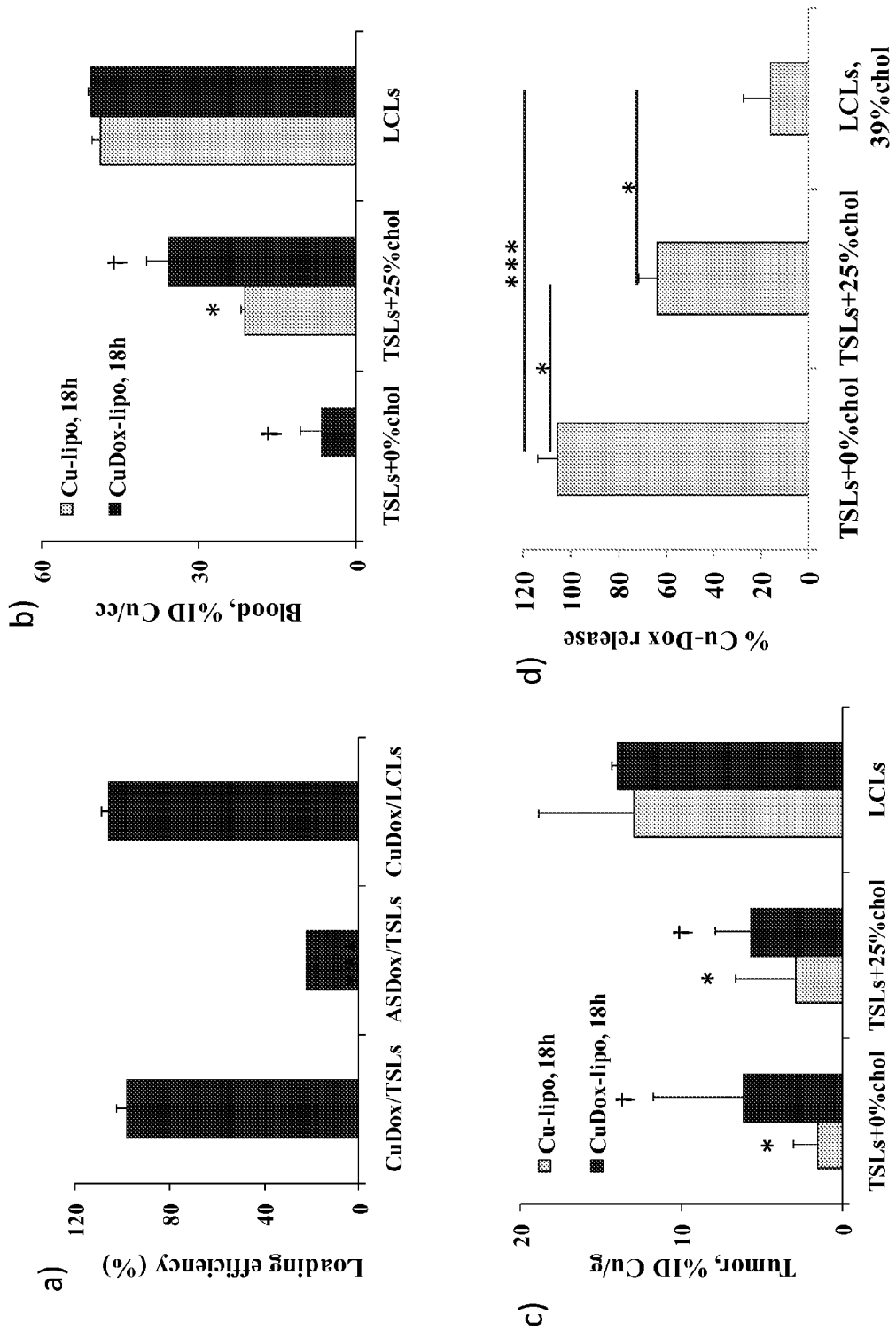
FIG. 9. Copper-doxorubicin in temperature-sensitive liposomes. a, Loading efficiency of doxorubicin in TSLs containing 100 mM copper/270 mM TEA compared to those achieved when doxorubicin was encapsulated in TSLs using the ammonium sulfate gradient method or in LCLs containing 100 mM copper/270 mM TEA at initial Dox/lipid ratio of 0.2 mg/mg. b, c, Blood stability (b) and tumor accumulation (c) of copper-doxorubicin in temperature-sensitive liposomes (TSLs), with and without the addition of 25% cholesterol (molar percent) and compared to long-circulating liposomes (LCLs), as quantified by copper (ICP-MS) and indicated by % injected dose. d, Release of doxorubicin from liposomal copper-doxorubicin in temperature-sensitive formulations as a function of cholesterol in mouse serum at 45° C. and 1 h. *p<0.05, ***p<0.001. This figure shows that Cu-Dox can be efficiently loaded, accumulates within tumors, circulates stably in blood and yet can be released by heat.

We evaluated doxorubicin loading in lyso temperature-sensitive liposomes containing 100 mM copper/270 mM TEA (CuDox-LTSLs) or when Dox was loaded using the ammonium sulfate method (ASDox-LTSLs), and compared that with long-circulating liposomes containing 100 mM copper/270 mM TEA (CuDox-LCLs). Similar to CuDox-LCLs, a loading efficiency of 100% was also achieved in CuDox-LTSLs, where loading was only 22% with ASDox-LTSLs (FIG. 9a). To determine the effect of the copper-doxorubicin complex on the plasma stability, pharmacokinetic profiles were assessed for temperature-sensitive liposomes (which generally contain a lower concentration of cholesterol than long circulating liposomes). Eighteen hours after intravenous injection of liposomal copper or liposomal copper-doxorubicin, the circulation half-life (FIG. 9b) and tumor accumulation of copper (FIG. 9c) were enhanced for low cholesterol copper-doxorubicin liposomes, as compared with copper liposomes. Increasing the fraction of cholesterol by 25 mol % further enhanced the circulation half-life and tumor accumulation of temperature-sensitive liposomes (FIGS. 9b, c). With cholesterol-rich, long-circulating liposomes containing copper, copper accumulation in tumors was unchanged by the presence of doxorubicin.

Figure 10:
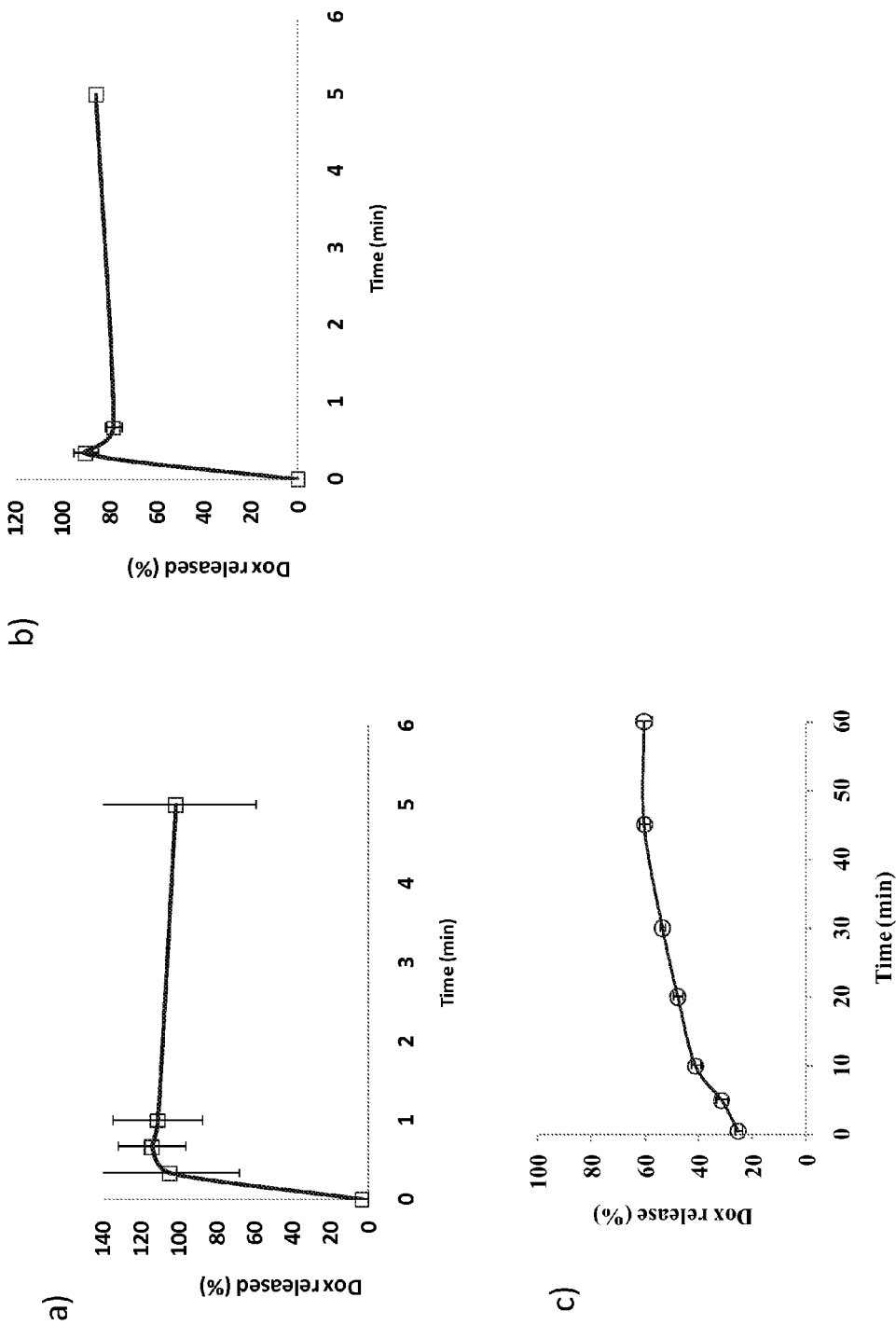
FIG. 10. In vitro release of doxorubicin from liposomal doxorubicin in temperature-sensitive liposomes at 45° C. in mouse serum. (a) Dox release from liposomal copper-Dox in lyso-containing temperature-sensitive liposomes (CuDox-LTSLs), (b) from liposomal Dox in lyso-containing temperature-sensitive liposomes when doxorubicin was encapsulated using the ammonium sulfate gradient method (ASDox-LTSLs) (c), and from liposomal copper-Dox in cholesterol-containing temperature-sensitive liposomes (CuDox-TSLs+25% chol). Release of doxorubicin was performed in the presence of 30 mM EDTA in serum.

Cholesterol is added to liposomal formulations to enhance plasma stability, yet, activatable formulations can require a reduction in the cholesterol content and thus stability is reduced. Here, as the concentration of cholesterol within the shell was decreased, differences in the blood pharmacokinetics between copper in copper-doxorubicin liposomes and in copper liposomes were enhanced. For temperature-sensitive liposomes, the improved blood half-life of copper-doxorubicin liposomes improved the accumulation of copper within the tumor. While cholesterol can be needed to improve the plasma stability, it reduces the heat responsivity of liposomes. FIG. 9d shows that temperature-sensitive liposomes with 25% cholesterol are still activatable and release 60% of the encapsulated doxorubicin compared to non-cholesterol TSLs at 45° C. after 1 h. Release profile of doxorubicin from Lyso-temperature-sensitive liposomes containing either copper-doxorubicin or ammonium sulfate-doxorubicin demonstrated a rapid release time with nearly the entire Dox content released in tens of seconds (FIG. 10a-b). In contrast, temperature-sensitive liposomes with 25% cholesterol show a slow release pattern with 50% release in 30 min in mouse serum (FIG. 10c).

Figure 11:
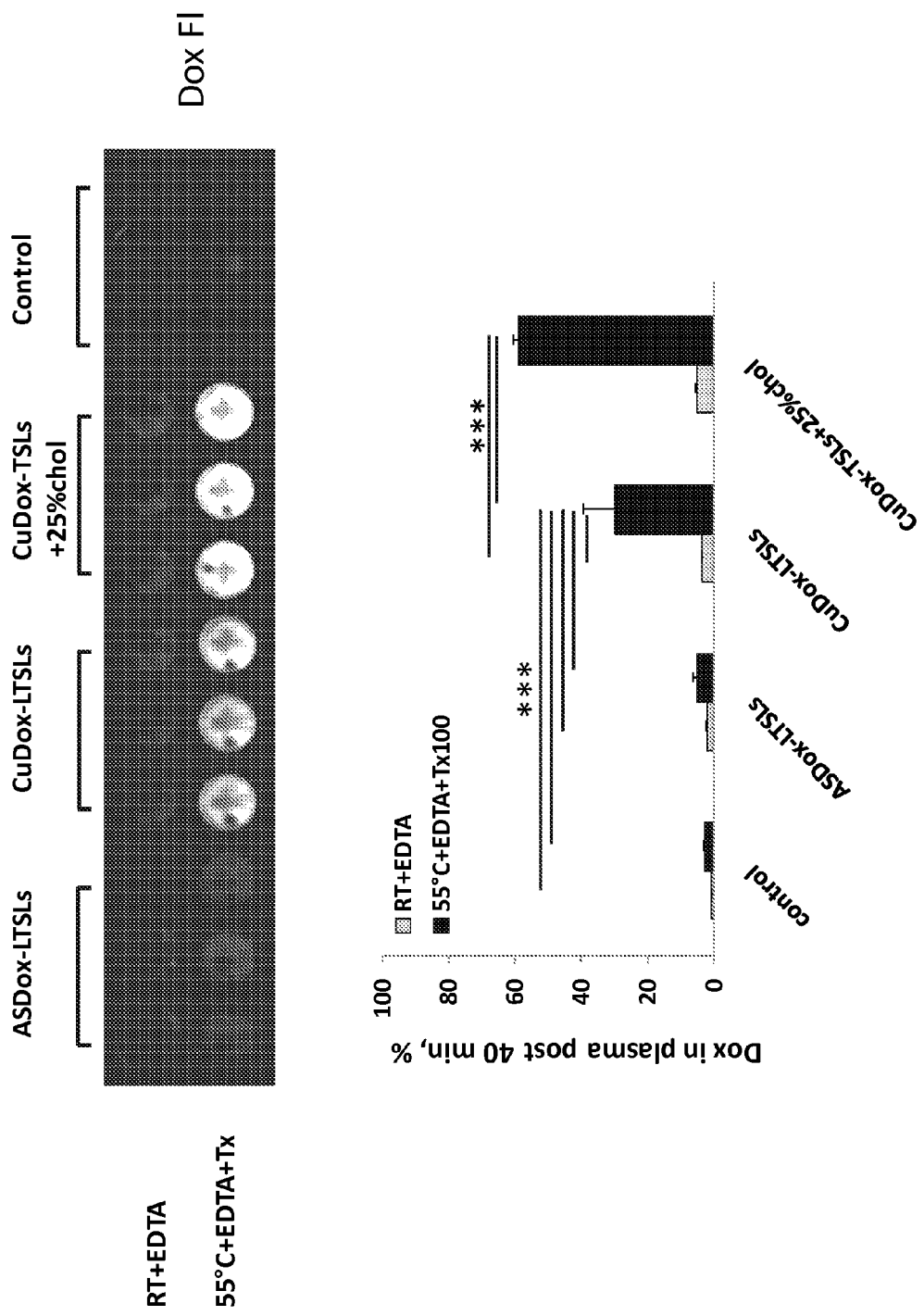
FIG. 11. Plasma stability of liposomal doxorubicin in temperature-sensitive liposomes. Doxorubicin in plasma after 40 min post administration of liposomal doxorubicin when Dox was loaded in lyso-temperature sensitive liposomes using the ammonium sulfate method (ASDox-LTS1s) or in temperature sensitive liposomes with and without 25% cholesterol containing 100 mM copper/270 mM TEA (CuDox-TSLs+25% chol) and (CuDox-TSLs+0% chol) compared to control plasma. Plasma isolated from mouse blood was incubated at room temperature in the presence of 30 mM EDTA to measure free doxorubicin in plasma, and digested with Triton X-100 in the presence of 30 mM EDTA at 55° C. to measure doxorubicin in circulating liposomes. Statistical analyses were performed using one-way ANOVA followed by a Tukey Post Hoc test. ***p<0.001. Inset image acquired by Maestro imaging system (increasing white intensity indicates higher doxorubicin fluorescence intensity).

Quantification of doxorubicin in isolated plasma revealed a short half life of doxorubicin loaded in lyso-temperature-sensitive liposomes using ammonium sulfate method with a rapid Dox release and clearance within 40 min post administration of liposomal doxorubicin, the period required to administer the drug and insonify one tumor to trigger the release and delivery of Dox into tumor (FIG. 11). Formation of copper-Dox complex within the same liposomal formulation extended the drug circulation to 30% without cholesterol and to near 60% with addition of 25% cholesterol to the lipid shell (FIG. 11).

Figure 12:
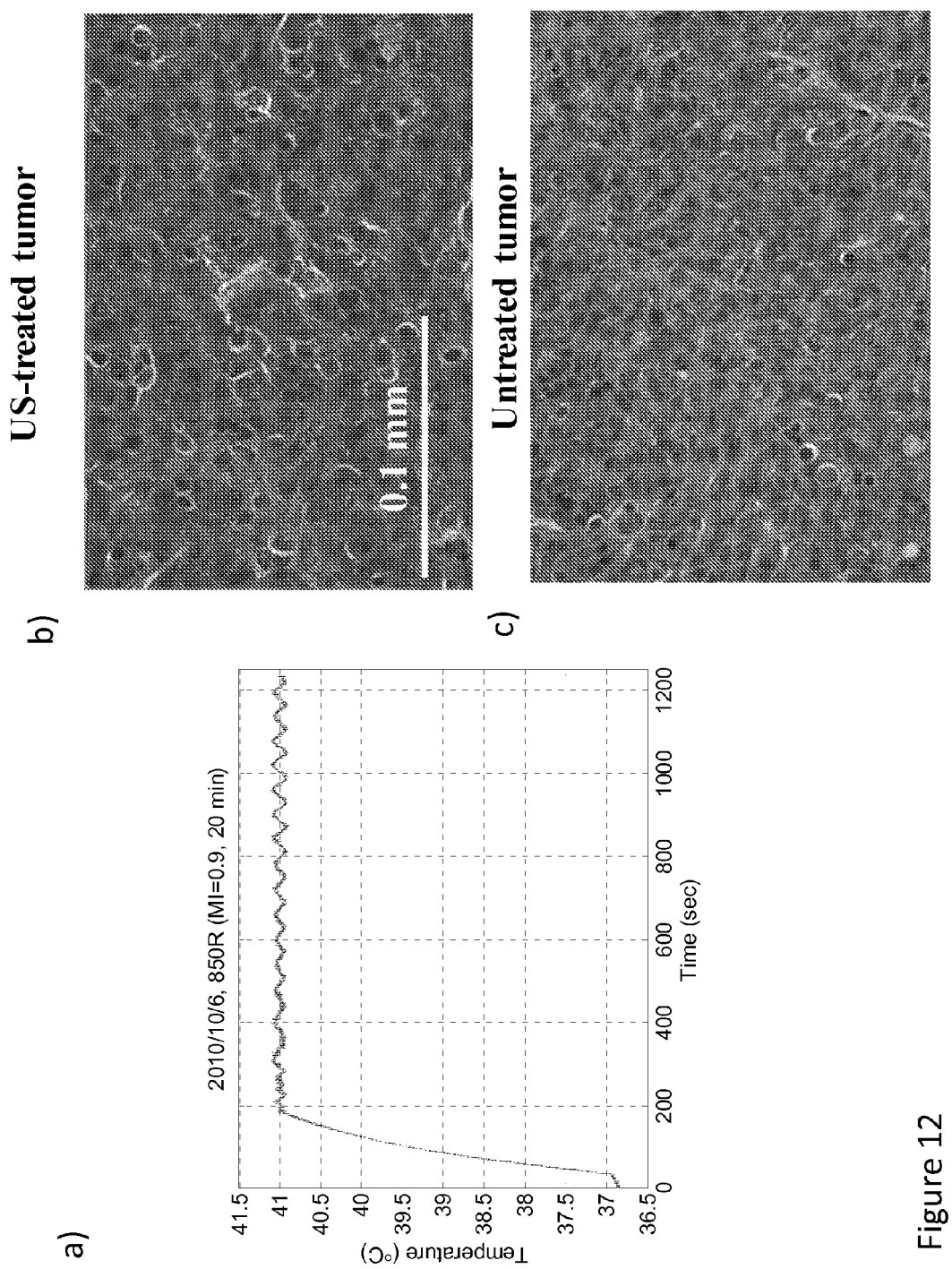
FIG. 12. Heating profile of tumor insonation and its effect on tumor morphology. a) Tumor heating profile during 20 min of insonation. H&E histological section of insonified tumor (b) and untreated tumor (c). The heating profile is that recorded during treatment. This figure shows that ultrasound alone does not have a therapeutic effect.

To optimize ultrasound parameters to trigger release of drug from liposomal carrier without affecting the integrity and cellular morphology of insonifying tumor, a 20-min ultrasound radiation at MI=0.9 was applied in our study. FIG. 12a presents the heating profile with a 2-3 min initial heating phase to elevate tumor temperature to 41° C. and maintaining this elevated temperature for the rest of the 20-min heating period. H&E histological sections of insonified tumor showed no substantial signs of ablation or changes in integrity of tumor—thus ultrasound alone or with drug did not immediately ablate tissue (FIG. 12b-c).

Figure 13:
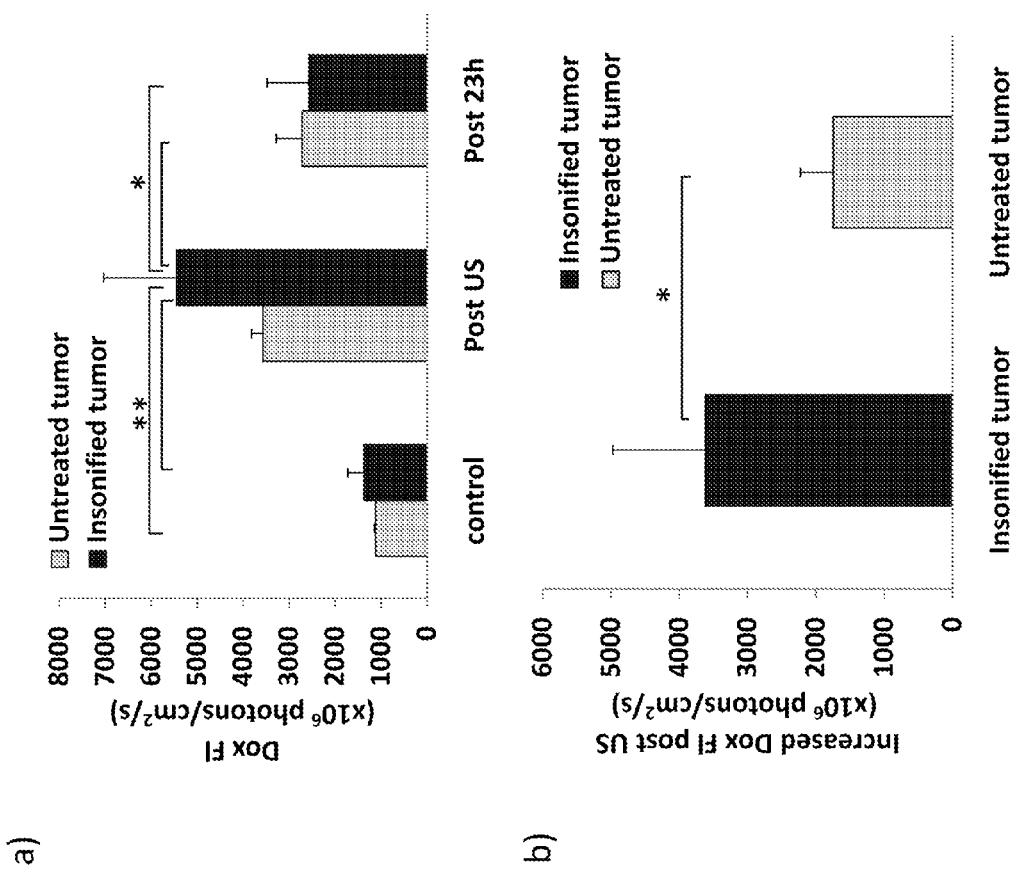
FIG. 13. Intravascular release of doxorubicin from liposomal copper-doxorubicin in temperature-sensitive liposomes. a) Dox fluorescence quantified from Maestro images acquired after tumor insonation of mice received 6 mg/kg-body weight of liposomal copper-doxorubicin in temperature-sensitive liposomes with 25% cholesterol (CuDox-TSLs+25% chol) and after 23 hours post drug administration compared to those received saline (control). b) Magnitude of Dox released in insonified tumor compared to untreated tumor after 40-min skin signal was reduced from tumor signals. Statistical analyses were performed using one-way ANOVA followed by a Tukey Post Hoc test (a) and Student's t-test (b). *p<0.05, **p<0.01. This figure shows that Cu-Dox is freed from the liposomes when insonified within the tumor. The fluorescence increase after ultrasound demonstrates that the metal and drug are disassociated.

We then applied ultrasound to one tumor of a tumor-bearing mouse with bilateral tumors immediately after administration of 6 mg/kg-animal body weight of CuDox-TSLs+25% chol and monitored the fluorescence of doxorubicin in insonified tumor versus untreated tumor. FIG. 13a shows an increased fluorescence of doxorubicin in insonified tumor compared to that after 24 h post administration of drug and to control mice that received saline. Reducing the skin signal from total Dox fluorescence in tumors shows a significantly increased release and delivery of doxorubicin in insonified tumor versus untreated controls (FIG. 13b).

Figure 14:
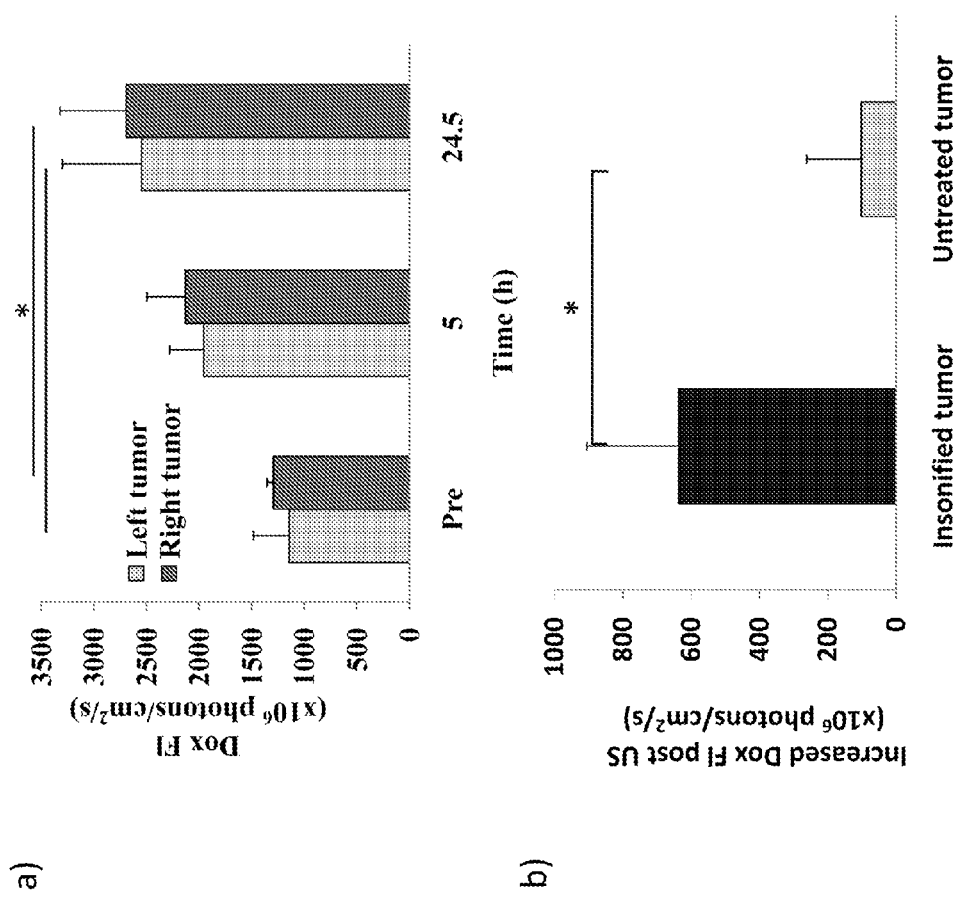
FIG. 14. Interstitial release of doxorubicin from liposomal copper-doxorubicin in temperature-sensitive liposomes. a) Accumulation of liposomal copper-doxorubicin in Temperature-sensitive liposomes (CuDox-TSLs+0% chol) in NDL-tumors over time. b) Dox release from CuDox-TSLs+0% chol in insonified tumors compared to untreated tumors. Statistical analyses were performed using one-way ANOVA followed by a Tukey Post Hoc test (a) and Student's t-test (b). *p<0.05. This figure shows that in a) that Cu-Dox liposomes circulate stably and b) that the Cu-Dox is freed from the liposomes when insonified within the tumor. The fluorescence increase after ultrasound demonstrates that the metal and drug are disassociated.

We next compared this strategy with the strategy when drug is administrated to an animal and allowed accumulation of liposomal doxorubicin in tumors due to the Enhanced Permeability and Retention effect (EPR). Ultrasound was applied after 18 h post drug administration when accumulation of liposomes peaks. FIG. 14a demonstrates an increase in doxorubicin fluorescence in tumors over time as the result of EPR effect. Insonifying one tumor at 18 h post drug administration resulted in further increase in tumoral doxorubicin fluorescence (FIG. 14b).

Figure 15:
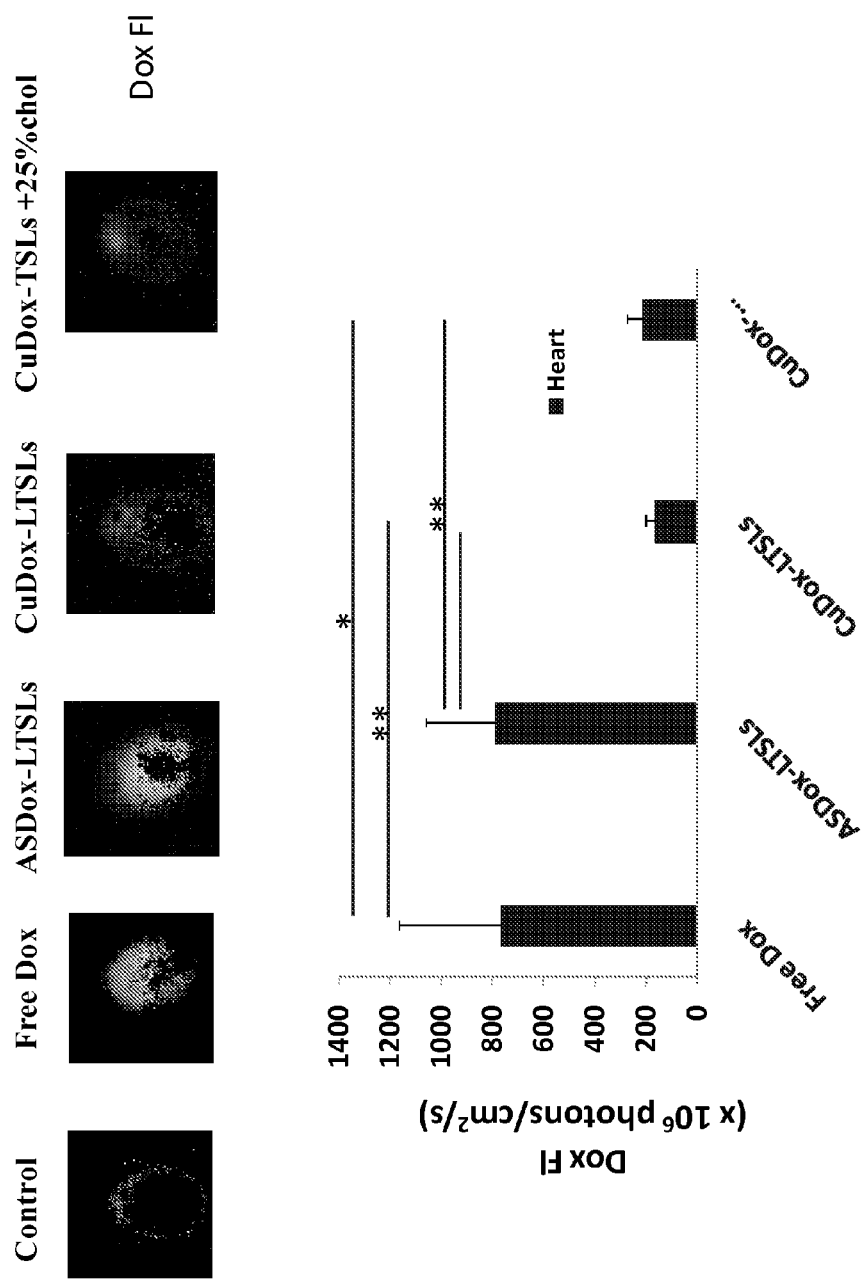
FIG. 15. Ex vivo imaging of doxorubicin accumulation in mouse heart after liposomes were injected into the tail vein and allowed to circulate. Heart was removed after euthanasia to assess fluorescence. a) Doxorubicin fluorescence in hearts of mice injected with liposomal doxorubicin in lyso-temperature sensitive liposomes when Dox was loaded with ammonium sulfate method (ASDox-LTSLs) or loaded in liposomes containing 100 mM copper/270 mM TEA (CuDox-LTSLs), and loaded in temperature sensitive liposomes with 25% cholesterol containing 100 mM copper/270 mM TEA (CuDox-TSLs+25% chol) compared to those injected with free Dox. Animals were euthanized 40 min post administration of free or liposomal doxorubicin. Animals were perfused with saline and hearts were dissected prior to Maestro imaging. Statistical analyses were performed using one-way ANOVA followed by a Tukey Post Hoc test. *p<0.05, **p<0.01. Inset images of heart acquired by Maestro imaging system (white indicates higher doxorubicin fluorescence intensity). This figure shows that doxorubicin accumulates in the heart after the injection of free doxorubicin or AS-Dox liposomes; however, heart accumulation of doxorubicin was greatly reduced after the injection of Cu-dox liposomes.
Figure 16:
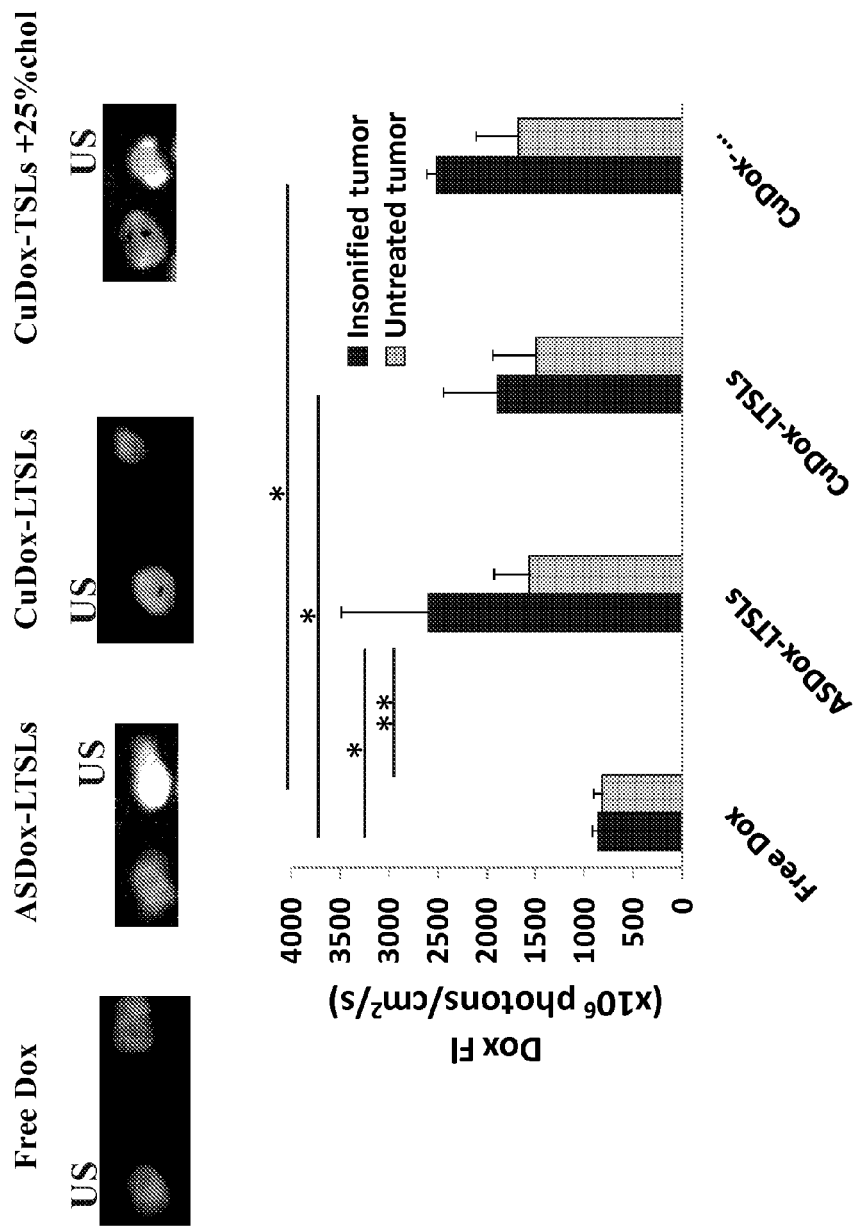
FIG. 16. Ex vivo imaging of doxorubicin accumulation in NDL tumors. a) Doxorubicin fluorescence in NDL tumors of mice injected with liposomal doxorubicin in lyso-temperature sensitive liposomes when Dox was loaded with ammonium sulfate method (ASDox-LTSLs) or loaded in liposomes containing 100 mM copper/270 mM TEA (CuDox- LTSLs), and loaded in temperature sensitive liposomes with 25% cholesterol containing 100 mM copper/270 mM TEA (CuDox-TSLs+25% chol) compared to those injected with free Dox. Animals were euthanized 40 min post administration of free or liposomal doxorubicin. Animals were perfused with saline and tumors were dissected prior to Maestro imaging. Statistical analyses were performed using one-way ANOVA followed by a Tukey Post Hoc test. *p<0.05, **p<0.01. Inset images of tumors acquired by Maestro imaging system (white indicates higher doxorubicin fluorescence intensity). "US" indicates the insonified tumor. This figure shows that doxorubicin accumulates within the tumor after insonation for both ASDox and CuDox liposomes.

Ex vivo imaging of heart revealed a 4-fold increase in cardiac accumulation of doxorubicin 40 min post administration of either free doxorubicin or liposomal doxorubicin loaded by the ammonium sulfate method in lyso-temperature-sensitive liposome (ASDox-LTS1s), compared to those of liposomal copper-doxorubicin in temperature-sensitive liposomes with or without cholesterol (FIG. 15). These results show that doxorubicin, when crystallized with copper in temperature-sensitive liposomes, accumulates less in the heart and therefore, is less cardio-toxic. The magnitude of doxorubicin accumulation for Free Dox was similar to that of ASDox-LTSLs, which indicates rapid release and clearance of doxorubicin from the ammonium sulfate loaded formulation. Doxorubicin was accumulated similarly in insonified tumors for all liposomal doxorubicin compared to those of Free Dox (FIG. 16).

Figure 17:
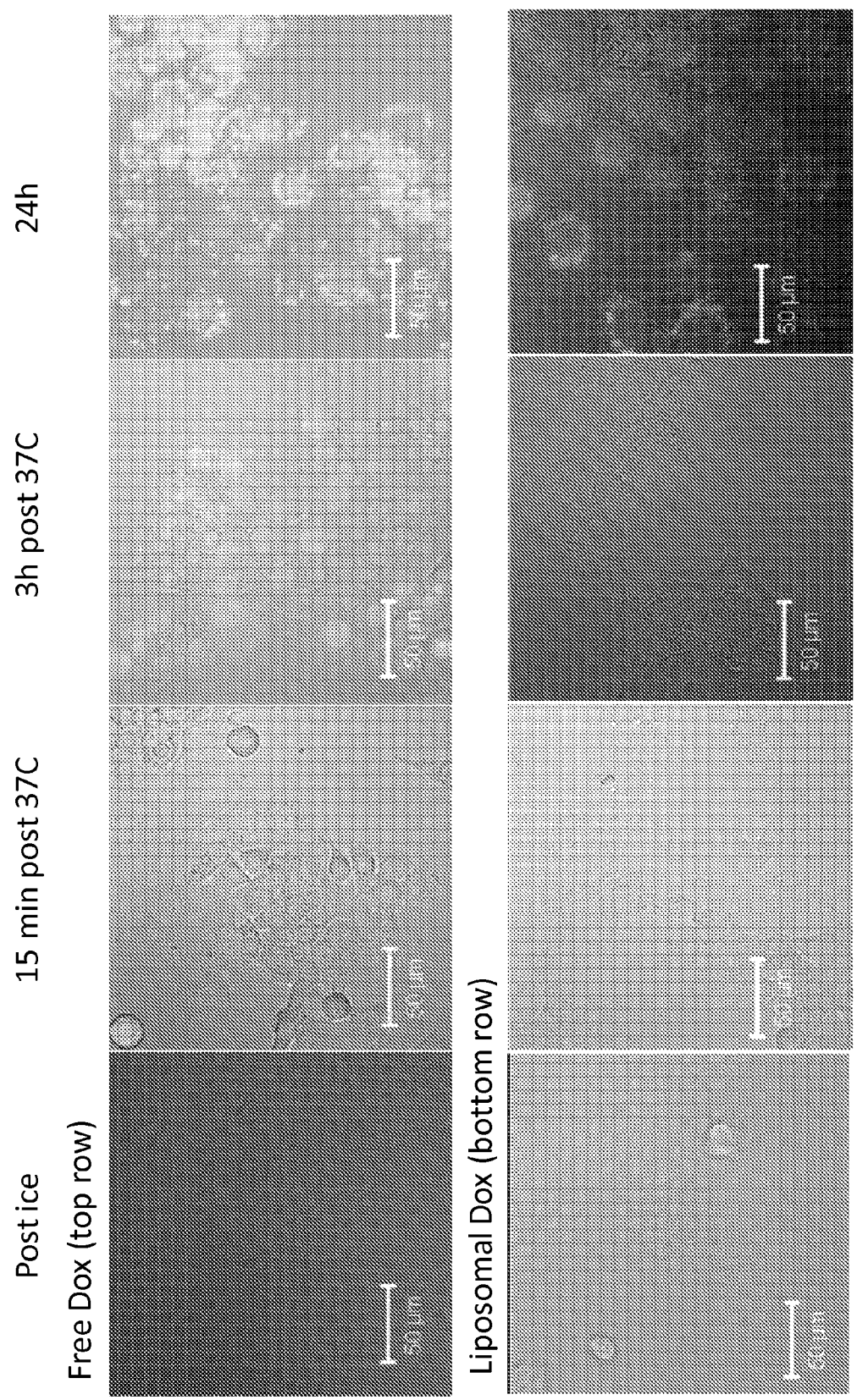
FIG. 17. Intracellular trafficking of free doxorubicin versus liposomal doxorubicin in NDL cells. NDL cells ($\sim 10^6$ cells/plate) were incubated with 20 μg of free doxorubicin or liposomal doxorubicin in temperature-sensitive liposomes (ASDox-LTSLs, CuDox-LTSLs, CuDox-TSLs+0% chol, CuDox-TSLs+25% chol) on ice for 30 min. Cells were then rinsed with cold media and incubated at 37° C. Merged images of doxorubicin and bright field are presented at 15 min, 3 h, and 24 h post incubation at 37° C. All liposomal formulations yielded similar results and therefore only one result (arbitrarily chosen) is presented.

To further study delivery of doxorubicin in NDL tumors, we next evaluated trafficking of doxorubicin across different liposomal doxorubicin in temperature-sensitive liposomes and compared with that of Free Dox. The nucleus showed doxorubicin fluorescence as early as 15 min post incubation at 37° C., however, all liposomal doxorubicin reached the nucleus with a delay of 3-5 h (FIG. 17). These results suggest that liposomal doxorubicin internalized via an endocytosis pathway, whereas free doxorubicin flip flops across the plasma and intracellular membranes. The nucleus was the final destination for doxorubicin in either Free Dox or across all liposomal doxorubicin studied. Nuclear and lyso-somal staining further assisted us to visualize localization of doxorubicin in liposomal doxorubicin over time (FIG. 18a-c). Images acquired at 5 h show localization of Dox in lysosomes accumulating around the nucleus, nucleus envelop and in the nucleus (FIG. 18b). At 24 h, the doxorubicin signal was brighter in both the nucleus and lysosomes, with lysosomes getting separated from nucleus, perhaps washing the excess doxorubicin out of the nucleus (FIG. 18c). In summary, we found that the uptake of copper-doxorubicin filled liposomes resulted in similar doxorubicin trafficking to the nucleus as compared with free doxorubicin.

Figure 19:
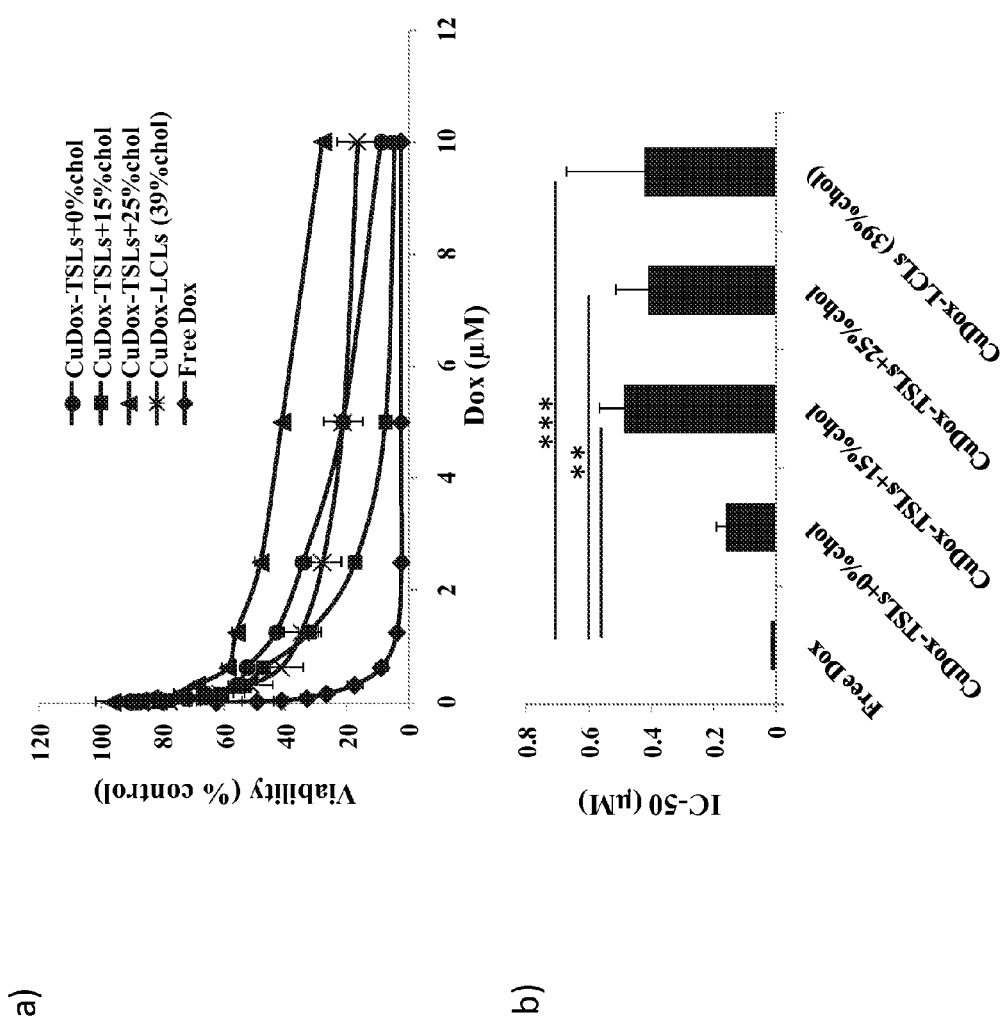
FIG. 19. In vitro cell viability of liposomal copper-doxorubicin as a function of increased molar ratios of cholesterol in temperature-sensitive liposomal formulation compared to those obtained with free doxorubicin and liposomal copper-doxorubicin in long-circulating liposomes. a) Viability of $1^{fvb2}$ mammary carcinoma cells as a function of serial dilutions of doxorubicin. b) IC50 values of free and liposomal copper-doxorubicin. Statistical analyses were performed using one-way ANOVA followed by a Tukey Post Hoc test. p<0.01, *p<0.001. This figure shows that addition of cholesterol to the liposomal formulation of copper-doxorubicin significantly increases the IC50 value of liposomal copper-doxorubicin. IC50 value of liposomal copper-doxorubicin in TSLs without cholesterol was reduced to the value comparable to that of free doxorubicin.

In addition we studied the in vitro cell viability of liposomal copper-doxorubicin as a function of increased molar ratios of cholesterol in temperature-sensitive liposomal formulation compared to those obtained with free doxorubicin and liposomal copper-doxorubicin in long-circulating liposomes. FIG. 19a shows the viability of $1^{fvb2}$ mammary carcinoma cells as a function of serial dilutions of doxorubicin. FIG. 19b shows IC50 values of free and liposomal copper-doxorubicin.

Formation of copper-doxorubicin crystals within temperature-sensitive liposomes increased doxorubicin loading, improved plasma stability of doxorubicin, and augmented the accumulation of liposomes in tumors.

Example 7

Doxorubicin Delivery in a Crystal Form with Copper in Various Drug-delivery Carriers Copper-doxorubicin crystals not only can be assembled within liposomes, but also can be incorporated into other attractive drug-delivery carriers such as micelles, dendrimers, and biodegradable polymeric carriers or vesicles (polymersomes). Doxorubicin crystal formation with copper provides at least two major advantages that make it unique and attractive: the first is its pH-sensitive property that releases Dox at low-pH environments such as lysosomes and tumors/diseased tissues; the second is that it quenches doxorubicin fluorescence but restores the fluorescence upon liberation of doxorubicin as free Dox. The former contributes to applications of efficacious drug delivery systems with reduced toxicity. The latter facilitates carrier design and optimization, as well as monitoring blood circulation or tissue accumulation of doxorubicin in its crystal form with copper or as freed doxorubicin by in vivo/in vitro optical systems.

Micelles can be used and generally have substantial loading capacities and reduced ability to interact with RES cells. Self-assembled micelle aggregates of block copolymers and cyclic dendrimeric structures sized 20-100 nm in diameter can be used. Pegylated lipids or poly(ethylene glycol)-poly(amino acid) block copolymer micelles which can be functionalized for applications such as imaging, diagnosis, and tumor treatment, are well used in drug-delivery studies (Chen W; Meng F; Cheng R; Zhong Z, Journal of Controlled Release, (2010), 142, 40-46. For dendrimers, pegylated polyacrylic acid, PAA, or poly amino acids can be used to allow branched structures (Chen B; Jerger K; Frechet J M J; Szoka F C, Journal of Controlled Release, (2009), 140, 203-209).

For micelles, a composition of lipids conjugating doxorubicin with or without PEG2k lipids will result in natural assembly of micelles above the critical micellar concentration of the lipids. Then, Dox-lipid micelles are incubated with copper to produce copper-Dox micelles. Alternatively, doxorubicin is conjugated to lipids via a temperature-sensitive linkage that produces a temperature-sensitive micellar copper-doxorubicin. The crystal formation is monitored and optimized using the quenching property of copper-doxorubicin. Doxorubicin-copper crystal are released in a subject upon an elevation in temperature and doxorubicin is freed at low-pH environments providing therapeutic effects in tumor/diseased tissues combined with low toxicity to normal tissues/organs. A similar method is applied for producing copper-doxorubicin conjugated to dendrimers with various structures.

Doxorubicin-copper can also be incorporated in or attached to the surface of polymer carriers. Polymer nanoparticles can be prepared by several methods such as the solvent evaporation method and the emulsification methods generally known in the art. Liposomes, self-assembled vesicles, can be used as templates to produce size-controlled and monodispersed polymer nanoparticles of defined size without use of any types of solvent or surfactant. Poly (ethylene glycol) hydrogel, a biocompatible and nontoxic, and particularly PEG hydrogel functionalized with diacrylate group can participate in photopolymerization process. Therefore, PEG hydrogel solution inside a liposome can be polymerized by exposure to UV radiation (An S Y; B M P N; Nam Y J; Han K N; Li C A; Choo J; Lee E K; Katoh S; Kumada Y; Seong G H, Journal of Colloid and Interface Science (2009), 331, 98-103).

One example would be preparing liposomes in the presence of a photo-crosslinkable prepolymer and copper/TEA. Then doxorubicin is loaded into liposomes and forms a crystal with copper within liposomes as described previously in the methods above. The photo-crosslinkable prepolymer encapsulated inside liposomes then forms a polymer upon radiation with UV under the liposomal shell. The liposomal membrane is digested and removed, and the polymeric particles encapsulating copper-doxorubicin are produced. Depending on the polymers, temperature-sensitive or rigid and long-circulating polymeric carriers with a defined size are created. Doxorubicin can be attached to the surface of the polymer carriers via a temperature-sensitive linker and then incubated with copper to form doxorubicin-copper crystals on the surface of carriers.

Polymersomes (polymer vesicles) are attractive vesicles since they mimic liposome assembly with several fold higher shell rigidity. Copper-containing polymersomes are produced by drop wise addition of copper/TEA solution at neutral pH to copolymer solution dissolved in organic solvent (e.g., dioxane). Doxorubicin is added and the resulting solution is sonicated at elevated temperatures to allow the drug loading. The organic solvent and free doxorubicin are removed by dialysis.

Doxorubicin in micelles, dendrimers, or polymersomes are used in vivo similar to liposomes using the methods described above and produce similar results as described in the Examples above for liposomes.

Example 8

Production and Use of Agent and Agent-Transition Metal Complexes in Carriers in Mice A membrane permeable buffer triethanolamine (TEA, pKa: 9.5, membrane permeability coefficient: 0.12 cm/s), is used to load an agent within a carrier. Agents include anthracyclines such as daunorubicin, doxorubicin, epirubicin, idarubicin, mitoxantrone, valrubicin, and irinotecan. Carriers include liposomes, micelles, polymersomes, and nanoparticles. A triethanolamine (TEA) gradient created across the carrier membrane loads an agent efficiently in the absence of a pH gradient or a transition metal ion at neutral pH. The TEA gradient can be 90-270 mM and the pH can be 7.4. Concentration via triethanolamine is then optimized to encapsulate an optimal amount of agent (e.g., 200 mM) inside the intra-carrier medium. To do this, a carrier with a desired diameter is formed using methods known in the art and/or as described above. A TEA gradient is then created across the carrier membrane by separating free TEA from carrier encapsulated TEA using a column such as a Sephadex G-75 column. TEA encapsulating carriers are collected in a solution (e.g., saline) and incubated with an agent in a solution at a pre-determined concentration, mass ratio, temperature, and amount of time (e.g., 2 mg/ml of agent in saline at initial mass ratio of 0.2 mg/mg at 37° C. for 1.5 h, 3 h, 6 h, 12 h, 18 h, or 24 h).

To form a transition metal-agent complex (e.g., at a molar ratio of 1:2) at neutral pH, carriers are prepared in the presence of a transition metal (e.g., 100 mM) and TEA (e.g., 270 mM) with pH adjusted to neutral (e.g., 7.4). Transition metals include manganese, iron, and copper. Carriers include liposomes, micelles, polymersomes, and nanoparticles. Transition metal/TEA carriers are then separated from free transition metal and a TEA gradient (e.g., 90-270 mM) is generated across the carrier membrane; carriers are then incubated in the presence of an agent in solution (e.g., at 2 mg/ml of agent in saline) as described above. Agents include anthracyclines such as daunorubicin, doxorubicin, epirubicin, idarubicin, mitoxantrone, valrubicin, and irinotecan. In some aspects, transition metal/TEA carriers are obtained from a third party and then a TEA gradient (e.g., 90-270 mM) is generated across the carrier membrane; carriers are then incubated in the presence of an agent in solution (e.g., at 2 mg/ml of agent in saline) as described above. Crystal formation between transition metal and agent (e.g., 100 mM: 200 mM) is confirmed, e.g., by quenched fluorescence of agent after digestion of carriers (e.g., with Triton X-100), spectrum change of agent, color change, and/or electron microscopy indicating the presence of dotted structures uniformly distributed within the carriers.

In Vivo Studies

For in vivo Met-1 tumor studies, tumor fragments of approximately 1 mm$^3$ are transplanted into both inguinal fat pads of 3-5 week old FVB females (Charles River Breeding Laboratories). Tumors are grown for 2 weeks after transplantation to 4-6 mm in longitudinal diameter prior to treatment.

The mice bearing bilateral Met-1 tumors are randomized into several groups of 3-4 mice/group and treated with either single or combination therapy. The animals are anesthetized by 3.5% isoflurane and maintained at 2.0-2.5% during the injection and imaging. Each mouse is injected intravenously with either free agent or agent within a carrier (with and without transition metal) twice a week and then compared to control animals that receive saline. For rapamycin, animals are treated by intraperitoneal (ip) injection of (~0.9 mg rapamycin/kg body weight) three times a week over the entire period of treatment. For combined treatments with ultrasound, one tumor per animal is insonified for 2 min at 42° C. post-injection.

The tumor progression/regression is monitored using a 2D Acuson Sequoia® 512 ultrasound imaging system (Siemens Medical Solution USA, Inc., Issaquah, Wash.) equipped with a 15L8-S, 14 kHz high frequency linear array transducer. After the region surrounding the tumor is shaved, the tumor is viewed in both the transverse and sagittal planes and the tumor boundary is fitted with an ellipse in each view measuring $D_1$ or $D_3$ and the depth $D_2$. Tumor volume is then calculated using the following equation:

$$V = \frac{\pi}{6}(D_1 \times D_2 \times D_3)$$

where $D_2$ is the average of depth measured in each transverse and sagittal view. (2)

Pharmacokinetics and Biodistribution of Copper-doxorubicin Liposomes

Met-1 tumor mice are injected with either agent-transition metal carriers or transition metal carriers via a 30-gauge catheter inserted to the mouse tail vein. For animals randomized to receive ultrasound, one tumor is insonified for 2 min at 42° C. post-injection. At the 5 min, 6 h, 18 h, and 24 h time points, a cohort of mice are euthanized by cervical dislocation. Blood is drawn from the heart using a heparin-treated syringe, collected into PST™ Gel tubes coated with lithium heparin (Becton Dickinson, Franklin Lakes, N.J.) and tumors are dissected. Plasma is isolated at 1200×g at 10 min at room temperature and diluted with an equal volume of water. Fluorescence intensity of doxorubicin is measured before and after incubation in the presence of 0.25% Tx-100 and 10 mM EDTA at 55° C. for 1 h using Tecan Infinite® M1000 Microplate Reader at excitation and emission wavelengths of 485 nm and 590 nm, respectively. Tumor samples are collected in 5 mL cryovials (Phenix Research, Candler N.C.) and stored at −80° C. For tumor digestion, samples are frozen in liquid nitrogen and lyophilized overnight. One milliliter of concentrated nitric acid (trace-metal-grade, 70%; Fisher Scientific, St. Louis, Mo.) is then added to the dried tumor samples and the mixture incubated for 4 hours at 60° C. and then overnight at room temperature. One milliliter of 30% hydrogen peroxide (Optima trace-metal-grade; Fisher Scientific, St. Louis, Mo.) is then added and the mixture incubated for 2 hours at 55° C. The volume is completed to three milliliters with purified DI water. Isolated plasma and digested tumor samples are analyzed for transition metal content using Inductively Coupled Plasma (quadrupole) Mass Spectrometry (ICP-MS, Agilent Technologies, Santa Clara, Calif.).

In Vivo Multi-spectral Fluorescence Imaging

The Maestro™ in vivo Imaging System (Cambridge Research & Instrumentation, Inc., Woburn, Mass.) is utilized. The system consists of a light-tight and temperature-controlled imaging chamber, a tunable multi-spectral camera system, and a computer with pre-installed software which allows accurate spectral unmixing for increased spectral contrast and improved data quantification. Each mouse is placed in the imaging chamber at 37° C., systemically injected with either free agent or agent with carrier, and imaged using the blue Maestro filter set (500:10:720) with the exposure time of 1000 ms. The fluorescence signals are then unmixed from the auto-fluorescence in the image cube. A region of interest (ROI) is manually selected over the signal intensity. The area of the ROI is kept constant and the intensity is recorded as average signal (photons/s/cm$^2$) within a ROI. At 24 h or 48 h post drug administration, mouse is placed under 3.5% isoflurane until asleep and then euthanized by ip injection of Euthasol (Western Medical Supply, Arcadia, Calif.) at 150-200 mg/kg body weight. Once respiration ceases, the chest cavity is opened by cutting through the ribs exposing the heart and lungs. A 29-gauge insulin syringe is then placed into the heart and a volume of blood is withdrawn. Next, a 19-gauge butterfly catheter attached to an in vivo perfusion apparatus filled with saline is inserted into the left ventricle while the right atrium is cut. The animal is perfused with 50 ml of saline until all blood is cleared from the body as noted by clear fluid running from the heart. Organs and tissues are dissected and imaged for drug accumulation. Agent concentration in blood is measured as described in the previous section.

Therapeutic Ultrasound

Tumor temperature feedback is accomplished using a 30-gauge needle thermocouple (HYP-1, Omega Engineering, Inc., Stanford, Conn.), which is inserted into the center of the tumor and interfaced to a data acquisition system controlled using LabVIEW™ (National Instruments Corp. Austin, Tex.) running on a PC. A proportional-integral differential control (PID) system is used to maintain the tumor temperature at 42° C. for 2 min by controlling the transmitted output power on the ultrasound scanner. The therapeutic beam is swept in the azimuth dimension to fit the tumor dimensions. The animal's core temperature is monitored using a rectal thermocouple and is maintained at ~37° C. during the experiment (Kheirolomoom, A.; Dayton, P. A.; Lum, A. F. H.; Little, E.; Paoli, E. E.; Zheng, H. R.; Ferrara, K. W., Acoustically-active microbubbles conjugated to liposomes: Characterization of a proposed drug delivery carrier. *Journal of Controlled Release* 2007, 118, (3), 275-284).

Other methods described above are also performed with agents, agent-transition metal complexes, and relevant controls. One of skill will understand that other in vivo therapeutic regimens and mouse models known in the art can be used to test the complexes. In addition to ultrasound, other energy sources can also be used to concentrate complexes and/or release complexes from carriers.

Formation of transition metal-agent crystals within carriers increases agent loading, improves plasma stability of the agent, and augments the accumulation of carriers in tumors. Ultrasound increases the accumulation of the carrier complex at a site of interest, e.g., a tumor. The carrier complex circulates stably in blood and yet can be released by heat. The complex is freed from the carriers when insonified within a tumor or other site of interest.

Example 9

Production and Use of Agent and Agent-Transition Metal Complexes in Carriers in Mammals Including Humans A membrane permeable buffer triethanolamine (TEA, pKa: 9.5, membrane permeability coefficient: 0.12 cm/s), is used to load an agent within a carrier. Agents include anthracyclines such as daunorubicin, doxorubicin, epirubicin, idarubicin, mitoxantrone, valrubicin, and irinotecan. Carriers include liposomes, micelles, polymersomes, and nanoparticles. A triethanolamine (TEA) gradient created across the carrier membrane loads an agent efficiently in the absence of a pH gradient or a transition metal ion at neutral pH. The TEA gradient can be 90-270 mM and the pH can be 7.4. Concentration via triethanolamine is then optimized to encapsulate an optimal amount of agent (e.g., 200 mM) inside the intra-carrier medium. To do this, a carrier with a desired diameter is formed using methods known in the art and/or as described above. A TEA gradient is then created across the carrier membrane by separating free TEA from carrier encapsulated TEA using a column such as a Sephadex G-75 column. TEA encapsulating carriers are collected in a solution (e.g., saline) and incubated with an agent in a solution at a pre-determined concentration, mass ratio, temperature, and amount of time (e.g., 2 mg/ml of agent in saline at initial mass ratio of 0.2 mg/mg at 37° C. for 1.5 h, 3 h, 6 h, 12 h, 18 h, or 24 h).

To form a transition metal-agent complex (e.g., at a molar ratio of 1:2) at neutral pH, carriers are prepared in the presence of a transition metal (e.g., 100 mM) and TEA (e.g., 270 mM) with pH adjusted to neutral (e.g., 7.4). Transition metals include manganese, iron, and copper. Carriers include liposomes, micelles, polymersomes, and nanoparticles. Transition metal/TEA carriers are then separated from free transition metal and a TEA gradient (e.g., 90-270 mM) is generated across the carrier membrane; carriers are then incubated in the presence of an agent in solution (e.g., at 2 mg/ml of agent in saline) as described above. Agents include anthracyclines such as daunorubicin, doxorubicin, epirubicin, idarubicin, mitoxantrone, valrubicin, and irinotecan. In some aspects, transition metal/TEA carriers are obtained from a third party and then a TEA gradient (e.g., 90-270 mM) is generated across the carrier membrane; carriers are then incubated in the presence of an agent in solution (e.g., at 2 mg/ml of agent in saline) as described above. Crystal formation between transition metal and agent (e.g., 100 mM: 200 mM) is confirmed, e.g., by quenched fluorescence of agent after digestion of carriers (e.g., with Triton X-100), spectrum change of agent, color change, and/or electron microscopy indicating the presence of dotted structures uniformly distributed within the carriers.

A subject in need of treatment of a condition is selected or identified. For example, the subject can be in need of cancer treatment. The identification of the subject can occur in a clinical setting, or elsewhere, e.g., in the subject's home through the subject's own use of a self-testing kit. The subject is a mammal (e.g., mice, rats, rodents, humans, monkeys, guinea pigs).

Subjects are administered (e.g., intravenously) free agent, agent within carrier, free agent-transition metal complex, agent-transition metal complex within carrier, or a control (e.g., saline).

At time zero, a suitable first dose of free agent, agent within carrier, free agent-transition metal complex, agent-transition metal complex within carrier, or a control is administered to the subject. The free agent, agent within carrier, free agent-transition metal complex, agent-transition metal complex within carrier, or control are formulated as described herein. In some instances ultrasound is applied to the subject simultaneously or after administration of the first dose. In some instances the subject is administered a second agent such as an mTOR inhibitor (e.g., rapamycin). In some instances the second agent is administered to the subject simultaneously, before, or after administration of the first dose. After a period of time following the first dose, e.g., 7 days, 14 days, and 21 days, the subject's condition is evaluated, e.g., by measuring tumor burden in a subject having a tumor. Other relevant criteria can also be measured. The number, placement, route, and strength of doses are adjusted according to the subject's needs or when deemed useful. The number, placement, route, and strength of ultrasound and/or second agent doses are also adjusted according to the subject's needs or when deemed useful, when relevant. Multiple rounds of doses are used where deemed useful. Similar studies are performed with different treatment protocols and administration routes (e.g., intramuscular administration, etc.).

After treatment, the subject's condition is improved relative to the subject's condition existing prior to the treatment, or relative to the condition measured in a similarly afflicted but untreated subject. For example, the subject's tumor burden is improved relative to the subject's tumor burden existing prior to the treatment, or relative to the tumor burden measured in a similarly afflicted but untreated tumor-bearing subject.

Those skilled in the art are familiar with methods and compositions in addition to those specifically set out in the present disclosure which will allow them to practice this invention to the full scope of the claims hereinafter appended.

While the various embodiments of the invention have been particularly shown and described with reference to a preferred embodiment and various alternate embodiments, it will be understood by persons skilled in the relevant art that various changes in form and details can be made therein without departing from the spirit and scope of the invention.

All references, issued patents and patent applications cited within the body of the instant specification are hereby incorporated by reference in their entirety, for all purposes.

REFERENCES

1. Allen, T., Cheng W W, Hare J I, Laginha K M. *Anticancer Agents Med Chem* 2006, 6, (6), 513-523.
2. Batist, G.; Ramakrishnan, G.; Rao, C. S.; Chandrasekharan, A.; Gutheil, J.; Guthrie, T.; Shah, P.; Khojasteh, A.; Nair, M. K.; Hoelzer, K.; Tkaczuk, K.; Park, Y. C.; Lee, L. W. *Journal of Clinical Oncology* 2001, 19, (5), 1444-1454.
3. Vanhoesel, Q.; Steerenberg, P. A.; Crommelin, D. J. A.; Vandijk, A.; Vanoort, W.; Klein, S.; Douze, J. M. C.; Dewildt, D. J.; Hillen, F. C. *Cancer Research* 1984, 44, (9), 3698-3705.
4. Drummond, D., Noble, C O, Hayes M E, Park, J W, Kirpotin D B. *Journal of Pharmaceutical Sciences* 2008, 97, (11), 4696-4740.
5. Unezaki, S.; Maruyama, K.; Ishida, O.; Suginaka, A.; Hosoda, J.; Iwatsuru, M. *International Journal of Pharmaceutics* 1995, 126, (1-2), 41-48.
6. Working, P. K.; Newman, M. S.; Huang, S. K.; Mayhew, E.; Vaage, J.; Lasic, D. D. *Journal of Liposome Research* 1994, 4, (1), 667-687.
7. Gianni, L.; Herman, E. H.; Lipshultz, S. E.; Minotti, G.; Sarvazyan, N.; Sawyer, D. B. *J Clin Oncol* 2008, 26, (22), 3777-3784.
8. Dicko, A.; Tardi, P.; Xie, X. W.; Mayer, L. *International Journal of Pharmaceutics* 2007, 337, (1-2), 219-228.
9. Ramsay, E.; Alnajim, J.; Anantha, M.; Taggar, A.; Thomas, A.; Edwards, K.; Karlsson, G.; Webb, M.; Bally, M. *Pharmaceutical Research* 2006, 23, (12), 2799-2808.
10. Cheung, B. C. L.; Sun, T. H. T.; Leenhouts, J. M.; Cullis, P. R. *Biochimica Et Biophysica Acta*-Biomembranes 1998, 1414, (1-2), 205-216.
11. Wallace, K. B. *Toxicology and Applied Pharmacology* 1986, 86, (1), 69-79.
12. May, P. M.; Williams, G. K.; Williams, D. R. *European Journal of Cancer* 1980, 16, (9), 1275-1276.
13. Tritton, T. R.; Yee, G. *Science* 1982, 217, (4556), 248-250.
14. Abraham, S. A.; Edwards, K.; Karlsson, G.; Macintosh, S.; Mayer, L. D.; McKenzie, C.; Bally, M. B. *Biochimica Et Biophysica Acta-Biomembranes* 2002, 1565, (1), 41-54.
15. Chiu, G. N. C.; Abraham, S. A.; Ickenstein, L. M.; Ng, R.; Karlsson, G.; Edwards, K.; Wasan, E. K.; Bally, M. B. *Journal of Controlled Release* 2005, 104, (2), 271-288.
16. Beraldo, H.; Garniersuillerot, A.; Tosi, L. *Inorganic Chemistry* 1983, 22, (26), 4117-4124.
17. Greenaway, F. T.; Dabrowiak, J. C. *Journal of Inorganic Biochemistry* 1982, 16, (2), 91-107.
18. Andresen, T. L.; Jensen, S. S.; Jorgensen, K. *Progress in Lipid Research* 2005, 44, (1), 68-97.
19. Kim, K. W.; Moretti, L.; Mitchell, L. R.; Jung, D. K.; Lu, B. *Clinical Cancer Research* 2009, 15, (19), 6096-6105.
20. Kheirolomoom, A.; Kruse, D. E.; Qin, S.; Watson, K. E.; Lai, C.-Y.; Young, L. J. T.; Cardiff, R. D.; Ferrara, K. W. *Journal of Controlled Release* 2010, 141, (2), 128-136.
21. Lewis, G., Jr.; Peng, W.; Lewis, G., Sr.; Olbricht, W. *AIP Conference Proceedings* 2009, 1113, 403-407.
22. Namba, R.; Young, L. J.; Abbey, C. K.; Kim, L.; Damonte, P.; Borowsky, A. D.; Qi, J. Y.; Tepper, C. G.; MacLeod, C. L.; Cardiff, R. D.; Gregg, J. P. *Clinical Cancer Research* 2006, 12, (8), 2613-2621.
23. Maeda, H., The enhanced permeability and retention (EPR) effect in tumor vasculature: The key role of tumor-selective macromolecular drug targeting. In *Advances in Enzyme Regulation, Vol 41*, ed.; Weber, G., 'Ed.'^'Eds.' Pergamon-Elsevier Science Ltd: Oxford, 2001; 'Vol.' 41, p^pp 189-207.
24. Senger, D. R.; Galli, S. J.; Dvorak, A. M.; Perruzzi, C. A.; Harvey, V. S.; Dvorak, H. F. *Science* 1983, 219, (4587), 983-985.
25. Muneeb, A.; Anatoly, N. L.; Vladimir, T.; Herve, T.; Anatoly, N. S.; Goldberg, S. N. *Journal of vascular and interventional radiology: JVIR* 2005, 16, (10), 1365-1371.
26. Yuan, F.; Leunig, M.; Huang, S. K.; Berk, D. A.; Papahadjopoulos, D.; Jain, R. K. *Cancer Research* 1994, 54, (13), 3352-3356.
27. Monsky, W. L.; Fukumura, D.; Gohongi, T.; Ancukiewcz, M.; Weich, H. A.; Torchilin, V. P.; Yuan, F.; Jain, R. K. *Cancer Research* 1999, 59, (16), 4129-4135.
28. Gabizon, A. A.; Barenholz, Y.; Bialer, M. *Pharmaceutical Research* 1993, 10, (5), 703-708.
29. Kheirolomoom, A.; Ferrara, K. W. *Biomaterials* 2007, 28, (29), 4311-4320.
30. Seo, J. W.; Zhang, H.; Kukis, D. L.; Meares, C. F.; Ferrara, K. W. *Bioconjugate Chemistry* 2008, 19, (12), 2577-2584.
31. Li, X. G.; Hirsh, D. J.; Cabral-Lilly, D.; Zirkel, A.; Gruner, S. M.; Janoff, A. S.; Perkins, W. R. *Biochimica Et Biophysica Acta-Biomembranes* 1998, 1415, (1), 23-40.
32. Lasic, D. D.; Ceh, B.; Stuart, M. C. A.; Guo, L.; Frederik, P. M.; Barenholz, Y. *Biochimica Et Biophysica Acta-Biomembranes* 1995, 1239, (2), 145-156.
33. Tardi, P. G.; Gallagher, R. C.; Johnstone, S.; Harasym, N.; Webb, M.; Bally, M. B.; Mayer, L. D. *Biochimica Et Biophysica Acta-Biomembranes* 2007, 1768, (3), 678-687.
34. Madden, T. D.; Harrigan, P. R.; Tai, L. C. L.; Bally, M. B.; Mayer, L. D.; Redelmeier, T. E.; Loughrey, H. C.; Tilcock, C. P. S.; Reinish, L. W.; Cullis, P. R. *Chemistry and Physics of Lipids* 1990, 53, (1), 37-46.
35. Haran, G.; Cohen, R.; Bar, L. K.; Barenholz, Y. *Biochimica Et Biophysica Acta* 1993, 1151, (2), 201-215.
36. Mayer, L. D.; Bally, M. B.; Hope, M. J.; Cullis, P. R. *Biochimica Et Biophysica Acta* 1985, 816, (2), 294-302.
37. Clerc, S.; Barenholz, Y. *Biochimica Et Biophysica Acta-Biomembranes* 1995, 1240, (2), 257-265.
38. Palmer, G. M.; Boruta, R. J.; Viglianti, B. L.; Lan, L.; Spasojevic, I.; Dewhirst, M. W. *Journal of Controlled Release* 2010, 142, (3), 457-464.
39. Ridge, J. A.; Collin, C.; Bading, J. R.; Hancock, C.; Conti, P. S.; Daly, J. M.; Raaf, J. H. *Cancer Research* 1988, 48, (16), 4584-4587.
40. Weinberg, B. D.; Patel, R. B.; Wu, H. P.; Blanco, E.; Barnett, C. C.; Exner, A. A.; Saidel, G. M.; Gao, J. M. *Medical & Biological Engineering & Computing* 2008, 46, (10), 1039-1049.

The invention claimed is:

1. A composition, comprising: a temperature-sensitive liposome (TSL) comprising triethanolamine (TEA) and a crystal comprising a doxorubicin-copper crystalline complex, wherein the doxorubicin and copper are present in a 2:1 molar ratio.

2. The composition of claim 1, wherein the TEA concentration within the TSL is up to 810 mM.

3. The composition of claim 2, wherein the TEA concentration within the TSL is 270 mM.

4. The composition of claim 1, wherein said crystal comprising said crystalline complex has a dimension of from 0.1 nm to 50 nm.

5. The composition of claim 1, wherein said crystalline complex comprises 200 mM doxorubicin and 100 mM copper.

6. The composition of claim 1, wherein said crystalline complex comprises 200 mM doxorubicin and 100 mM copper and the TSL comprises 1,2-dipalmitoyl-sn-glycero-3-phospho-choline (DPPC), 1-palmitoyl-2-hydroxy-sn-glycero-3-phosphocholine (MPPC) and 1,2 distearoyl-sn-glycero-3-phosphoethanolamine-N-Methoxy polyethyleneglycol-2000 (DSPE-PEG2k), and wherein the molar ratio of DPPC:MPPC:DSPE-PEG2k is 86:10:4, respectively.

7. The composition of claim 1, wherein said crystal comprising said crystalline complex is insoluble in a buffered salt solution at pH 7.4 and 37° C.

8. The composition of claim 1, wherein said crystal comprising said crystalline complex is soluble in a buffered salt solution at pH 5.0 and 37° C.

9. The composition of claim 1, wherein the TSL comprises DPPC,: 1,2-distearoyl-sn-glycero-3-phosphocholine (DSPC), and DSPE-PEG2k.

10. The composition of claim 9, wherein the molar ratio of DPPC:DSPC:DSPE-PEG2k is 85.5:9.5:5, respectively.

11. The composition of claim 1, wherein the TSL comprises DPPC:DSPC:cholesterol (chol):DSPE-PEG2k.

12. The composition of claim 11, wherein the molar ratio of DPPC:DSPC:chol:DSPE-PEG2k is 63:7:25:5, respectively.

13. The composition of claim 1, wherein the TSL comprises DPPC, MPPC, and DSPE-PEG2k.

14. The composition of claim 13, wherein the molar ratio of DPPC:MPPC:DSPE-PEG2k is 86:10:4, respectively.

15. A method for localized delivery of a doxorubicin to a target site, comprising:
administering the composition of claim 1 to a subject, wherein the subject comprises the target site; and
irradiating the target site with an energy source, the irradiating causing accumulation of the doxorubicin-copper complex at the target site or release of the doxorubicin-copper complex from the composition at the target site, thereby producing localized delivery of the doxorubicin to the target site.

16. A method for localized delivery of doxorubicin to a tumor target site, comprising:
administering the composition of claim 1 to a subject, wherein the subject comprises the tumor target site; and
irradiating the tumor target site with an ultrasound source, the irradiating causing accumulation of the complex at the tumor target site, thereby producing localized delivery of doxorubicin to the tumor target site.

17. A method of producing a TSL comprising TEA and a crystal comprising a doxorubicin-copper crystalline complex, comprising: preparing the TSL in the presence of the copper to form a copper containing TSL; creating a triethanolamine (TEA) gradient across the membrane of the copper-containing TSL; incubating the copper-containing TSL in the presence of the doxorubicin; and allowing the doxorubicin-copper crystalline complex to form in the TSL wherein the doxorubicin and copper are present in a 2:1 molar ratio.

18. The method of claim 17, wherein the TEA gradient across the TSL membrane is 90-270 mM.

19. The method of claim 17, wherein the TSL comprises DPPC, MPPC and DSPE-PEG2k.

20. The method of claim 19, wherein the molar ratio of DPPC:MPPC:DSPE-PEG2k is 86:10:4, respectively.

21. The method of claim 17, wherein the crystalline complex comprises 200 mM doxorubicin and 100 mM copper.

22. The method of claim 17, wherein the TSL is prepared in the presence of 100 mM copper, the TEA gradient across the TSL membrane is 90-270 mM, and the copper-containing TSL is incubated in the presence of 2 mg/ml doxorubicin.

23. A method of producing a TSL comprising TEA and a crystal comprising a doxorubicin-copper crystalline complex, wherein the doxorubicin and copper are present in a 2:1 molar ratio of agent:transition metal, comprising: acquiring a copper-containing TSL; creating a TEA gradient across the membrane of the copper-containing TSL; incubating the copper-containing TSL in the presence of the doxorubicin; and allowing the doxorubicin-copper crystalline complex to form in the liposome.

24. The method of claim 23, wherein the TEA gradient across the TSL membrane is 90-270 mM.

25. The method of claim 23, wherein the crystalline complex comprises 200 mM doxorubicin and 100 mM copper.

26. The method of claim 23, wherein the TSL comprises DPPC, MPPC and DSPE-PEG2k.

27. The method of claim 26, wherein the-molar ratio of DPPC:MPPC:DSPE-PEG2k is 86:10:4, respectively.

28. The method of claim 23, wherein the copper-containing TSL comprises 100 mM copper, the TEA gradient across the TSL membrane is 90-270 mM the copper-containing TSL is incubated in the presence of 2 mg/ml doxorubicin and the TSL comprises DPPC:MPPC:DSPE-PEG2k in a molar ratio of 86:10:4, respectively.

29. A composition comprising a TSL comprising a crystal comprising a doxorubicin-copper crystalline complex, the composition produced by the method of acquiring a TSL comprising copper and a TSL membrane; creating a TEA gradient across the TSL membrane; incubating the TSL in the presence of doxorubicin; and allowing the doxorubicin-copper crystalline complex to form in a 2:1 molar ratio in the TSL.

30. The composition of claim 29, wherein the TEA concentration within the TSL is up to 810 mM.

31. The composition of claim 30, wherein the TEA concentration with the TSL is 270 mM.

32. The composition of claim 29, wherein the doxorubicin is present in the TSL at a concentration of 200 mM and the copper is present in the TSL at a concentration of 100 mM.

33. The composition of claim 29, wherein the TEA gradient across the TSL membrane is 90-270 mM.

34. The composition of claim 29, wherein the TSL comprises DPPC and MPPC and DSPE-PEG2k.

35. The composition of claim 32, wherein the-molar ratio of DPPC:MPPC:DSPE-PEG2k is 86:10:4, respectively.

36. A composition comprising a TSL comprising a crystal comprising a doxorubicin-copper crystalline complex, the composition produced by the method of acquiring a TSL comprising 100 mM copper and a TSL membrane; creating a TEA gradient of 90-270 mM across the TSL membrane; incubating the TSL in the presence of 2 mg/ml doxorubicin; and allowing the doxorubicin-copper crystalline complex to form in the TSL, wherein the doxorubicin is present in the TSL at a concentration of 200 mM and the copper is present in the TSL at a concentration of 100 mM, and the TSL comprises DPPC and MPPC and DSPE-PEG2k in a molar ratio is 86:10:4, respectively.

37. The method of claim 1, wherein said TEA concentration within the TSL is up to 810 mM, wherein said crystalline complex comprises 200 mM doxorubicin and 100 mM copper;

wherein said crystal comprising said crystalline complex has a dimension of from 0.1 nm to 50 nm; wherein said TSL comprises DPPC, MPPC and DSPE-PEG2k; and wherein the molar ratio of DPPC:MPPC:DSPE-PEG2k is 86:10:4, respectively.

38. The method of claim 17, wherein said crystalline complex comprises 200 mM doxorubicin and 100 mM copper, wherein said TEA gradient across the TSL membrane is 90-270 mM; wherein said TSL comprises DPPC, MPPC and DSPE-PEG2k; and wherein the molar ratio of DPPC:MPPC:DSPE-PEG2k is 86:10:4, respectively.

39. The composition of claim 1, wherein the TEA concentration within the TSL is up to 810 mM; wherein said crystalline complex comprises 200 mM doxorubicin and 100 mM copper; wherein said TSL comprises DPPC, MPPC and DSPE-PEG2k; and wherein the molar ratio of DPPC:MPPC:DSPE-PEG2k is 86:10:4, respectively.

* * * * *

UNITED STATES PATENT AND TRADEMARK OFFICE
CERTIFICATE OF CORRECTION

PATENT NO. : 9,844,656 B2
APPLICATION NO. : 13/581274
DATED : December 19, 2017
INVENTOR(S) : Katherine W. Ferrara and Azedah Kheirolomoom Page 1 of 1

It is certified that error appears in the above-identified patent and that said Letters Patent is hereby corrected as shown below:

In the Claims

Column 53 Claim 9, Line(s): 23-24: replace "DPPC,: 1,2-distearoyl-sn-glycero-3-phosphocholine (DSPC)" with -- DPPC, 1,2-distearoyl-sn-glycero-3-phosphocholine (DSPC) --

Column 53 Claim 11, Line(s): 28: replace "DPPC:DSPC:cholesterol (chol):DSPE-PEG2k." with -- DPPC, DSPC, cholesterol (chol), and DSPE-PEG2k. --

Column 54 Claim 28, Line(s) 31: replace "TSL membrane is 90-270 mM the copper-containing TSL is incubated in the presence of 2 mg/ml doxorubicin and the TSL comprises" with -- TSL membrane is 90-270 mM, the copper-containing TSL is incubated in the presence of 2 mg/ml doxorubicin, and the TSL comprises --

Column 54 Claim 36, Line(s): 66: replace "DPPC and MPPC and DSPE-PEG2k" with -- DPPC, MPPC and DSPE-PEG2k --

Column 55 Claim 37, Line(s): 1: replace "The method of claim 1" with -- The method of claim 15 --

Signed and Sealed this
Tenth Day of July, 2018

Andrei Iancu
*Director of the United States Patent and Trademark Office*